(12) United States Patent
Fujimura et al.

(10) Patent No.: US 7,491,554 B2
(45) Date of Patent: Feb. 17, 2009

(54) CARRIER OF A DIAMOND FINE PARTICLE FOR IMMOBILIZING VIRUS

(75) Inventors: Tadamasa Fujimura, D-1404, Chuougaiku, 535-2, Shinanochou, Totuka-ku, Yokohama-Shi, Kangawa-ken, 244-0801 (JP); Mituru Akashi, Kagoshima (JP); Junji Watanabe, Chigasaki (JP); Masato Sone, Koganei (JP)

(73) Assignee: Tadamasa Fujimura, Yokohama-shi (JP)

( * ) Notice: Subject to any disclaimer, the term of this patent is extended or adjusted under 35 U.S.C. 154(b) by 747 days.

(21) Appl. No.: 10/420,947

(22) Filed: Apr. 23, 2003

(65) Prior Publication Data

US 2004/0214159 A1    Oct. 28, 2004

(51) Int. Cl.
- *B01J 3/06* (2006.01)
- *A61K 39/38* (2006.01)
- *A61K 39/21* (2006.01)
- *G01N 33/544* (2006.01)
- *A61K 39/385* (2006.01)

(52) U.S. Cl. .................... 436/528; 424/489; 424/184.1; 424/208.1; 423/446

(58) Field of Classification Search ............... None
See application file for complete search history.

(56) References Cited

U.S. PATENT DOCUMENTS 5,334,394 A * 8/1994 Kossovsky et al. .......... 424/494
2001/0009759 A1 * 7/2001 Sato et al. .................. 435/5
2002/0197417 A1 * 12/2002 Nakamura et al. .......... 427/585

FOREIGN PATENT DOCUMENTS

JP    2001-139532    5/2001

OTHER PUBLICATIONS

Kuznetsov et al. Carbon, vol. 29 No. 4/5, pp. 665-668, 1991.*
Johnson R.C., DNA Molecules form nanodevice scaffolding, EETimes.com, Feb. 18, 2003, 5:40 PM.*
Kuznetsov et al., Study of Ultradispersed diamond powders obtained using explosion energy, Carbon, vol. 29 No. 4/5, pp. 665-668, 1991.*
Johnson R.C., DNA Molecules form nanodevice scaffolding, Posted at EETimes.com on Feb. 18, 2003, 5:40 pm [Retrived Oct. 20, 2006], Retrived from the internet:<URL: http://www.eetimes.com/story/OEG20030218S0065>.*
Saifuddin et al., Interaction of mannose-binding lectin with primary isolates of human immunodeficiency virus type 1, 2000, Journal of General Virology, vol. 81, pp. 949-955.*
Mitsuru Akashi, et al.; *Development of an AIDS Vaccine Using a Polymer Nano-Sphere*; Chemical Industries; 2001, vol. 9, pp. 41-47.

* cited by examiner

*Primary Examiner*—Bruce Campell
*Assistant Examiner*—Benjamin P Blumel
(74) *Attorney, Agent, or Firm*—Westerman, Hattori, Daniels & Adrian, LLP.

(57) ABSTRACT

The present invention provides a carrier for immobilizing a bio-derived polymer, and especially, the present invention provides a carrier of diamond fine particle for immobilizing a DNA, RNA, protein and peptide, as well as a DNA chip substrate, a carrier for trapping virus and a vaccine. The carrier is prepared by the steps comprising: preparing an initial mixture including a diamond and a non-diamond by means of explosion of a detonating agent; subjecting the initial mixture to an oxidation treatment to obtain a suspension solution including the diamond; and separating a phase including the diamond. According to the present invention, after the oxidation treatment, a basic material having per se volatility or to generate a decomposed material having volatility is added, to neutralize with nitric acid, and thereby obtained diamond fine particle has a functional group on the surface thereof.

17 Claims, 18 Drawing Sheets

| Ch. | Particle diameter(μm) | Total (%) | Amount in channel(%) | Ch. | Particle diameter(μm) | Total (%) | Amount in channel(%) | Ch. | Particle diameter(μm) | Total (%) | Amount in channel(%) |
|---|---|---|---|---|---|---|---|---|---|---|---|
| 1 | 0.10 | 0.00 | 0.00 | 21 | 3.02 | 53.38 | 11.87 | 41 | 91.09 | 100.00 | 0.00 |
| 2 | 0.12 | 0.00 | 0.00 | 22 | 3.58 | 66.12 | 12.74 | 42 | 108.01 | 100.00 | 0.00 |
| 3 | 0.14 | 0.00 | 0.00 | 23 | 4.24 | 78.06 | 11.94 | 43 | 128.07 | 100.00 | 0.00 |
| 4 | 0.17 | 0.00 | 0.00 | 24 | 5.03 | 87.46 | 9.40 | 44 | 151.86 | 100.00 | 0.00 |
| 5 | 0.20 | 0.00 | 0.00 | 25 | 5.97 | 93.75 | 6.29 | 45 | 180.07 | 100.00 | 0.00 |
| 6 | 0.23 | 0.00 | 0.00 | 26 | 7.07 | 97.60 | 3.85 | 46 | 213.51 | 100.00 | 0.00 |
| 7 | 0.28 | 0.00 | 0.00 | 27 | 8.39 | 99.48 | 1.88 | 47 | 253.17 | 100.00 | 0.00 |
| 8 | 0.33 | 0.00 | 0.00 | 28 | 9.95 | 99.99 | 0.51 | 48 | 300.19 | 100.00 | 0.00 |
| 9 | 0.39 | 0.05 | 0.05 | 29 | 11.79 | 100.00 | 0.01 | 49 | 355.95 | 100.00 | 0.00 |
| 10 | 0.46 | 0.27 | 0.22 | 30 | 13.98 | 100.00 | 0.00 | 50 | 422.06 | 100.00 | 0.00 |
| 11 | 0.55 | 0.79 | 0.52 | 31 | 16.58 | 100.00 | 0.00 | 51 | 500.45 | 100.00 | 0.00 |
| 12 | 0.65 | 1.59 | 0.80 | 32 | 19.66 | 100.00 | 0.00 | 52 | 593.40 | 100.00 | 0.00 |
| 13 | 0.77 | 2.39 | 0.80 | 33 | 23.31 | 100.00 | 0.00 | 53 | 703.61 | 100.00 | 0.00 |
| 14 | 0.92 | 4.66 | 2.27 | 34 | 27.64 | 100.00 | 0.00 | | | | |
| 15 | 1.09 | 8.46 | 3.80 | 35 | 32.78 | 100.00 | 0.00 | | | | |
| 16 | 1.29 | 13.40 | 4.94 | 36 | 38.86 | 100.00 | 0.00 | | | | |
| 17 | 1.53 | 18.97 | 5.57 | 37 | 46.08 | 100.00 | 0.00 | | | | |
| 18 | 1.81 | 24.99 | 6.02 | 38 | 54.64 | 100.00 | 0.00 | | | | |
| 19 | 2.15 | 32.37 | 7.38 | 39 | 64.79 | 100.00 | 0.00 | | | | |
| 20 | 2.55 | 41.51 | 9.14 | 40 | 76.82 | 100.00 | 0.00 | | | | |

| Ch. | Particle diameter (μm) | Total (%) | Amount in channel (%) | Ch. | Particle diameter (μm) | Total (%) | Amount in channel (%) | Ch. | Particle diameter (μm) | Total (%) | Amount in channel (%) |
|---|---|---|---|---|---|---|---|---|---|---|---|
| 1 | 0.10 | 0.00 | 0.00 | 21 | 3.02 | 65.09 | 11.08 | 41 | 91.09 | 100.00 | 0.00 |
| 2 | 0.12 | 0.00 | 0.00 | 22 | 3.58 | 76.46 | 11.37 | 42 | 108.01 | 100.00 | 0.00 |
| 3 | 0.14 | 0.00 | 0.00 | 23 | 4.24 | 86.45 | 9.99 | 43 | 128.07 | 100.00 | 0.00 |
| 4 | 0.17 | 0.00 | 0.00 | 24 | 5.03 | 93.51 | 7.06 | 44 | 151.86 | 100.00 | 0.00 |
| 5 | 0.20 | 0.00 | 0.00 | 25 | 5.97 | 97.47 | 3.96 | 45 | 180.07 | 100.00 | 0.00 |
| 6 | 0.23 | 0.00 | 0.00 | 26 | 7.07 | 99.21 | 1.74 | 46 | 213.51 | 100.00 | 0.00 |
| 7 | 0.28 | 0.00 | 0.00 | 27 | 8.39 | 100.00 | 0.79 | 47 | 253.17 | 100.00 | 0.00 |
| 8 | 0.33 | 0.01 | 0.01 | 28 | 9.95 | 100.00 | 0.00 | 48 | 300.19 | 100.00 | 0.00 |
| 9 | 0.39 | 0.12 | 0.11 | 29 | 11.79 | 100.00 | 0.00 | 49 | 355.95 | 100.00 | 0.00 |
| 10 | 0.46 | 0.62 | 0.50 | 30 | 13.98 | 100.00 | 0.00 | 50 | 422.06 | 100.00 | 0.00 |
| 11 | 0.55 | 1.80 | 1.18 | 31 | 16.58 | 100.00 | 0.00 | 51 | 500.45 | 100.00 | 0.00 |
| 12 | 0.65 | 3.81 | 2.01 | 32 | 19.66 | 100.00 | 0.00 | 52 | 593.40 | 100.00 | 0.00 |
| 13 | 0.77 | 6.40 | 2.59 | 33 | 23.31 | 100.00 | 0.00 | 53 | 703.61 | 100.00 | 0.00 |
| 14 | 0.92 | 10.75 | 4.35 | 34 | 27.64 | 100.00 | 0.00 | | | | |
| 15 | 1.09 | 16.60 | 5.85 | 35 | 32.78 | 100.00 | 0.00 | | | | |
| 16 | 1.29 | 23.39 | 6.79 | 36 | 38.86 | 100.00 | 0.00 | | | | |
| 17 | 1.53 | 30.41 | 7.02 | 37 | 46.08 | 100.00 | 0.00 | | | | |
| 18 | 1.81 | 37.32 | 6.91 | 38 | 54.64 | 100.00 | 0.00 | | | | |
| 19 | 2.15 | 45.03 | 7.71 | 39 | 64.79 | 100.00 | 0.00 | | | | |
| 20 | 2.55 | 54.01 | 8.98 | 40 | 76.82 | 100.00 | 0.00 | | | | |

| Ch. | Particle diameter (μm) | Total (%) | Amount in channel (%) | Ch. | Particle diameter (μm) | Total (%) | Amount in channel (%) | Ch. | Particle diameter (μm) | Total (%) | Amount in channel (%) |
|---|---|---|---|---|---|---|---|---|---|---|---|
| 1 | 0.10 | 0.00 | 0.00 | 21 | 3.02 | 46.21 | 10.96 | 41 | 91.09 | 100.00 | 0.00 |
| 2 | 0.12 | 0.00 | 0.00 | 22 | 3.58 | 58.37 | 12.16 | 42 | 108.01 | 100.00 | 0.00 |
| 3 | 0.14 | 0.00 | 0.00 | 23 | 4.24 | 70.29 | 11.92 | 43 | 128.07 | 100.00 | 0.00 |
| 4 | 0.17 | 0.00 | 0.00 | 24 | 5.03 | 80.43 | 10.14 | 44 | 151.86 | 100.00 | 0.00 |
| 5 | 0.20 | 0.00 | 0.00 | 25 | 5.97 | 88.20 | 7.77 | 45 | 180.07 | 100.00 | 0.00 |
| 6 | 0.23 | 0.00 | 0.00 | 26 | 7.07 | 93.88 | 5.68 | 46 | 213.51 | 100.00 | 0.00 |
| 7 | 0.28 | 0.00 | 0.00 | 27 | 8.39 | 97.61 | 3.73 | 47 | 253.17 | 100.00 | 0.00 |
| 8 | 0.33 | 0.00 | 0.00 | 28 | 9.95 | 99.59 | 1.98 | 48 | 300.19 | 100.00 | 0.00 |
| 9 | 0.39 | 0.02 | 0.02 | 29 | 11.79 | 99.95 | 0.36 | 49 | 355.95 | 100.00 | 0.00 |
| 10 | 0.46 | 0.11 | 0.09 | 30 | 13.98 | 100.00 | 0.05 | 50 | 422.06 | 100.00 | 0.00 |
| 11 | 0.55 | 0.33 | 0.22 | 31 | 16.58 | 100.00 | 0.00 | 51 | 500.45 | 100.00 | 0.00 |
| 12 | 0.65 | 0.58 | 0.25 | 32 | 19.66 | 100.00 | 0.00 | 52 | 593.40 | 100.00 | 0.00 |
| 13 | 0.77 | 0.58 | 0.00 | 33 | 23.31 | 100.00 | 0.00 | 53 | 703.61 | 100.00 | 0.00 |
| 14 | 0.92 | 1.95 | 1.37 | 34 | 27.64 | 100.00 | 0.00 | | | | |
| 15 | 1.09 | 4.99 | 3.04 | 35 | 32.78 | 100.00 | 0.00 | | | | |
| 16 | 1.29 | 9.39 | 4.40 | 36 | 38.86 | 100.00 | 0.00 | | | | |
| 17 | 1.53 | 14.57 | 5.18 | 37 | 46.08 | 100.00 | 0.00 | | | | |
| 18 | 1.81 | 20.24 | 5.67 | 38 | 54.64 | 100.00 | 0.00 | | | | |
| 19 | 2.15 | 27.04 | 6.80 | 39 | 64.79 | 100.00 | 0.00 | | | | |
| 20 | 2.55 | 35.25 | 8.21 | 40 | 76.82 | 100.00 | 0.00 | | | | |

| Ch. | Particle diameter (μm) | Total(%) | Amount in channel(%) | Ch. | Particle diameter (μm) | Total(%) | Amount in channel(%) | Ch. | Particle diameter (μm) | Total(%) | Amount in channel(%) |
|---|---|---|---|---|---|---|---|---|---|---|---|
| 1 | 0.10 | 0.00 | 0.00 | 21 | 3.02 | 40.83 | 7.23 | 41 | 91.09 | 100.00 | 0.00 |
| 2 | 0.12 | 0.00 | 0.00 | 22 | 3.58 | 49.14 | 8.31 | 42 | 108.01 | 100.00 | 0.00 |
| 3 | 0.14 | 0.00 | 0.00 | 23 | 4.24 | 57.45 | 8.31 | 43 | 128.07 | 100.00 | 0.00 |
| 4 | 0.17 | 0.00 | 0.00 | 24 | 5.03 | 64.59 | 7.14 | 44 | 151.86 | 100.00 | 0.00 |
| 5 | 0.20 | 0.00 | 0.00 | 25 | 5.97 | 70.33 | 5.74 | 45 | 180.07 | 100.00 | 0.00 |
| 6 | 0.23 | 0.00 | 0.00 | 26 | 7.07 | 75.31 | 4.98 | 46 | 213.51 | 100.00 | 0.00 |
| 7 | 0.28 | 0.00 | 0.00 | 27 | 8.39 | 79.86 | 4.55 | 47 | 253.17 | 100.00 | 0.00 |
| 8 | 0.33 | 0.00 | 0.00 | 28 | 9.95 | 83.93 | 4.07 | 48 | 300.19 | 100.00 | 0.00 |
| 9 | 0.39 | 0.03 | 0.03 | 29 | 11.79 | 87.18 | 3.25 | 49 | 355.95 | 100.00 | 0.00 |
| 10 | 0.46 | 0.18 | 0.15 | 30 | 13.98 | 89.54 | 2.36 | 50 | 422.06 | 100.00 | 0.00 |
| 11 | 0.55 | 0.52 | 0.34 | 31 | 16.58 | 91.16 | 1.62 | 51 | 500.45 | 100.00 | 0.00 |
| 12 | 0.65 | 0.99 | 0.47 | 32 | 19.66 | 92.66 | 1.50 | 52 | 593.40 | 100.00 | 0.00 |
| 13 | 0.77 | 1.23 | 0.24 | 33 | 23.31 | 94.42 | 1.76 | 53 | 703.61 | 100.00 | 0.00 |
| 14 | 0.92 | 3.08 | 1.85 | 34 | 27.64 | 96.40 | 1.98 | | | | |
| 15 | 1.09 | 6.90 | 3.82 | 35 | 32.78 | 98.27 | 1.87 | | | | |
| 16 | 1.29 | 12.16 | 5.26 | 36 | 38.86 | 99.62 | 1.35 | | | | |
| 17 | 1.53 | 17.86 | 5.70 | 37 | 46.08 | 99.96 | 0.34 | | | | |
| 18 | 1.81 | 23.18 | 5.32 | 38 | 54.64 | 100.00 | 0.04 | | | | |
| 19 | 2.15 | 28.33 | 5.15 | 39 | 64.79 | 100.00 | 0.00 | | | | |
| 20 | 2.55 | 33.60 | 5.27 | 40 | 76.82 | 100.00 | 0.00 | | | | |

SEQUENCE LISTING

<160> NUMBER OF SEQ ID NOS: 1

<210> SEQ ID NO 1
<211> LENGTH: 24
<212> TYPE: DNA
<213> ORGANISM: Artificial
<220> FEATURE:
<223> OTHER INFORMATION: synthetic DNA

<400> SEQUENCE: 1
gcatctcatt gaccatcata ttat                                    24

CARRIER OF A DIAMOND FINE PARTICLE FOR IMMOBILIZING VIRUS

The present invention relates to a carrier for immobilizing a bio-derived polymer, and especially, the present invention relates to a carrier of diamond fine particle for immobilizing a DNA, RNA, protein and peptide. The present invention also relates to a DNA chip substrate, a carrier for trapping virus and a vaccine.

RELATED ART

Recently, it has been focused on a measure using a DNA chip for immobilizing a bio-derived polymer, which significantly promotes scientific research of gene functions. In addition, a vaccine has been actively tried to develop by immobilizing virus, especially, AIDS virus, on a minute-size carrier.

Generally, a DNA chip is a micro array having a solid layer, such as slide glass, which regularly immobilizes a great number of DNA molecules. The DNA chip may make possible to photoelectronically read out indications for analysis as to bonding condition and bonding location with a gene as a sample. The DNA chip may make possible to simultaneously analyze a great number of genes, so that it will be considered to be effective to research to decode gene functions, for example, in the curse of the Human Genome Project. In addition, it will be considered to be effective in resolving mechanisms as to development of a gene, in discriminating a gene polymorph, in specifying a variation gene, ant in discriminating a cancer gene.

In addition to the genes, the DNA chip is an effective measure in researching functions of a bio-derived molecule other than DNA, such as a physiologically active protein and peptide. For example, it is applicable to the developing of a new medicine and diagnosing.

However, the conventional DNA chips are not perfect. For example, according to the measure generally used, the surface of a slide glass or silicone substrate is coated with a poly cationic polymer such as a polylysine, and a DNA is immobilized by using a spotter apparatus. In case of this process, an electric charge of the DNA is used to electrostatically combine it on a carrier of solid phase. Therefore, such DNA may be unintentionally removed from the carrier during hybridization or washing.

On the contrary, there is a type of DNA chip having a support substrate using a diamond (JP Laid-Open Patent Publication No. 2001-139532). In this type, a diamond is used and has good heat conductivity, and therefore, during performing a PCR method, that is a process which repeats heating and cooling steps, it has a merit in saving time for heat cycling. However, such diamond has no functional groups for combining it with a DNA, so that it is necessary to incorporate functional groups thereon for combining it with a DNA. In the process of this incorporation, an ultraviolet ray is irradiated on the diamond while chlorinating it, and then, under the condition of irradiating an ultraviolet ray, the diamond is reacted with ammonia for amination. Thus, the resultant amino group is reacted with an activated diester, which should be previously prepared, so as to incorporate a functional group into the diamond base for combining a DNA. However, this process is complicated and is not an ease method.

By the way, a carrier of nanoscale polymer sphere has been studied to be combined with concanavalin A, a mannose combinable lectin as a sugar recognition protein, for trapping virus, especially, AIDS virus (HIV), which is applicable to use as a vaccine. ["Chemical Industries," volume September 2001, pages 41-46] The nano scale polymer sphere used in this application comprises, for example, a hydrophobic core portion of polystyrene by copolymerization of a polymethacrylic acid macromer and styrene, and a hydrophilic corona portion of polymethacrylic acid. On the surface of the nano scale sphere, carboxyl group of polymethacrylic acid is positioned, which is reacted with the amino group of concanavalin A of mannose combinable lectin, to immobilize the concanavalin A on the surface of the nanoscale sphere, so as to obtain a carrier for trapping AIDS virus. Thereby immobilized concanavalin A recognizes the sugar chain of glucose protein gp120 (mannose), locating at the surface of an AIDS virus, to trap the AIDS virus. The rate of the trapping is approximately 100%. The nanoscale polymer sphere trapping such AIDS virus is tried to be used as an AIDS vaccine having high IgA inductivity. However, since such nanoscale polymer sphere has a high aggregation property and it aggregates in blood resulting in its solidification, safety is not warranted.

THE OBJECTIVES OF THE PRESENT INVENTION

Therefore, the objective of the present invention is to provide a completely novel material or carrier for trapping virus, which solves the conventional problems. Especially, the objective of the present invention is to provide a DNA chip substrate, a carrier for trapping virus, and a virus vaccine.

SUMMARY OF THE INVENTION

The inventors of the present invention had researched to solve the objectives, and finally found a carrier of diamond fine particle for immobilizing virus, which is prepared by the steps comprising: preparing an initial mixture including a diamond and a non-diamond by means of explosion of a detonating agent; subjecting the mixture to oxidation treatment to obtain a suspension solution including the diamond; separating a phase including the diamond, wherein after the oxidation treatment, a basic material having per se volatility or to generate a decomposed material having volatility is added, to neutralize with nitric acid, and thereby obtained diamond fine particle has a functional group on the surface thereof. Especially, the resultant diamond particle has a particle size in the order of nano resulting in having a significant large surface area, and the surface thereof has various kinds and great numbers of functional group, such as carboxyl group, amino group, hydroxyl group and sulfonyl group, and especially, there exists a great number of negative charge functional groups, and thereby, the present invention achieves a significantly good dispersion property, so that it stables in an aqueous suspension solution without aggregation. Further, the diamond particle of the present invention is found to have a significantly good hydrophilicity, to be excellent in biocompatibility, non-toxic and safe to living bodies. Using the diamond particle of the present invention, a significantly useful material or a carrier for trapping virus can be obtained. In addition, using the carrier, a DNA chip substrate, a carrier for trapping virus, and a virus vaccine, which may not accompany with the conventional problems as described before, can be obtained.

The present invention summarized as follows:

(1) There is provided a carrier of a diamond fine particle for immobilizing virus, prepared by the steps comprising:

preparing an initial mixture including a diamond and a non-diamond by means of explosion of a detonating agent;

subjecting the mixture to oxidation treatment to obtain a suspension solution including the diamond;

separating a phase including the diamond, wherein after the oxidation treatment, a basic material having per se volatility or to generate a decomposed material having volatility is added, to neutralize with nitric acid, and thereby obtained diamond fine particle has a functional group on the surface thereof.

(2) There is provided a carrier of a diamond fine particle for immobilizing virus having the following properties:

(i) The diamond fine particle has an element composition including 72 to 89.5% of total carbon, 0.8 to 1.5% of hydrogen, 1.5 to 2.5% of nitrogen, and 10.5 to 25.0% of oxygen.

(ii) The diamond fine particle has no particle size over 1000 nm or below 30 nm, having a narrow distribution of number average particle diameter (ØMn) of 150 to 650 nm.

(iii) The diamond fine particle, when analyzed by an X-ray diffraction (XD) spectrum analysis using Cu—Kα radiation, has the largest peak at a Bragg angle of 43.9° (2θ±2°), strong and characteristic peaks at either of Bragg angles of 73.5° and 95°, a significantly biased halo at a Bragg angle of 17°, and essentially no peak at a Bragg angle of 26.5°.

(iv) The diamond fine particle has a specific surface area of $1.50\times10^5$ m$^2$/kg or more, wherein all of the surface carbon atoms are substantially bonded with hetero atoms, wherein the diamond fine particle has a total absorption space of 0.5 m$^3$/kg or more.

(3) There is provided a carrier of a diamond fine particle for immobilizing virus, the carrier immobilizing a DNA or RNA.

(4) There is provided a carrier of a diamond fine particle for immobilizing virus, the carrier immobilizing a protein or peptide.

(5) There is provided a carrier of a diamond fine particle for immobilizing virus, the protein being a lectin.

(6) There is provided a DNA chip substrate having a support member having a surface, the surface of the support member having the carrier.

(7) There is provided a A carrier for trapping virus, made of the carrier.

(8) There is provided a carrier for trapping virus, the carrier immobilizing a lectin.

(9) There is provided a carrier for trapping virus, the carrier immobilizing a virus, and the virus being a retrovirus.

(10) There is provided a carrier for trapping virus, the retrovirus being an AIDS virus.

(11) There is provided a vaccine of a carrier for trapping virus, the carrier being combined with an AIDS virus or a protein partially constituting the same.

[The Diamond Particle Used in the Present Invention]

First of all, the diamond fine particle used in the present invention (which is hereinafter referred to as UDD fine particle, if necessary) is described in detail.

The UDD fine particle used in the present invention is, as described above, prepared by the steps comprising: preparing an initial mixture including a diamond and a non-diamond by means of explosion of a detonating agent; subjecting the initial mixture to an oxidation treatment to obtain a suspension solution including the diamond; separating a phase including the diamond, wherein after the oxidation treatment, a basic material having per se volatility or to generate a decomposed material having volatility is added, to neutralize with nitric acid, and thereby obtained diamond fine particle has a functional group on the surface thereof. The UDD fine particle of the present invention has particle properties as follows:

(a) (i) The diamond fine particle of the present invention has an elemental composition including 72 to 89.5% of the whole of carbon, 0.8 to 1.5% of hydrogen, 1.5 to 2.5% of nitrogen, and 10.5 to 25.0% of oxygen.

(ii) The diamond fine particle of the present invention excludes those having particle size over 1000 nm or below 30 nm, having a narrow distribution of number average particle diameter (ϕMn) of 150 to 650 nm.

(iii) The diamond fine particle of the present invention, when analyzed by an X-ray diffraction (XD) spectrum using Cu,Kα radiation, has the largest peak at a Bragg angle of 43.9°, large and specific peaks at either of Bragg angles of 73.5° and 95°, a significantly biased halo at a Bragg angle of 17°, and essentially no peak at a Bragg angle of 26.5°.

(iv) The diamond fine particle of the present invention has a specific surface area of $1.50\times10^5$ m$^2$/kg or more, wherein all of the carbon atoms existing on the surface are substantially bonded with hetero atoms, wherein the diamond fine particle has a total absorption space of 0.5 m$^3$/kg or more.

In addition, the diamond fine particle of the present invention may have the particle properties (b) to (f) as follows:

(b) The diamond fine article of the present invention has a particle size distribution in a narrow type that there includes no particle size of 100 nm or more, and of 30 nm or less, having a number average particle diameter (ϕMn) of 300 to 500 nm.

(c) The diamond fine article of the present invention has a specific density in the range of $3.20\times10^3$ kg/m$^3$ to $3.40\times10^3$ kg/m$^3$. The diamond fine article of the present invention has an infrared ray (IR) absorption spectrum showing the largest and broad band near a wavelength of 3500 cm$^{-1}$; a strong and broad peak at a wavelength between 1730 and 1790 cm$^{-1}$, while being biased above and below to extend broadly; a strong and broad band at a wavelength of 1170 cm$^{-1}$; and a moderately strong band at a wavelength of 610 cm$^{-1}$.

(d) The diamond fine article of the present invention has a moderately strong band at a wavelength of 1740 cm$^{-1}$; and a moderately strong band at a wavelength of 1640 cm$^{-1}$; and a broad band near a wavelength of 1260 cm$^{-1}$.

(e) The diamond fine article of the present invention, when analyzed by an X-ray diffraction (XRD) spectrum using Cu,Kα radiation, has the largest peak at a Bragg angle (2θ±2°) of 43.9°, wherein the total intensities of the peaks at other Bragg angles than that of the largest peak is amounted to be 11/89 and 19/81.

(f) The diamond fine particle of the present invention has a specific surface area of $1.95\times10^5$ m$^2$/kg, to $4.04\times10^5$ m$^2$/kg, when being heated at a temperature of 1273° K before being measured by means of BET method.

Crude diamonds (which is hereinafter referred to as blend diamond or BD) used in the present invention can be synthesized by means of shock conversion method, as described in: *Science*, Vol. 133, No. 3467 (1961), pp. 1821-1822; Japanese Laid Open Patent Publications Nos. 1-234311 and 2-141414; *Bull. Soc. Chim. Fr.* Vol. 134 (1997), pp. 875-890; *Diamond and Related Materials*, Vol. 9 (2000), pp. 861-865; *Chemical Physics Letters*, 222 (1994), pp. 343-346; *Carbon*, Vol. 33, No. 12 (1995), pp. 1663-1671; *Physics of the Solid State*, Vol. 42, No. 8 (2000), pp. 1575-1578; *Carbon*, Vol. 33. No. 12 (1995), pp. 1663-1671; K. Xu. Z. Jin, F. Wei and T. Jiang, Energetic Materials, 1, 19 (1993) (in Chinese); Japanese Laid-Open Patent Publications Nos. 63-303806 and 56-26711; British Patent No. 1154633, Japanese Laid-Open Patent Publication No. 3-271109, Japanese Laid-Open International Patent Publication No. 6-505694 (PCT WO 93/13016); *Carbon*, Vol. 22, No. 2, pp. 189-191 (1984); Van Thiei. M. & Rec., F. H., J. Appl. Phys., 62, pp. 1761-1767 (1987); Japanese Laid-Open International Patent Publication of No. 7-505831 (WO 94/18123); U.S. Pat. No. 5,861,349. Preferable methods in the present invention will be explained later in detail.

The crude diamond (blended diamond (BD)) prepared by means of such a shock conversion method (explosion method) has a particle size of several ten to hundred nanometers, or in some cases, to several hundred nanometers, in the form of mixture of UDD particles and non-graphite particles. Each particle of the UDD is composed of an aggregation in which diamond units (nanometer diamond) in a very small size of nanometer cluster having a particle size of 1.5 to 7 nm are strongly aggregated to the extent impossibly or hardly to mechanically crash the aggregation. In other words, the UDD is composed of a hard aggregation having at least four pieces, and generally more than ten to several hundred pieces, of nanometer diamond. The BD includes UDD particles, including, at a very few amount, extreme fine particles of amorphous diamond, graphite, and non-graphite carbon, having a particle size of 1.5 nm or less.

In order to prepare the UDD fine particle used in the present invention, a condensation carbon phase is formed by transition by means of explosion of a detonating agent, followed by subjecting to an oxidation treatment in a liquid phase to decompose a non-diamond portion thereof. Such oxidation treatment may be made by using nitric acid. If desired, impurities of metal oxide are previously dissolved out by means of treatment of hydrochloric acid. First of all, the condensation carbon phase surrounding the blended diamond is oxidized to decompose so as to separate a diamond component from the other carbon components.

Then, the non-diamond carbon covering the surface of the crude diamond is oxidized to decompose and subjected to oxidation etching, for removal. Furthermore, the non-diamond carbon formed on a surface of the diamond is subjected to oxidation etching for removal. The non-diamond carbon covering the surface of the diamond and the non-diamond carbon formed on a surface of the diamond are generally considered to be generated by the mechanism that the formed diamond, in a process of transition by means of explosion of a detonating agent for forming diamond, is under the influence of rapid reduction of the pressure at a remained raised temperate. The non-diamond carbon covering the surface of the diamond and the non-diamond carbon formed on a surface of the nanometer diamond may be oxidized to decompose and subjected to oxidation etching, possibly at simultaneous manner, but preferably at sequence manner.

The nanometer diamond constituting the UDD product purified has an average diameter of $42\pm2\times10^{-10}$ when measured by coherent scattering photoelectric field (CSF). According to the result of the measurement of the product of the present invention, a property due to having a diamond crystalline lattice in the core portion of the UDD is detected, as well as a small amount of aggregations of carbon atom having an atom interval smaller than $1.5\times10^{-10}$ m, not forming a lattice to generally disperse in the UDD particle, is detected. On the other hand, another measurement is made to reveal to have a property of aggregations of carbon atom at a very small amount at the internal interface of the particle in the purified product is detected. Since its interatomic distance is plotted in a Gaussian distribution, it is found that that the aggregation body of carbon atoms formed at the internal interface of the particle of amorphous.

Conventionally, such kind of UDD fine particles have a specific surface area of $(2.5\ \text{to}\ 3.5)\times10^3\ \text{m}^2/\text{g}$ and a porous volume of $(0.3\ \text{to}\ 1.0)\times10^{-3}\ \text{m}^3/\text{kg}$, showing a less reduction of specific surface area when being heated at 1273 degree K. Also, conventional UDD fine particles have, in the state of suspension, a particle size as large as $100\times10^{-6}$ m, but when being dried, the conventional UDD fine particles aggregate to be polydisperse powder. Also, when being heated under an inert atmosphere, the UDD fine particles are increasing to change it into a spherollite form at a temperature as low as 873 degree K. The UDD fine particle in a spherollite form may be broken by imposing a mechanical pressure of $(100\ \text{to}\ 150)\times10^6$ Pa. Thereafter, it will be less likely to aggregate again or to form a polydisperse powder.

On the contrary, the UDD fine particle of the present invention is prepared under an uneven condition in the process of synthesis in the present invention, so as to have defects in a high density, a large surface of $1.50\times10^5\ \text{m}^2/\text{kg}$ or more, being remarkably large compared with the conventional ones. Also, such a large surface, as a whole, has a highly developed activity to have an excess enthalpy. Also, the UDD fine particle has a total absorption space of $0.5\ \text{m}^3/\text{kg}$ or more based on the condition of $p/p_s=0.995$ (wherein "p" represents surface area inside the pore filled with $N_2$ gas and "$p_s$" represents a partial pressure of nitrogen gas for forming a single layer of gas), whose value is remarkably different from that of the conventional ones. These properties should prove the utility of the UUD fine particle of the present invention.

The UDD fine particle of the present invention has volatile substances and solid impurities deposited on the surface thereof. The volatile substances may be acid residues (in the state after chemical purification process) such as CO, $CO_2$, $N_2$, $H_2O$, $H_2SO_4$, and $HNO_3$, and the solid impurities may be insoluble compounds or salts such as non-diamond, metal oxides, or carbide. Eventually, the UDD fine particle of the present invention comprises 72 to 89.5% of whole carbon, 0.8 to 1.5% of hydrogen, 1.5 to 2.5% of nitrogen, and 10.5 to 25.0% of oxygen (which is compared with a conventional diamond comprising 90 to 99% of whole carbon, 0.5 to 1.5% of hydrogen, 2 to 3% of nitrogen, and less than 10% of oxygen), as elemental composition. Among all forms of carbon contained, 90 to 97% of carbon is in the state of diamond crystal and 10 to 3% of carbon is in the state of non-diamond carbon.

The impurities in the UDD fine particle may theoretically be classified into (i) water soluble (ionized) electrolyte, (ii) hydrolysable and ionic ones, which are chemically combined with a diamond surface, (salt forms of surface functional groups), (iii) water insoluble ones (that is, impurities, insoluble salts and insoluble oxides mechanically disposed on the surface thereof), and (iv) ones trapped inside the crystal lattice of the diamond particle or encapsulated thereinside. The impurities (i) and (ii) are formed in the process of purification of the UDD fine particle. The primary impurities of water soluble electrolyte (i) may be removed by washing the UDD with water. However, an ion-exchange resin may be preferably used for more advanced washing steps.

Almost all the functional groups on the surface of the UDD fine particle of the present invention may be negative groups such as —COOH, —OH, —$SO_3H$, —$NO_3$, and —$NO_2$ groups, but also there exist amino group (which is considered to generate in the neutralization stage). Therefore, the diamond of the present invention is per se considered to be an ion exchange material. Since the aqueous suspension solution of the UDD fine particle is treated with an ion exchange material to have the surface group in the state of non-salt, it is considered to be effective in view of the subsequent process.

The water soluble impurities (iii) may be both of an isolated micro particle comprising metals, metal oxides, metal carbides, and metal salts (sulfates, silicates, and carbonates) and an inseparable surface salts or surface metal oxides. To remove them, i.e. to transfer them into a soluble form, an acid is used according to the present invention.

According to the present invention, up to 40 to 95% of the impurities (I), (ii) and (iii) can be removed by means of various methods, but it is impossible to completely remove those impurities, and also, it is not essential to completely remove them according to the present invention. Those impurities of the UDD do not adversely affect the measurement using the DAN chip of the present invention, the trapping of virus, and the preparation of a vaccine. Apart from the complete removal of the impurities (iii), it is not considered to be practical to remove the impurities (iv) by means of chemical treatment. Basically, elements to form the impurities may include silicon, calcium, iron, sulfur, titanium, copper, chromium, and potassium, which practically are always present in a small quantity. Since the UDD of the present invention, having a highly activated surface, is able to absorb impurities in a solution for removal, it may be useful to such an application. Therefore, a part of the impurities, that is, silicon, potassium and iron, may, on the contrary, decrease the water hardness used in the purification technique of the UDD. Iron is fundamentally one of technological impurities (that is, it is a material applicable to be used in the shock conversion method), and it is difficult to remove it up to a concentration less than 1.0 or 0.5 wt. %. Iron in such a concentration may be there mainly at the surface thereof.

The UDD fine particle of the present invention contains a great number of kind and amount of volatile impurity (as much as 10% by weight). They can be decreased by purification by means of heat treatment under a vacuum condition of 0.01 Pa. The temperature for heating in the process may be set at up to 400° C., and the optimum temperature for heating may be set at up to 250° C.

On the other hand, from a different view point, one of the best scientific discoveries found in the manufacture process for preparing the UDD fine particle of the present invention is to clarify the relationship between the various purification processes, for purifying crude diamond (blended diamonds, BD) artificially obtained by means of explosion of a detonating agent, and the compositions and properties of the resultant UDD.

Prior to present invention, the BD is subjected to various oxidizing systems based on nitric acid, and alternatively, to various non-oxidizing systems based on an organic solvent (that is, hydrocarbon, alcohol), so as to obtain the UDD, whose compositions and properties are summarized in Table 1.

The non-oxidative treatment of the BD with the organic solvent (hydrocarbon $CnH_{2n+2}$, and an alcohol $CnH_{2n+1}OH$) does not affect the carbon skeleton of the UDD particle, but changes surface functional groups resulting in changing the elemental composition of the BD. In other words, as hydrocarbon and alcohol are bonded to and consumed by the UDD, the contents of hydrogen and oxygen are relatively increased. Thus, the total number of the hetero elements (hydrogen, nitrogen, and oxygen) is increased double.

[Manufacture of the UDD]

Method of preparing an improved UDD fine particle used in the present invention comprises the steps of: preparing a initial mixture of a diamond and non-diamond mixture (initial BD) by means of explosion of a detonating agent (shock conversion); subjecting the initial mixture to an oxidation treatment to obtain a suspension solution including the diamond; separating a phase including diamond, wherein after the oxidation treatment, a basic material having per se volatility or to generate a decomposed material having volatility is added, to neutralize with nitric acid, and thereby obtained diamond fine particle has a functional group on the surface thereof.

It is preferable that the oxidation treatment is performed to repeat a step of heating at a temperature of 150 to 250° C. under a pressure of 14 to 25 atoms for a period of at least 10 to 30 minutes several times. Also, it is preferable that the oxidation treatment comprises an oxidative decomposition step by using nitric acid, an oxidative etching step with nitric acid after the oxidative decomposition step, and a neutralization step to decompose nitric acid after the oxidative etching step.

Further, the oxidative etching step is preferably carried out at a higher pressure and a higher temperature than those of the condition for the oxidative decomposition step. Furthermore, the oxidative etching step preferably comprises a primary oxidative etching step and a secondary oxidative etching step, the secondary oxidative etching step being preferably carried out at a higher pressure and a higher temperature than those of the condition for the primary oxidative etching step. While the neutralization step by the basic material produces a suspension solution including the diamond, it is also preferable that the phase including the diamond is obtained by adding water and decanting it, thereby separating the phase including the diamond from the other phase without the diamond.

After the step of decanting with water for separating the phase including the diamond from another phase without the diamond, thereby obtained suspension solution is preferably subjected to washing with nitric acid, to divide it into a lower suspension liquid containing the prepared diamond particles and an upper drain liquid, and then, the lower suspension liquid containing the prepared diamond particles is separated

TABLE 1

| BD-sample<br>Treatment conditions<br>(wt. %) | UDD<br>gross-formula | Relative quantity of heteroatoms on 100 atoms of carbon |
| --- | --- | --- |
| initial, α = 0 | $C_{100}H_{5.3}N_{2.8}O_{4.1}$<br>C: 86.48%, H: 0.81%, N: 2.22%, O: 10.49% | 12.2 |
| treatment with hydrocarbons<br>CnH2n + 2 | $C_{100}H_{13.8}N_{2.9}O_{4.6}$<br>C: 90.36%, H: 1.04%, N: 3.06%, O: 5.56% | 21.3 |
| treatment with alcohols<br>CnH2n + 1OH | $C_{100}H_{15.3}N_{2.6}O_{8.0}$<br>C: 86.96%, H: 1.12%, N: 2.24%, O: 9.28% | 26.1 |

Degree of oxidative decomposition α = [(C″ox in Cox)/Cox] × 100 (Where Cox is total mass for oxidizable carbon in DB or UDD, and C″ox in Cox is the same in an oxidated sample)

from the upper drain liquid. Also, the step of separating the lower suspension liquid containing the prepared diamond particles from the upper drain liquid may preferably comprise a step of leaving the suspension liquid washed with nitric acid as it is for a while.

Moreover, the method may further comprise a step of subjecting the lower suspension liquid containing the prepared diamond particles, to a pH- and concentration-adjustment treatments so as to having a pH value of 1.0 to 7.9, and preferably, of 1.5 to 6.95, and more preferably, of 2 to 6.0, and a diamond fine particle concentration of 0.05 to 16%, and preferably, of 0.1 to 12%, and more preferably, of 1 to 10%.

Accordingly, a favorable method of preparing an improved UDD suspension liquid according to the present invention comprises the steps of: preparing an initial mixture including a diamond and a non-diamond (an initial BD) by explosion of a detonating agent (shock conversion); subjecting the mixture including the diamond and the non-diamond to an oxidative decomposition treatment; subjecting the mixture including the diamond and the non-diamond to an oxidative etching treatment to prepare a nitric acid solution including a UDD fine diamond particle; adding a basic material having per se volatility or to generate a decomposed material having volatility to neutralize by generating a decomposition reaction with nitric acid; decanting the obtained suspension solution with water; washing the decanted suspension solution with nitric acid followed by leaving it as it is to form a lower suspension liquid containing the UDD fine particles and an upper drain liquid; taking out the lower suspension liquid followed by washing it with nitric acid; subjecting the suspension liquid to centrifugal separation; and if necessary, subjecting the suspension liquid to pH- and concentration adjustment treatments to finally prepare an aqueous suspension liquid of the UDD fine particles.

Further, the powder of the UDD fine particle according to the present invention is prepared by subjecting the suspension liquid including the UDD fine particle to centrifugal separation to take the UDD fine particle, followed by drying it at a temperature of 400° C. or less, and preferably at a temperature of 250° C. or less.

Thus, the obtained diamond particle of the present invention is obtained having the following particle properties: (i) The diamond fine particle has an element composition including 72 to 89.5% of whole carbon, 0.8 to 1.5% of hydrogen, 1.5 to 2.5% of nitrogen, and 10.5 to 25.0% of oxygen. (ii) The diamond fine particle has no particle size over 1000 nm or below 30 nm, having a narrow distribution of number average particle diameter (ØMn) of 150 to 650 nm. (iii) The diamond fine particle, when analyzed by an X-ray diffraction (XD) spectrum analysis using Cu,Kα radiation, has the largest peak at a Bragg angle of 43.9°, strong and characteristic peaks at either of Bragg angles of 73.5° and 95°, a significantly biased halo at a Bragg angle of 17°, and essentially no peak at a Bragg angle of 26.5°. (iv) The diamond fine particle has a specific surface area of $1.50 \times 10^5$ m$^2$/kg or more, all of the surface carbon atoms being substantially bonded with hetero atoms, and the diamond fine particle having a total absorption space of 0.5 m$^3$/kg or more.

The UDD fine particle used in the present invention has high hardness and low electric conductivity, which are specific to diamonds. In addition, it is excellent in electromagnetic properties such as low dielectric property and low magnetic sensitivity, good in lubricity, low in thermal conductivity, and excellent in heat resistance, thermal expansion resistance, peel-off resistance, water and chemical resistances. It is also excellent in dispersion property, which is specific to a super fine particle having a narrow particle size distribution. It is also excellent in surface activity, and ion or cation exchange property, and good in compatibility with metal material and ceramics, and is proved to be safety as a chemical agent. Furthermore, the UDD fine particle of the present invention generally has a crystal shape specific to diamonds in a cubic form. In other words, the UDD fine particle of the present invention generally does not have a twin-crystal having a shape of rectangular or striped flattened form. Also, the UDD particles of the present invention has in fact a porous active surface having a round shape due to the oxidative decomposing treatment and the oxidative etching treatment subjected to the BD.

The UDD fine particle is colorless and transparent. When it is mixed with another material, it is dispersed uniformly therein, thus being very difficult to visually observe the appearance of such mixed material by naked eyes. Also, the UDD fine particle of the present invention, when it is dispersed into a solid composition, can not be visually observed by naked eyes.

Thus, this UDD fine particle can be used, in addition to the description of the present invention, in the field of molds for parts of automobile and motorcycle, equipment materials for aircraft and space industry, elements and parts for chemical plant, computer and electronics, and optical elements and parts for office automation (OA) and camera, and recording medias such as magnetic tape and compact disc. It may be added to improve, for example, slidability, lubricity, abrasive resistance, heat resistance, thermal expansion resistance, peel-off resistance, water and chemical resistances, gas-corrosive resistance, appearance, touch feeling, color tone, specific gravity, and density. For such purpose, the UDD fine particle of the present invention may be added to lubricant oil composition, fuel composition, paste composition such as greasy, resin composition for molding, rubber composition, metallic composition, ceramics composition and so on. The UDD fine particle of the present invention may be applied to a sliding portion of a mechanical equipment in the form of powder. The UDD fine particle of the present invention may be used as an absorption material and ion exchange material. However, the best benefit of the present invention is expected where the UDD fine particle is used in the condition of suspension solution, especially, aqueous suspension solution, to show its good dispersiblity.

More specifically, an aqueous suspension solution including the UDD fine particle of the present invention in an amount of 15.5% (Volume: 1100 g, the content of the UDD: 170 g), the UDD fine particle comprising 98.22% of carbon, 0.93% of oxidizable residual carbon in the oxidative purification treatment, 0.85% of incombustible residue, based on a dried powder, has a warrantee of durability of 24 months as a commercial product.

An aqueous suspension solution including the UDD fine particle of the present invention in an amount of 12.5% (Volume: 2010 g, the content of the UDD: 251 g), the UDD fine particle comprising 98.40% of carbon, 0.85% of oxidizable residual carbon in the oxidative purification treatment, 0.75% of incombustible residue, based on a dried powder, has also a warrantee of durability of 24 months as a commercial product.

An aqueous suspension solution including the UDD fine particle of the present invention in an amount of 11.0% (Volume: 552 g, the content of the UDD: 56 g), the UDD fine particle comprising 98.87% of carbon, 0.73% of oxidizable residual carbon in the oxidative purification treatment, 0.4% of incombustible residue, based on a dried powder, has also a warrantee of durability of 24 months as a commercial product.

An aqueous suspension solution including the UDD fine particle of the present invention in an amount of 11.5% (Volume: 1044 g, the content of the UDD: 120 g), the UDD fine particle comprising 98.8% of carbon, 0.8% of oxidizable residual carbon in the oxidative purification treatment, 0.4% of incombustible residue based on a dried powder, has also a warrantee of durability of 24 months as a commercial product.

It is noted that such durability is preferably warranted in the case where the product is stored at a temperature lower than 0° C. It is necessary to prepare a specific equipment in addition to a specific consideration to store the suspension solution of the present invention for an extreme extended period at a temperature lower than 0° C. Therefore, it is better to inform a customer, who purchases the suspension solution for stocking the product for unscheduled use, of such instructions.

The UDD fine particle of the present invention, in the form of a suspension liquid at a concentration as high as 16%, does not aggregate and precipitate during storage for six months at room temperature (15 to 25° C.). In general, any aqueous composition is degraded at double rate, as the storage temperature is raised by 10° C. For example, since almost all of the metal plating process are carried out under a condition of an elevated temperature, the aqueous suspension liquid of UDD fine particle of the present invention, having a resistance to high temperature as above mentioned, may be a good advantage. However, it is preferable to store the aqueous suspension liquid of UDD fine particle, usually at a temperature of −15° C. to 10° C.

Since the UDD fine particle of the present invention has various carboxyl groups on the surface, it is improved in dispersion stability and activity as described above. The behavior of the UDD fine particle is similar to that of n-type semiconductors. The UDD fine particle exhibits to be weak acid, showing a slightly low electric conductivity. The UDD fine particle may be durable for the using under an elevated temperature as high as 60 or 70° C., but it is preferable to avoid the using in the condition over such temperature. The aqueous suspension liquid of the UDD fine particle of the present invention is, in general, adjusted to a pH value of 4.0 to 10.0, and preferably of 5.0 to 8.0, and more preferably of 6.0 to 7.5. If its pH value exceeds 10, the suspension liquid is apt to be unstable.

In order to improve dispersion property, it is generally to use a surfactant. However, according to the present invention, surfactant is not necessary to be added in preparing an aqueous suspension solution of the UDD fine particle. The addition of a surfactant may maintain its dispersion property, but in many cases, the addition of a surfactant will decrease the dispersion property of the aqueous solution of the UDD fine particle of the present invention.

The UDD fine particle of the present invention has a large amount of negative charge functional groups formed on the surface thereof, and thus, it is excellent in surface activity and the affinity. Also, since the UDD fine particle does not include ones having a large particle size, resulting in a narrow particle size distribution. Therefore, the UDD fine particle of the present invention can hardly be aggregated and precipitated, which is unlike the conventional super fine particles of diamond. The UDD fine particle of the present invention may produce an aqueous suspension solution in which it is dispersed in a stable state. As described before, when the suspension liquid of the UDD fine particle is aqueous, the addition of a surfactant agent is not essential, and rather, it may decrease its dispersion stability. It is considered that such decrease of stability may occur by the following reason:

Namely, the conventional UDD fine particle includes a cationic surfactant agent added. However, if the suspension solution of the present invention includes include it, the cationic portion in the surfactant agent tends to be drawn to the negative charge functional groups on the surface of the UDD fine particle. As a result, each hydrophobic long-chain hydrocarbon group of surfactant agent is oriented with facing to the outside of thereof, resulting in being lacking in hydrophilic property.

[Resin Composition]

The resin may improve its property by adding the UDD fine particle of the present invention. Following is an example of the case.

For example, method by means of cold curing and impregnation of the UDD fine particle into a fluorine elastomer may give the following properties: (i) The permeability of hydrocarbon or polar solvent is decreased by one fiftieth (1/50), namely from $1.389 \times 10^{-7}$ kg/m$^2$ sec to $0.0278 \times 10^{-7}$ kg/m$^2$ sec.

Also, under an alkaline or acid condition including a salt, ethylene/perfluoro alkylvinyl ether copolymer (protective membrane), in which the UDD fine particle of the present invention is added, shows an extreme high chemical resistance. (ii) Its dry friction coefficient of the metal is decreased to 0.01 or lower. (iii) Its durability of copolymer elastomer is improved, to the extent that the elastomer of ethylene/perfluoro-alkyl vinyl ether copolymer, subjected to 100% stretching, has a tension stress factor and a bursting strength 10 times as large as the original values. That is, its tension stress factor is increased from 8.5 MPa to 92 MPa, and its bursting strength is increased from 15.7 MPa to 173 MPa. Simultaneously, relative tensile elongation is also increased by 1.6 times, namely, from 280% to 480%. However, its relative tensile elongation ratio is decreased by 1/1.2, namely, from 108% to 81%. (iv) Its bonding strength of an adhesive is increased. More specifically, the improvements are as follows: (a) With respect to the active surface, its bonding strength to steel (CT grade) is increased from 1.7 kN to 5.1 kN, and its bonding strength to aluminum is increased from 0.5 kN to 3.3 kN, namely, by about 300 to 500 times. Also, its bonding strength to zinc is increased in a similar level. (b) With respect to the inert surface, its bonding strength to lead or copper is increased from 2.8 kN to 3.3 kN. (c) Various film samples have a dielectric loss tangent of 2.58 to 2.71 at 4000 Hz as depending on the thickness, and a penetration factor of up to 15 and a reflection factor of as high as 12.4, at 5000 MHz, and a penetration factor of as high as 14.3 and a reflection factor of as high as 12.4 at 11000 MHz.

Thus, the film including the UDD fine particle of the present invention is improved in its physical and mechanical properties, to make possible to perform it under a pressure load of $2 \times 10^6$ kg/m$^2$. Also, the improvements are as follows: (d) A film, in which a polysiloxane is modified by the UDD fine particle of the present invention, has improved durability of such polysiloxane elastomer. In case of 100% stretched polysiloxane elastomer, its tensile stress improves from 19 MPa to 53 MPa, namely, by 3 times, and its tensile-bursting strength improves from 52 MPa to 154 MPa, namely, by 3 times. (e) A fluorine rubber material containing the UDD fine particle of the present invention has elasticity resistance and thermal aging resistance. That is, 100% stretched fluorine rubber material increases a stress of from 7.9 MPa to 12.5 Mpa, namely, by 1.6 times, and a tensile-bursting strength from 210 MPa to 285 MPa, namely, by 1.35 times. In addition, the film of fluorine elastomer containing the UDD fine particle of the present invention increases a friction aging resistance from 1.5 to 2. Also, a film of polyisoprene is significantly improved in the similar manner of such increases. Further, a film of fluorine rubber containing the UDD fine particle of the present invention, even after it is subjected to heating for aging, has physical and mechanical properties in the same or slightly better level of those of a usual fluorinate rubber which is not subjected to heating. In the course of heating for aging, the UDD fine particle of the present invention hardly generate any structural breakdown, and rather, it functions to prevent it. As described above, the fluorine rubber containing the UDD fine particle of the present invention has improved properties of elastomer.

When the fluorine rubber is stretched by 300%, it has a stress increased from 7.7 MPa to 12.3 Mpa, namely, by 1.4 times, and a tensile bursting strength increased from 139 MPa to 148 MPa. The maximum swelling degree of the fluorine rubber in toluene is decreased into 45% of the original. As described, the fluorine rubber is high in hardness and durability (about 30% higher than any conventional one), and resistant to mechanical fatigue. The increase of the stretching rate by enhancing durability is not considered under the known theories, since it shows a change of the molecular structure of the fluorine rubber. This is proved by the fact that the adhesiveness is increased from 1.7 MPa to 2.7 MPa, namely, by 1.6 times.

The change of the rubber in its property by means of the UDD fine particle of the present invention may improve all the properties in consideration (that is, a stress at stretching by 300%, bursting strength, and tensile strength), increasing by 1.6 to 1.8 times, without changing its elasticity. The rubber containing the UDD fine particle of the present invention is high in hardness than any conventional rubbers without the UDD fine particle of the present invention (wherein it is increased from 5.8 MPa to 7.4 MPa at stretching by 300%, and the stretching rate is decreased from 700% to 610%). When the rubber is added with both the UDD fine particle of the present invention and an artificial carbon powder, its tensile strength will be increased by 25 to 35% than that of a typical sample.

When the UDD fine particle of the present invention is mixed with a common rubber mixture based on a butadiene (70 mol)-styrene (30 mol) copolymer, its adhesiveness is increased from 1.6 MPa to 3.1 MPa, namely, 1.5 to 2.0 times, as compared with a typical sample. The copolymer rubber containing the UDD fine particle of the present invention has a durability in the similar level to a typical sample, and is higher in hardness than the typical sample. The copolymer rubber containing the UDD fine particle of the present invention has a tensile strength increased 71 kN to 135 kN, namely, by 2 times, approximately, and a stress at stretching by 300% increased 7.9 MPa to 11.4 MPa, namely, by 1.44, approximately.

The film of butadiene nitrile rubber B14 modified by the UDD fine particle of the present invention shows a decreased friction coefficient by 1.5 times, an increased durability in fatigue by 1.4 times, an increased elasticity by 1.7 times, and an improved frost resistance (with decreasing its glass transition temperature by 8 to 10%).

A natural rubber (RSS made in Malaysia) modified by the UDD fine particle of the present invention shows an increased stress at stretching by 300% from 1.8 MPa to 5.4 MPa, namely, by 3 times, approximately, accompanying with the increasing of a friction coefficient and fatigue resistance. An epoxy adhesive agent containing the UDD fine particle of the present invention is also improved significantly in viscosity and bonding strength.

The UDD fine particle of the present invention can preferably be used for various polymerizing processes including solution polymerization, suspension polymerization, copolymerization, chemical curing, electron curing, gas flame heat-up curing, and electrostatic paint curing. The polymer composition containing the UDD fine particle of the present invention is favorable in: (i) improvements in strength, weather resistance, and the wear resistance; (ii) a lowered friction coefficient of polyfluoro elastic material and perfluoro polymer, and an increased friction coefficient of polyisoprene; (iii) improvements in quality and commercial value, for example, application to a material and coating used for microfabrication technologies products. Generally, the UDD fine particle of the present invention is preferably used in an amount of 1 to 5 kg per 1000 kg of a polymer or rubber, and in an amount of 1 to 5 kg per 1000 $m^2$ of a film or coating.

DETAILED DESCRIPTION FOR THE METHOD FOR PRODUCING THE UDD

The method for preparing the method for producing the UDD fine particle of the present invention is described in more detail with reference to the drawings.

Figure 1:
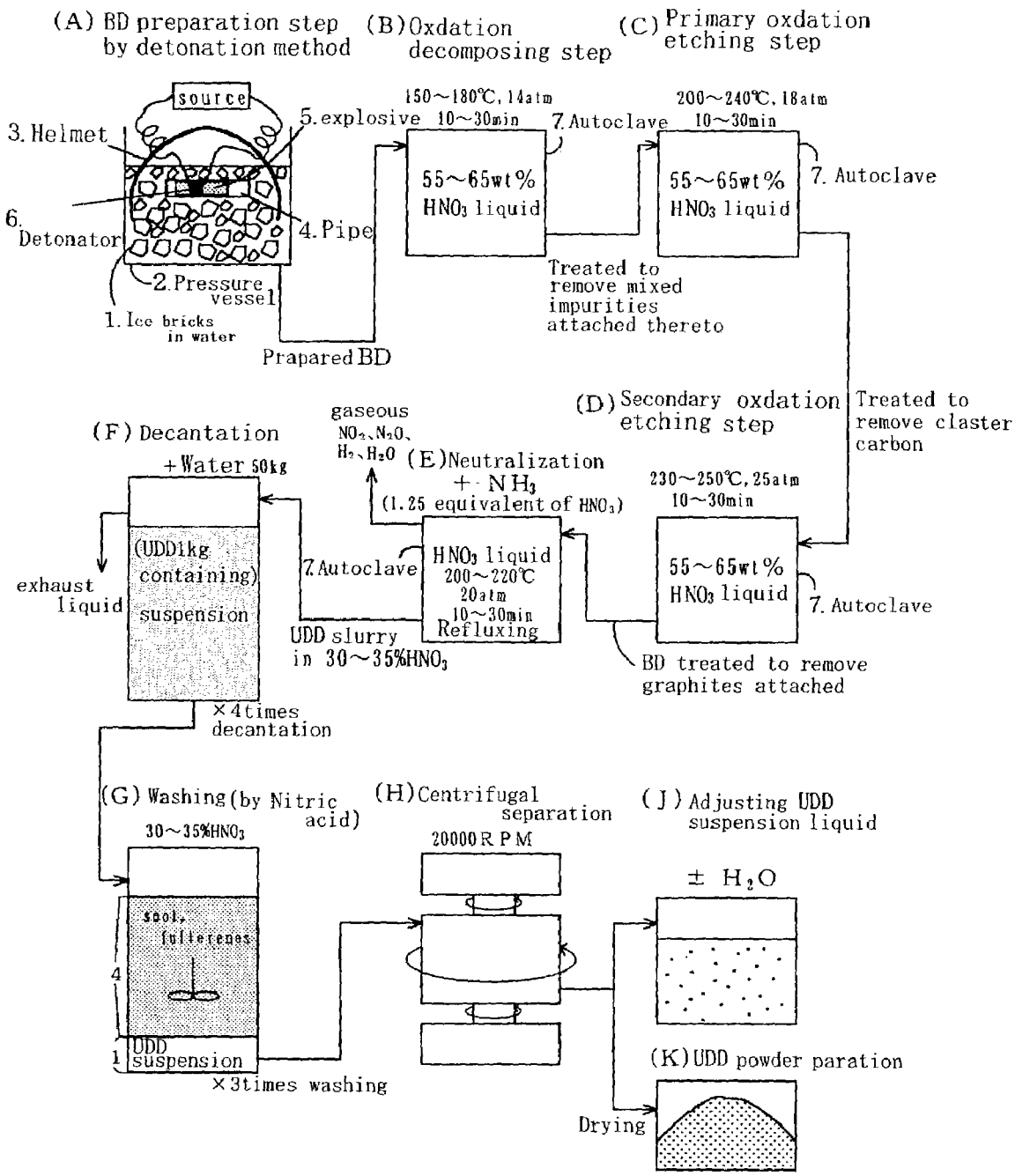
FIG. 1 is a conceptual diagram showing a method to synthesize the UDD fine particle and a method to prepare the suspension liquid suspending the UDD fine particle, according to the present invention.

FIG. 1 is a schematic diagram showing a procedure of producing an improved UDD fine particle of the present invention. In the method as shown as an example, the method of producing the UDD fine particle of the present invention comprises the steps of: (A) preparing an initial BD by means of explosion of a detonating agent (shock conversion process); (B) collecting thereby obtained initial BD, followed by subjecting it to an oxidative decomposition for eliminating contaminants such as carbons; (C) subjecting the obtained initial BD purified by the oxidative decomposition to a primary oxidative etching treatment for removing hard carbon mainly covering the surface of the BD; (D) subjecting the BD after the primary oxidative etching treatment to a secondary oxidative etching treatment for removing hard carbon existing in ion-permeable gaps between the UDD particles composing of the BD aggregation body or at crystalline defects; (E) to a nitric acid solution including the BD subjected to the secondary oxidative etching treatment, adding a basic material for strong neutralization reaction, wherein the basic material is per se volatile or to generate a decomposed material having volatility, so as to generate a decomposition reaction involving a small explosion to divide a secondary aggregation body aggregating the UDD fine particles into a primary aggregation body separating respective UDD fine particle; (F) sufficiently decanting with water the UDD suspension liquid produced by the neutralization; (G) washing with nitric acid, and then, trapping the decanted UDD suspension liquid in a static state to deposit and separate a lower suspension layer located underside including the UDD fine particle from an upper drain layer portion; (H) subjecting the washed UDD suspension liquid to centrifugal separation; (J) preparing a purified UDD suspension aqueous solution at a specific pH and concentration subjected to the centrifugal separated UDD suspension; and (K) subjecting the centrifuged UDD to drying at a temperature of 250° C. or less, and preferably at a temperature of 130° C. or less, so as to obtain a powder of the UDD fine particle. The UDD aqueous suspension solution of the present invention after the step (J) has a pH value of 1.0 to 7.9, and preferably of 1.5 to 6.95, and more preferably of 2.0 to 6.0.

In the step (A) of preparing the initial BD by explosion method (shock conversion process), a puretitanium vessel (2) of pressure resistance filled with water and a large amount of ice bricks are prepared to provide with an explosive agent (5) with an electric detonator (6) (in the example, that is TNT (tri-nitro-toluene)/HMX (cyclo-tetra-methylene-tetra-nitramine at 50/50), inside the body of the vessel, placing horizontally a steel pipe (4) having a plug at one side for containing an explosive agent (5), covering a steel helmet (3), followed by being detonated, and then taking up a product, namely, the initial BD, from the water containing ice bricks in the vessel (2).

Here, the temperature in the step for preparing the BD is important. As the BD prepared under a cooled condition tends to decrease the density of structure defects to be bonded with oxygen containing functional groups as active sites or absorption sources, the use of ice is preferably limited or avoided if possible.

The obtained BD (initial BD) is subjected to an oxidative decomposition step (B) where it is dispersed into a $HNO_3$ solution at a concentration of 55 to 56% by weight in an autoclave at a temperature of 150 to 180° C., for subjecting an oxidative decomposition at a pressure of 14 atoms for a period of 10 to 30 minutes, so as to decompose carbon and other inorganic contaminants. After the oxidative decomposition step (B), the BD is subjected to a primary oxidative etching step (C). The condition in the primary oxidative etching step (C) is crueler, setting to be at a temperature of 200 to 240° C. under a pressure of 18 atoms to remove hard carbon deposited on the surface of the BD.

Next, the obtained BD is followed by a secondary oxidative etching step (D). This secondary oxidative etching step is intended to remove small amounts of hard carbon existing in an ion-permeable interface gap formed between the UDD fine particles of BD aggregation body, or at the crystalline defects of the surface of the UDD fine particle. The condition for the treatment is crueler, namely, at a temperature of 230 to 250° C. under 25 atoms. According to the present invention, the treatment is not limited to perform under the conditions at a temperature of 150 to 180° C. under 14 atoms, at a temperature of 200 to 240° C. under 18 atoms, and at a temperature of 230 to 250° C. under 25 atoms, but it is preferable at least to have the condition gradually set to be crueler. After the secondary oxidative etching step (D), the solution has a pH value of 2 to 6.95.

The neutralizing step (E) is a unique feature of the present invention, that is, such step is distinct from any conventional methods. In the step of neutralizing step, the addition of a basic material to generate a volatile decomposition product may increase the pH value from a range of 2 to 6.95 to a higher range of 7.05 to 12. In the neutralizing step (E), the nitric acid solution containing the BD product after the secondary oxidative etching is mixed with a basic material, which is per se volatile or generates a decomposed material having volatility, so as to neutralize it. In the neutralizing step, nitric acid remaining in the BD in the nitric acid aqueous suspension solution, and a cation generally having an ion radius smaller than that of an anion permeates to attack, so as to generate a neutralization reaction, decomposition reaction, impurity removal solution reaction, gas generation reaction, and surface functional group generating reaction, involving a small explosion among the reaction couple, resulting in increasing the temperature and pressure of the system. As a result, the BD aggregation body is divided into respective UDD fine particle. Also, the neutralization reaction step (E) involves a small explosion to form a large specific surface area and a porous space for absorption of the UDD fine particle of the present invention.

The basic material may include: hydradine, methyl amine, dimethyl amine, trimethyl amine, ethyl amine, diethyl amine, triethyl amine, ethanol amine, propyl amine, isopropyl amine, dipropyl amine, aryl amine, aniline, N,N-dimethyl aniline, diisopropyl amine, poly-alkylene poly-amine such as diethylene triamine and tetraethylene pentamine, 2-ethylhexyl amine, cyclohexyl amine, piperydine, folmamide, N,N-methyl folmamide, and urea. For example, when the basic material is ammonium, the reactions occur with an acid as follow:

$HNO_3 + NH_3 \rightarrow NH_4NO_3 \rightarrow N_2O + 2H_2O$

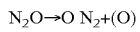

$N_2O \rightarrow O\ N_2 + (O)$ $$3HNO_3 + NH_3 \rightarrow NH_4NO_2 \rightarrow N_2O_3 + H_2O + O_2 + (O)$$

$$NH_4NO_2 \rightarrow N_2 + 2H_2O$$

$$N_2O_3 + NH_3 \rightarrow 2N_2 + 3H_2O$$

$$N_2O_3 \rightarrow N_2 + O_2 + (O)$$

$$NH_4NO_2 + 2NH_3 \rightarrow 2N_2 + H_2O + 3H_2$$

$$H_2 + (O) \rightarrow H_2O$$

$$HCl + NaOH \rightarrow Na^+ + Cl^- + H_2O$$

$$HCl + NH_3 \rightarrow NH_4^+ + Cl^-$$

$$NH_4^+ \rightarrow NH_3 + H^+$$

$$H_2SO_4 + 2NH_3 \rightarrow N_2O + SO_2 + NO_2$$

Various gases such as $N_2$, $O_2$, $N_2O$, $H_2O$, $H_2$, and $SO_2$ are generated from the above reactions, and such gases are discharged to the outside of the system. Therefore, the system is less affected by the resultant residues.

In the decanting step (F) after the neutralizing step, a step of the decanting of the UDD suspension with water is repeated for a specific times (for example, three times or more). In the washing step (G) after the decanting step, the decanted UDD suspension is stirred with nitric acid added (using a mechanical magnetic stirrer, in this example), to wash it, followed by leaving it as it is to form a lower layer of the UDD suspension solution and an upper drain layer. The lower layer of the UDD suspension solution is drawn to collect. The lower suspension solution containing the UDD fine particle is separated, from the upper drain layer. In a case, for example, where 50 kg of water is added into 1 kg of suspension solution containing the UDD fine particle, the interface between the upper drain layer and the lower suspension solution may be unclear, but the volume of the lower suspension solution containing the UDD fine particle is about one fourth of the volume of the upper drain liquid. While the upper drain liquid contains very fine particles of diamond having a particle size of 1.2 to 2.0 nm, it may be possible that such particles aggregates together with impurities, and these aggregations are impossible to be crushed by mechanical forces. Therefore, according to the present invention, such aggregations of very fine diamond particles are not necessary to be collected.

The UDD suspension liquid taken from the bottom of the vessel is subjected to a centrifugal separating step (H), which is conducted by a high-speed centrifugal separator at a rate of 20000 rpm. If necessary, the UDD suspension liquid after the step (J) of the adjusting of the UDD suspension aqueous solution may be subjected to a drying step (K) to prepare a power of the UDD fine particle. The UDD fine particle prepared by the method of the present invention has a very narrow range of particle distribution either in a suspended form or powder form. As a result of measurements, it is found that the UDD fine particle does not include ones having a particle diameter having 1000 nm or more, (which is distinct from a conventional UDD particle including one having a particle diameter of 1000 nm or more, at a concentration of 15% or more), nor ones having a particle diameter of 30 nm or less. The UDD fine particle of the present invention has a volumetric average particle diameter of 150 to 650 nm, typically having a narrow distribution of particle diameter of 300 to 500 nm. Such UDD fine particle can be crushed, for example, by subjecting it to a mechanical shearing action.

The UDD fine particle of the present invention has a specific density of $3.2 \times 10^3$ to $3.40 \times 10^3$ kg/m$^3$. Specific density of amorphous carbon is $(1.8 \text{ to } 2.1) \times 10^3$ kg/m$^3$ and a specific density of graphite is $2.26 \times 10^3$ kg/m$^3$, and a specific density of natural diamond is $3.51 \times 10^3$ kg/m$^3$, and further, an artificial diamond synthesized by static conversion technique (not shock conversion) have a specific density of 3.47 to 3.50. Accordingly, the UDD fine particle of the present invention has a specific density smaller than those of the specific densities of natural diamond and a synthetic diamond prepared by static conversion method.

On the other hand, the UDD suspension liquid of the present invention is prepared by adjusting to have a pH value of 1.0 to 7.9, and preferably of 1.5 to 6.95, and more preferably of 2 to 6. It has a volumetric average particle diameter of the UDD fine particle, suspending in the liquid, of 50 nm±25 nm, mostly having a particle diameter of 10 to 100 nm (at a concentration by number average of 80% or more, and at a concentration by weight average of 70% or more), having a narrow particle distribution. The suspension liquid may include the UDD fine particle at a concentration of 0.05 to 16%, and preferably of 0.1 to 12%, and more preferably of 1 to 10%. If the suspension liquid has a concentration exceeding 16%, the storage stability of the suspension liquid may be adversely affected.

In FIG. 1, the steps (B), (C) and (D) are illustrated as if these steps are carried out in discontinuous systems using different vessels or facilities. However, these steps, of course, may be carried out continuously in the same system of the same one vessel or facility. In similar manner, the steps (F) and (G) may be carried out either in discontinuous systems or the same system. The vessel used may be a pressure vessel.

Figure 2:
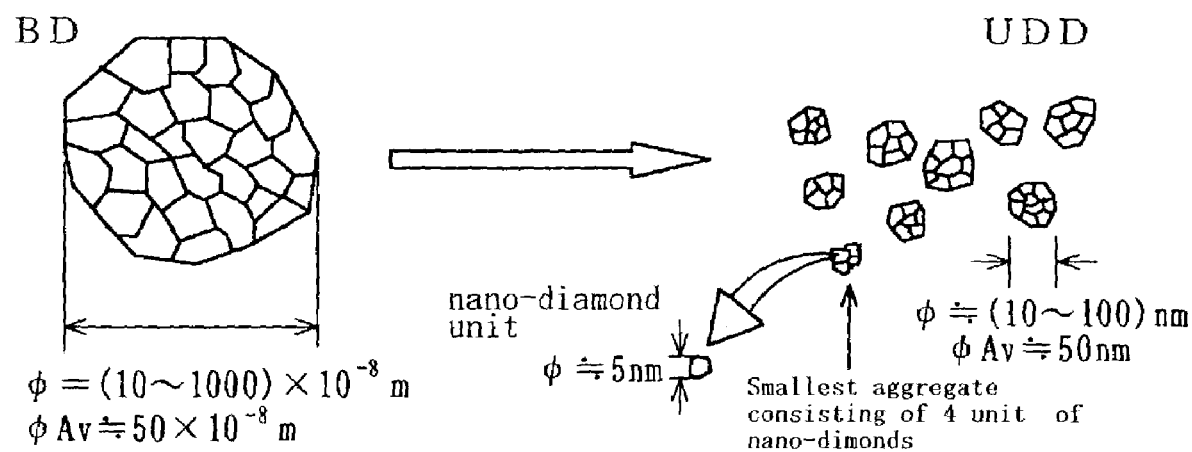
FIG. 2 is a view illustrating a step to form the UDD fine particle of the present invention.

As illustrated in FIG. 2, the step shown in FIG. 1 is subjected to the initial BD having a particle diameter of (10 to 1000)×10$^{-8}$ to obtain a purified UDD fine particle, composed of a number of solid aggregations, each comprising a diamond aggregation of at least four pieces, and generally, ten to several hundreds pieces, in a size of nanometer order. Thereby obtained UDD fine particle has an average particle diameter of 4.2±2 nm, mainly having a particle diameter of 10 to 100 nm, having a narrow particle distribution, having a gravimetric average particle diameter of about 50 nm. The resultant UDD fine particle has a high content of other hetero atoms (hydrogen and oxygen) than nitrogen, having a large specific surface area. Also, since it has a large porous area in the porous portions, the UDD fine particle of the present invention has its surface of extreme high activity, resulting in a very good dispersion property. The yield of the purified UDD (based on the amount of a detonating agent used) is between 1% and 5%, usually.

[The Property of the Samples of the UDD Fine Particle]

Next, the result of the measurement is shown as to various properties with respect to the UDD fine particle and its suspension liquid prepared by the present invention.

EXAMPLE 1

Elemental Analysis

With respect to the UDD fine particle prepared by the method of the present invention as shown in FIG. 1, the results of elemental analysis are shown, which depends on the degree of oxidative decomposition treatment and oxidative etching treatment. The result is based on 100 carbon atoms by calculations.

TABLE 2

The element composition of BD

| Treatment conditions initial BD (wt. %) | Sample No. | Gross-formula | Relative quantity of heteroatoms on 100 atoms of carbon |
|---|---|---|---|
| initial, $\alpha = 0$ (Comparative Example 1) | 1 | $C_{100}H_{5.3}N_{2.8}O_{4.1}$<br>C: 86.48%, H: 0.81%, N: 2.22%, O: 10.49% | 12.2 |
| $\alpha = 26.3\%$ (Comparative Example 2) | 2 | $C_{100}H_{25.4}N_{2.9}O_{22.5}$<br>C: 73.80%, H: 1.56%, N: 2.50%, O: 22.14% | 50.8 |
| $\alpha = 31.8\%$ (Comparative Example 3) | 3 | $C_{100}H_{34.9}N_{2.9}O_{23.1}$<br>C: 72.94%, H: 2.12%, N: 2.47%, O: 22.47% | 60.9 |
| $\alpha = 55.0\%$ | 4 | $C_{100}H_{11.2}N_{2.2}O_{9.1}$<br>C: 86.48%, H: 0.81%, N: 2.22%, O: 10.49% | 22.5 |
| $\alpha = 64.9\%$ | 5 | $C_{100}H_{19.3}N_{2.1}O_{23.5}$<br>C: 73.86%, H: 1.19%, N: 1.18%, O: 23.14% | 44.9 |
| $\alpha = 74.4\%$ | 6 | $C_{100}H_{18.7}N_{2.0}O_{22.8}$<br>C: 74.46%, H: 1.16%, N: 1.74%, O: 22.64% | 43.5 |
| $\alpha = 75.5$ | 7 | $C_{100}H_{23.7}N_{2.4}O_{22.9}$<br>C: 73.91%, H: 1.46%, N: 2.07%, O: 22.57% | 48.8 |

In the Table 2, the degree of oxidization α is identical to that described before.

The result of the analysis exhibits important and, interesting technical discoveries. Namely, oxidative decomposition materials of the BD have various contents of carbon and hetero atoms. From the result in FIG. 2, it is found that the content of hetero atoms in the BD and UDD do not have a linier proportion relationship with their treatment condition (oxidation degree α). Also, from the results in FIG. 1 and FIG. 2, the contents of hydrogen atom as a hetero atom in the BD or UDD are 5 to 35 atoms per 100 atoms of carbon. The contents of oxygen are also 4 to 32 atoms per 100 atoms of carbon. However, the contents of nitrogen are 2 to 4 atoms per 100 atoms of carbon, showing no significant changes depending on the treatment condition (oxidation degree α).

As being omitted to show in FIG. 2, it is considered that the generation of carbon dioxide gas is closely relating to the condition of the surface of the BD. Therefore, a test was made to confirm that the variations of treatment condition, such as the raising of temperature and the raising of acid concentration, gradually increase the ratio of the changing of carbon atoms in the BD into carbon dioxide gas.

In the oxidative etching step of the present invention, amorphous carbon having a disturbance structure is first of all oxidized, and then, carbon of micro-graphite structure is oxidized. In other words, initial BD including a non-diamond form of carbon may be changed into a purified product to have a chemically less active material.

However, in the process for producing the UDD fine particle of the present invention, the condition under a specific oxidative etching for an extended period of time may decompose a part of the diamond material. Degree of the oxidative etching step according to the present invention is limited to up to 45%, approximately, of the UDD, or up to 76.5% of the initial BD.

EXAMPLE 2

Figure 6:
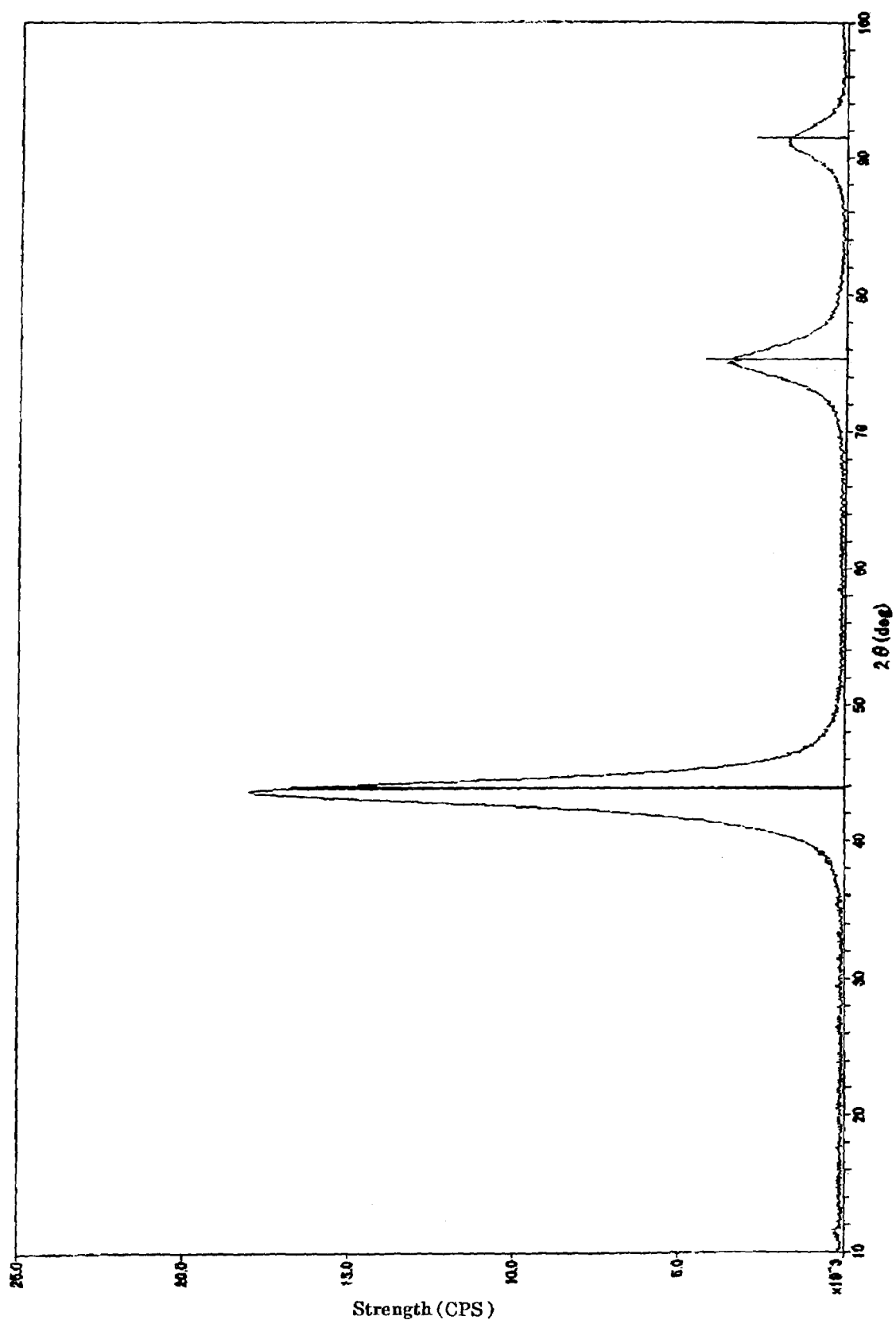
FIG. 6 is an X-ray diffraction chart with respect to in detail an example of a powder of the UDD fine particle of the present invention.

Similar processes as that of oxidizing steps described in Example 1 were conducted using same initial BD, to prepare 12 samples having various degrees of oxidization, as shown in FIG. 6.

Figure 3:
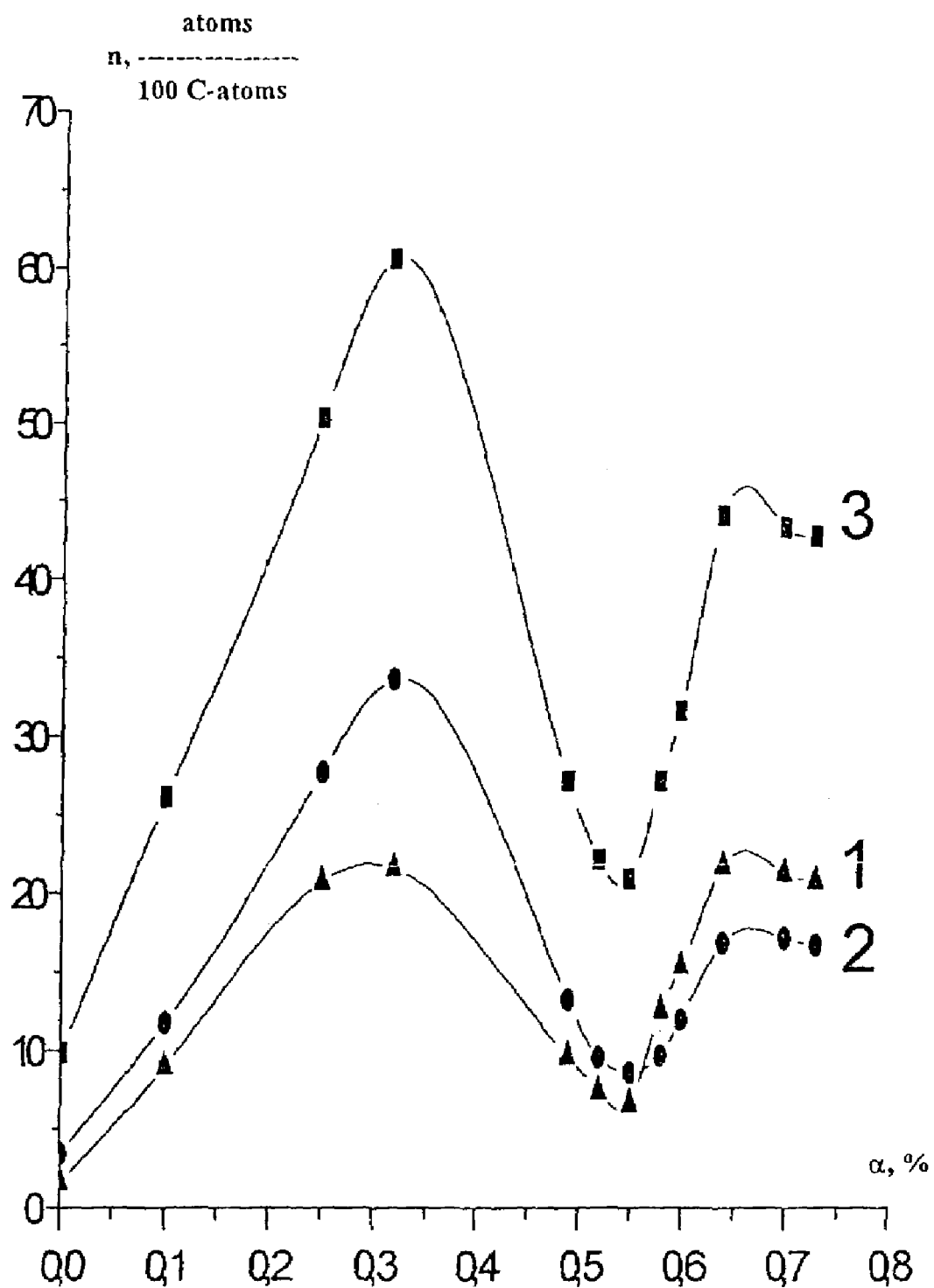
FIG. 3 is a diagram showing the relationship between the degree of oxidization and the elemental composition of the UDD fine particle of the present invention.

As being apparent from a graphic diagram of FIG. 3, the relationship between degrees of oxidative decomposition and etching and compositions of finished BD is not simple. In other words, the BD composition does not depend proportionally on the degree of oxidization. Content of hetero atoms for 100 carbon atoms in the initial BD was minimum, and content of hetero atoms for 100 carbon atoms in partially oxidized BD (at a=26 to 31%) was 53.5, while content of hetero atoms for 100 carbon atoms in partially oxidatively etched BD (at a=65 to 75%) is 4.9. As the oxidization was proceeded on, content of hydrogen and oxygen atoms was varied, and thus chemical constituent of surface functional groups was approaching to a certain magnitude.

As to metastable structures such as partially oxidized BD or partially etched UDD, the activity thereof may be increased by relaxing or softening the hard surface by a reaction media, to form maximum numbers of hetero bonding. More stable structure form in a manner such as the BD or UDD of the present invention contains a minimum hetero atoms. The activity thereof is however much higher than that of conventional fine particles of diamonds synthesized by static conversion, $C_{100}H_{1.1}O_{2.2}$, or soot $C_{100}H_{5.1}O_{4.1}$.

From a chemical point of view on the results as illustrated above, the oxidative decomposition step including the changing of phases is interpreted as follows: 1) primary etching of carbon matrix by structure defects and inter-particle bonds are first of all occurred, and then, an increase of the reaction surface and its saturation with semi-products of oxidation occurs; and 2) etching of loosed surface, gasification and removing of oxidation products. Character of change of these phases show that a non-uniform material by structure is subjected to decomposition, and an effect of oxidant is selective to different structural forms.

The BD or UDD of the present invention has such high contents of hetero atom, implying to have a biased bond property of carbon. As a resulted calculation of measured, each diamond particle having about $4 \times 10^{-9}$ m diameter comprises maximum $12 \times 10^3$ carbon atoms, and $3 \times 10^3$ atoms of them are surface ones. Accordingly, the composition of the UDD of the present invention is expressed by Formula bellow Table 3.

TABLE 3

| Internal atoms | Surface atoms |
|---|---|
| $C_{75}$ | $C_{25}H_{11.2}N_{2.8}O_{9.1}$ |

The other examples omitting to describe here also have similar compositions.

As being apparent from above mentioned aspects, it is concluded that substantially all of the surface carbon atoms of the UDD fine particle of the present invention are bonded with hetero atoms. Expression of "Substantially all of surface carbon atoms are bonded to hetero atoms" used in this specification means such condition as described here.

It is understood from the result of the studies for the concentration of active hydrogen $H_{act}$ at the surface of the UDD of the present invention that hydrogen atoms are active when they are bonded with any other atoms than the carbon atoms. The active hydrogen atoms $H_{act}$ at the surface may be identified as ones which are provided in possible functional group such as hydroxyl, carbonyl, amino, and sulfone groups.

With regard to the interactions between the functional group at the UDD surface of the present invention and methyl magnesium iodide under the presence of anisole, symbolic interactions in three processes, namely interactions (1) between impurity molecules and the outer surface functional group (which is easier accessible functional group) and the impurity molecules, (2) between the porous surface and the same; and (3) between the free surface by mechanical fracturing of UDD aggregates, were picked out.

Depending on the treatment for the BD and UDD, the UDD fine particle may have a protogenic functional group at a concentration of 0.34 to 2.52 micro kg equivalent weight per square meter, and an activated hydrogen at a concentration of 0.49 to 7.52 micro kg equivalent weight per square meter. Therefore, the UDD and the BD may have a hydrogen atom capable of being free, existing on the surface thereof, at an amount of 4 to 22% of the total amount of hydrogen atoms contained in the UDD particle.

Onto surfaces of the UDD particles in the present invention, various kind of oxygen-containing functional groups are provided to determine a dispersion concentration of the particles in aqueous liquids, an amount of electric charges influencing to pH values of the liquids, concentration of phonon electrolytes used, an affinity of the particles for other surfaces, and a specific absorption depending on a degree of dissociation of surface group having acid properties. The specific absorption by the effects of decomposition and etching of the carbon material is changed discontinuously and extremely.

The low specific absorption of the initial BD indicates that the BD was prepared in non-oxidative medium, therefore only small amount of the oxygen-containing groups are positioned on the BD surface. In the present invention, by the result of two steps in which the BD was exposed to different oxidizers, the surface of BD was saturated with the oxygen-contained groups and carbon components were etched. As increasing oxidative effect, the carbon surface was growing in saturated with the oxygen-containing groups, hence maximizing the specific absorption, and thereafter, occurring no more change. However, when the remained amount of oxidative carbons exceeds 18 to 20%, the specific absorption was declined.

Such phenomenon is coincident with the result depicted in Russian Patent No. 2046094 by Bjuljuten Izobretenij, (29), 189 (1995), [Synthetic diamond contained materials]. The Russian technology is briefly illustrated in FIG. 4 for reference.

Figure 4:
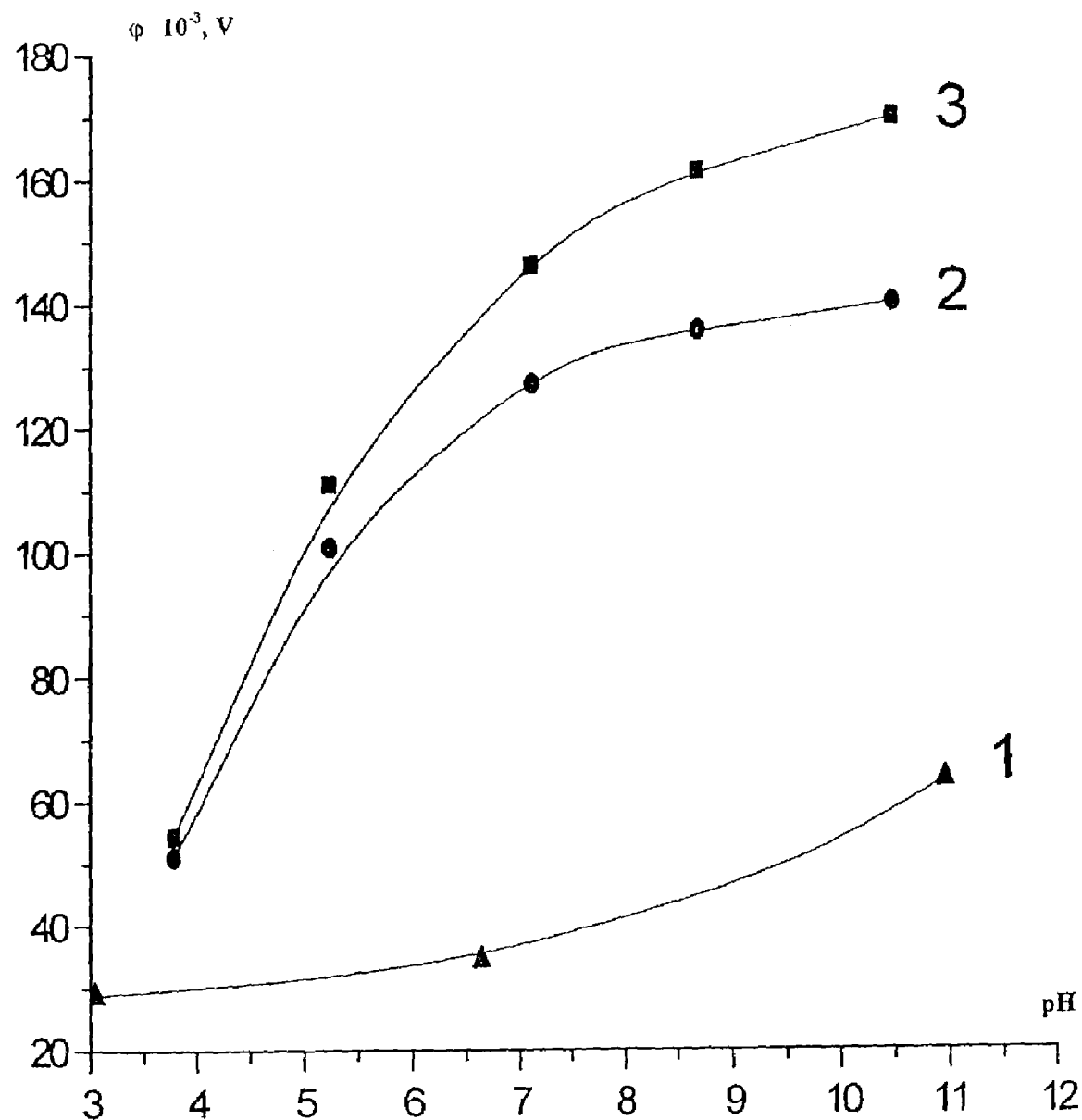
FIG. 4 is a diagram showing the relationship between the pH value and the activity of the UDD fine particle of the present invention.

Remarkable curves shown in FIG. 4 represent a change in the structural property of the BD surface during the treatment with an oxidizer, namely shifts from the graphite structures to the diamond structures (similar to the shifts in the present invention). The materials have high absorption in middle courses of the conversions. With oxidations under intensive oxidizing conditions, merely stable structure forms were remained. Under a moderate oxidation conditions, the interfaces between the diamond carbons and the non-diamond carbons were replaced. Actually, 18 to 20% of the remaining oxidative carbon in the phase of diamond (close to real diamond) is carbons constituting a shell surrounding each diamond cluster.

EXAMPLE 3

Figure 5:
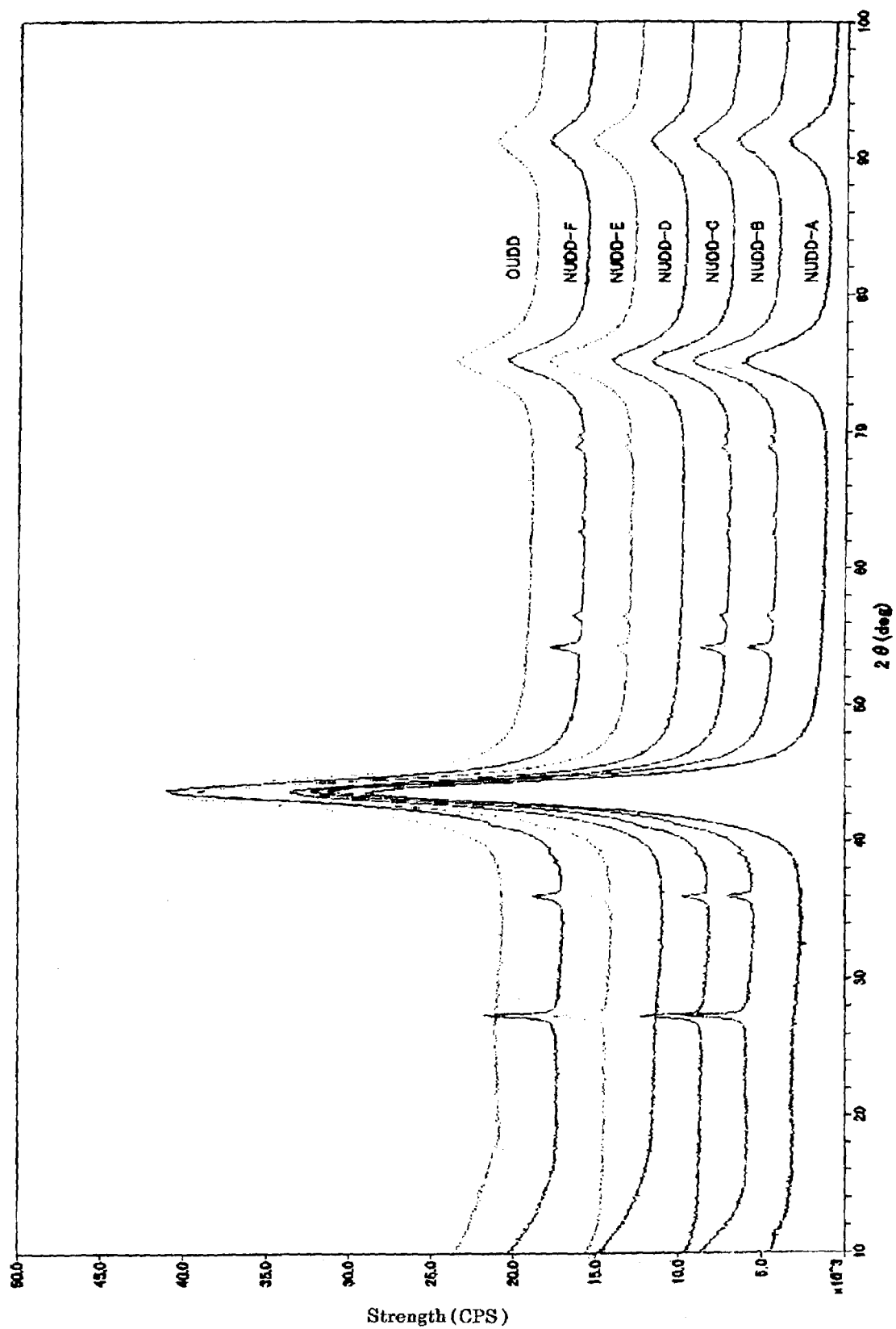
FIG. 5 is an X-ray diffraction chart with respect to the examples of a powder of the UDD fine particle of the present invention.
Figure 7:
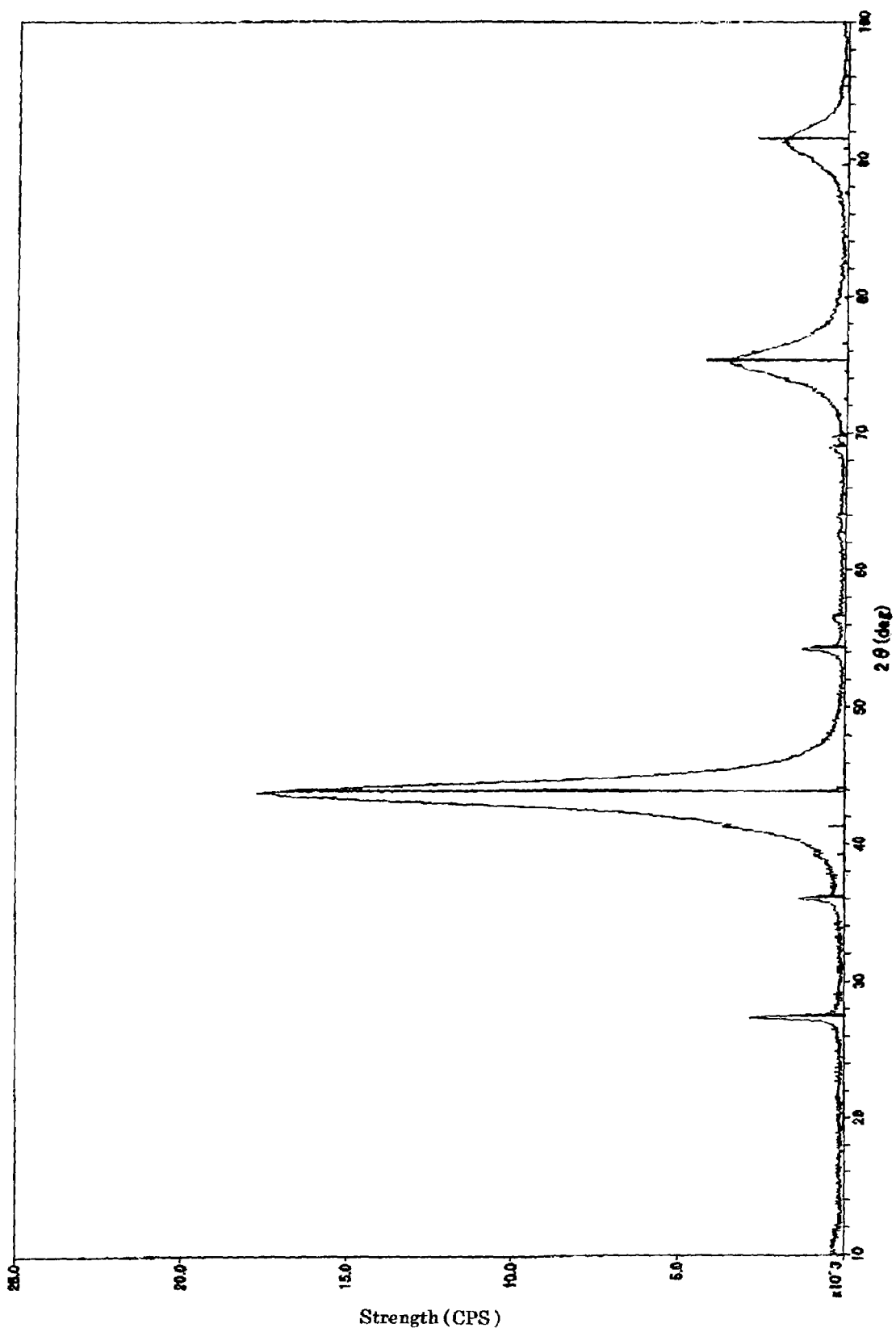
FIG. 7 is an X-ray diffraction chart with respect to in detail an example of a powder of the UDD fine particle of the present invention.

FIG. 5 illustrates measured results of the Bragg angle (2θ±2°) on the X-ray diffraction (XRD) spectrum using Cu—Ka radiation of seven samples: No. 13 of Example 5 (at α=49%, sample A), No. 14 of Example 5 (at α=56%, sample B), No. 4 of Example 1 (at α=55%, sample C), No. 5 of Example 1 (at α=64.9%, sample D), No. 6 of Example 1 (at α=74.4%, sample E), No. 1 of Example 1, No. 8 of Example 5 (at α=0%, sample F), and a conventional UDD sample (in dry powder, sample G). With respect to those samples, FIG. 6 shows the result using sample A, FIG. 7 shows the result using samples B. It is apparent from the charts of FIGS. 5, 6, and 7 that the UDD samples of according to the present invention exhibit some peaks of the reflective intensity, the highest of 85.0% at 44° of the Bragg angle (2θ±2°) pertinent to the (111) crystal structure, 14.0% at 73.5° pertinent to the (220) crystal structure, 0.2% at 91° pertinent to the (311) crystal structure, and 0.2% pertinent to the (400) crystal structure. And, there was no peat at 26.5°±2° pertinent to a (002) graphite plane. Therefore it is obvious that the UDD of the present invention does not contain (002) graphite plane.

As a result of measurements, it is proved that presence of many patterns pertinent to the particular of $Sp^3$ carbon concentrations, thereby diamond phases are existing around a graphite phase of minimum size in the UDD.

In the XRD graphs of samples of containing as a main sample of the UDD at the degree of oxidization α=64.9% according to the present invention, some Lorenz diffraction spectrum peaks having a wide, symmetrical shape appear at 2θ=43.9° of the Bragg angle pertinent to the (111) crystal structure, at 2θ=73.5° pertinent to the (220) crystal structure, and at 2θ=95.5° pertinent to the (311) crystal structure were recorded.

These spectra were ones reflected by the diamond form having a crystalline lattice parameter α=(3.565±0.005)×10⁻¹⁰ m. Using Shehre's equation, the average particle diameter of the UDD is then calculated from values of half width of these spectra curves. Mean particle diameter L=(42±2)×10⁻¹⁰ m was obtained.

There was also provided a biased halo at 2θ=17° of the Bragg angle. When drawn with the primary beam, the intensity of scattering was high and stable. The intensive scattering of the primary beam represents the diffraction property based on amorphous structure. Apparently, the measured halo dose not imply diffracted light on the macro structure, however the halo is closely related to the scattering on very small structure such as a molecular size (for example, the size of graffin or a benzene ring). Such structure may be regular chains of carbon atoms or a planar assembly of regular carbon layers as well as peripheral particle (in diamond structure) of not smaller than $4×10^{-9}$ m in size. By such halo having a high intensity, as compared with the peak intensity of the (333) crystal structure, there is existence of a structure of the molecular size. It was then assumed from a half the intensity of the halo by Shehre's equation, that the size of the structure was substantially $1.5×10^{-9}$ m. Since there are detected smaller particles of the order of $4\times10^{-9}$ m, the amorphous form of diamond and graphite specified in a Raman scattering spectrum may be present.

From the analysis of the X-ray diffraction (XRD) spectrum charts using a source of Cu,Kα ray, it is found that the diamond fine article may have the largest peak at a Bragg angle ($2\theta\pm2°$) of 43.9°, the total intensities of the peaks at other Bragg angles than that of the largest peak being amounted to be 11/89 and 19/81. In other words, the diamond fine particle may have an (111) plane diffraction as high as 81 to 89.

EXAMPLE 4

IR Analysis

Figure 8:
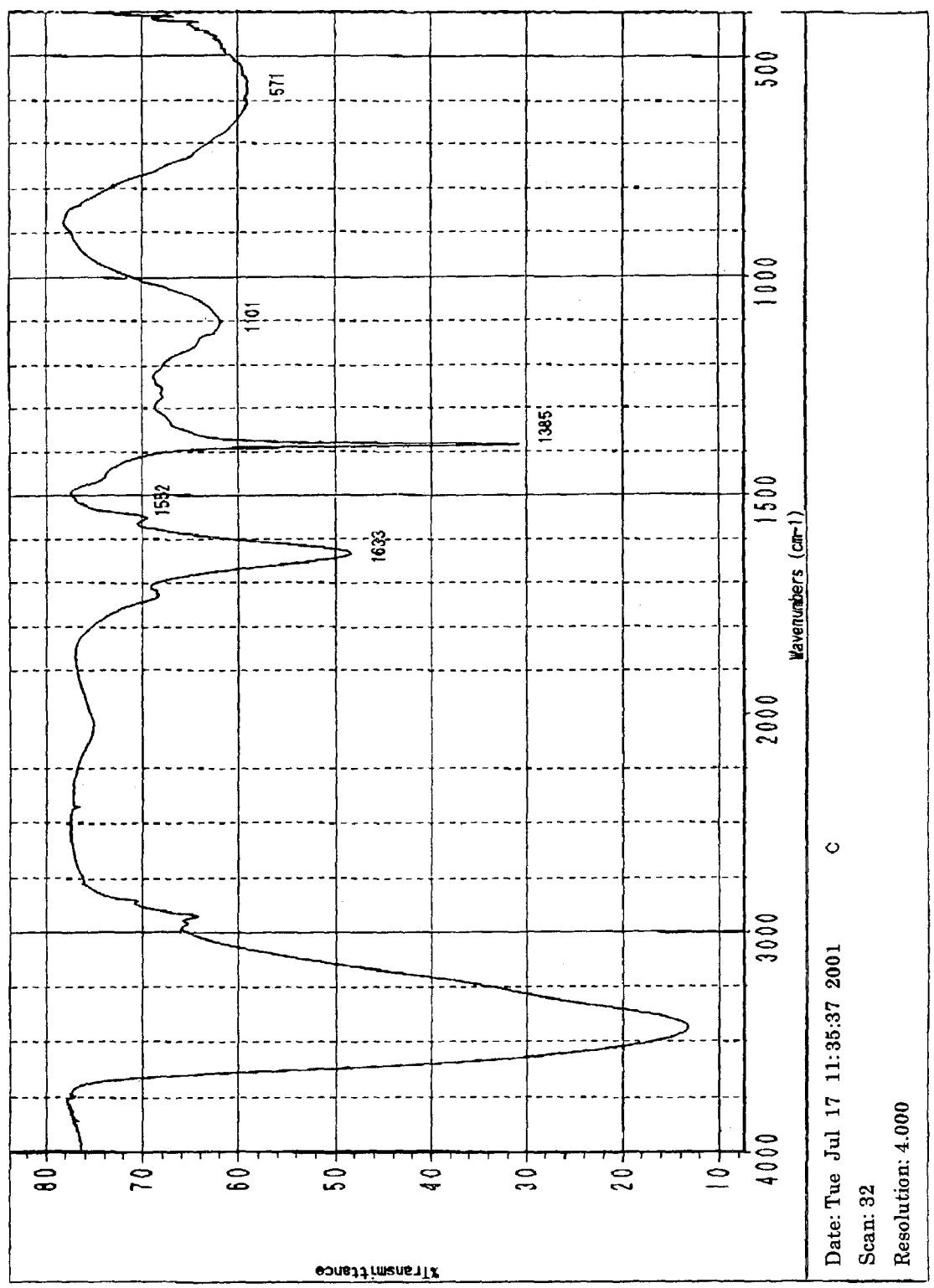
FIG. 8 is an IR measurement chart with respect to an example of a powder of the UDD fine particle of the present invention.
Figure 9:
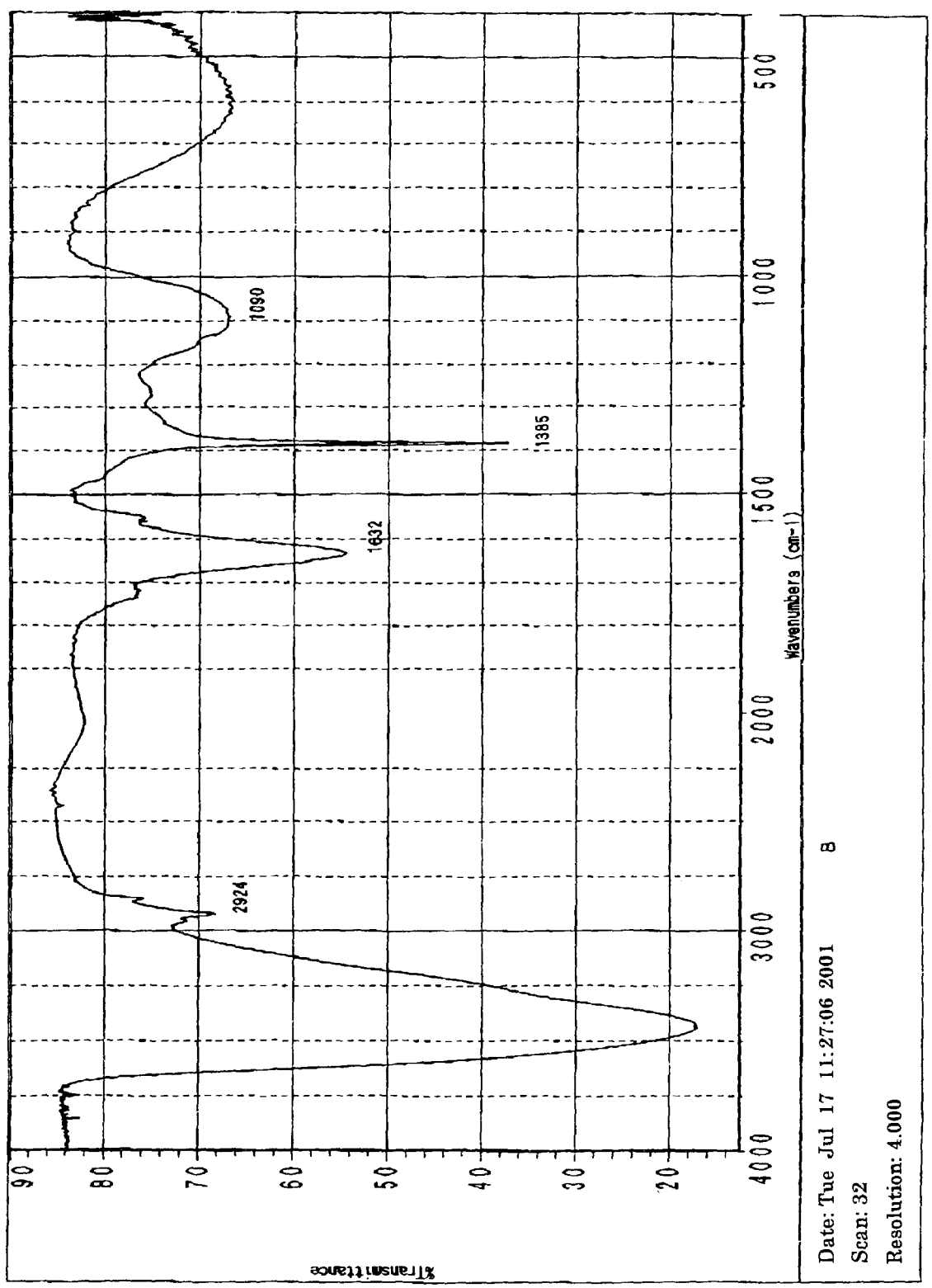
FIG. 9 is an IR measurement chart with respect to an example of a powder of the UDD fine particle of the present invention.
Figure 10:
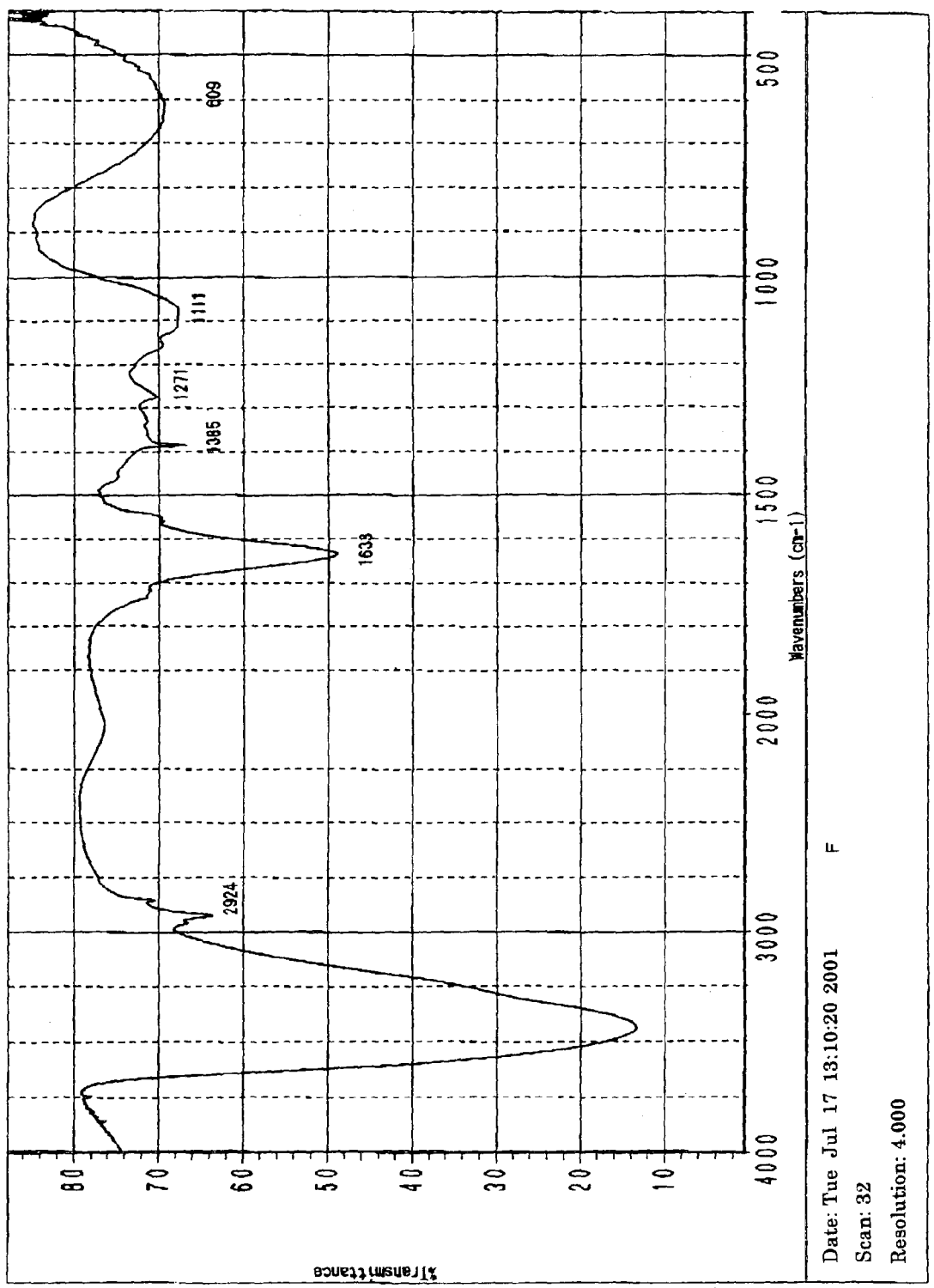
FIG. 10 is an IR measurement chart with respect to an example of a powder of the UDD fine particle of the present invention.
Figure 11:
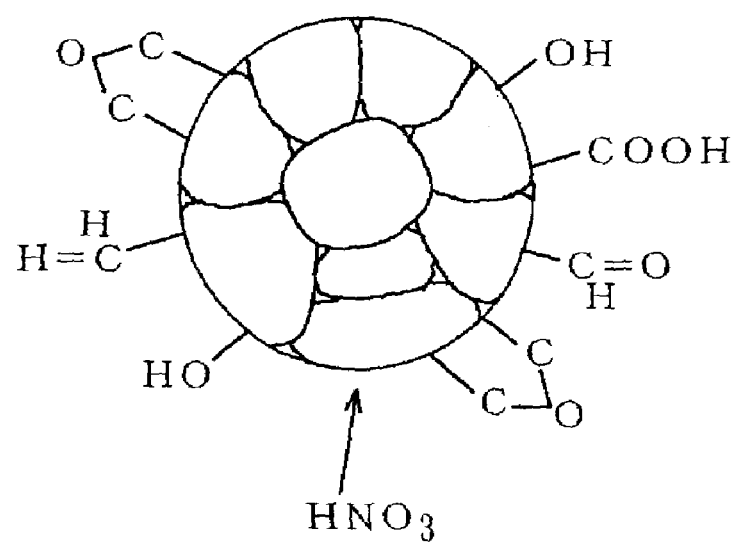
FIG. 11 is an enlarged schematic view of a particle of the UDD fine particle of the present invention.

As shown in FIGS. 8, 9, and 10 are the result of measurements of three UDD samples, similar to Example 1, on the FTIR spectrum for KBr crystal synthesized from the BD materials at α=64.9%, α=74.4%, and α=75.6% denoted in Table 3. In case of the UDD sample which were not sufficiently purified, there are detected an absorption pertinent to carbonyl group which is widely biased throughout a range of 1730 to 1790 $cm^{-1}$ by influences of many other groups existing on the Sample surface, and absorptions of at 1640 $cm^{-1}$ and 3400 $cm^{-1}$ pertinent to hydroxy group which were shifted forward and backward by influences of many other groups existing the surface, as shown in FIGS. 8, 9, and 10. The absorption at a wavelength of 1640 $cm^{-1}$ is affected by bonded water and water releasing. An absorption at 1750 $cm^{-1}$ concerns with vibration of OH group. A broad absorption at a range of 1100 to 1140 $cm^{-1}$ is considered to result from absorption by impurities of nitro group, and therefore, it may be applicable thereto. Therefore, a part of impurities such as silicon, potassium and iron may, on the contrary, decrease the water hardness used in the purification technique of the UDD fine particle. Iron is basically an impurity due to the method (that it, it may be easy to use in the process of explosion method), and thereby, it is difficult to reduce it below the concentration of 1.0 or 0.5% by weight. The impurity of iron at such amount may be there mainly on the surface thereof.

As being apparent from the results, the intensity and the location of the absorptions of the carbonyl group on the UDD of the present invention largely depend on the purification conditions of the UDD. When heated to 700° C. under an atmosphere of nitrogen gas, both the carbonyl group and the carboxyl group were decomposed thus declining the physical strength of corresponding regions thereof. As the UDD has been heated to 673 degree K, an absorption thereof was shifted from 1730 $cm^{-1}$ to a position of 1780 to 1790 $cm^{-1}$, thus this implies the building up of O=C—O—C=O structure.

As being apparent from the result, the UDD of the present invention after being purified with nitric acid has absorptions shifted from the original locations into next locations, showing patterns as denoted below in Table 4.

TABLE 4

| IR - spectrum of UDD | |
| --- | --- |
| 3500 $cm^{-1}$ | An intensive wide band |
| 1740 $cm^{-1}$ | A band of mean intensity |
| 1640 $cm^{-1}$ | A band of mean intensity |
| 1260 $cm^{-1}$ | An intensive wide band |
| 1170 $cm^{-1}$ | An intensive wide band |
| 610 $cm^{-1}$ | A wide band of mean intensity |

Among these absorptions, the UDD fine particle has the largest absorption band at a wavelength of around 3500 $cm^{-1}$. The UDD fine particle also has an Absorption band at a wavelength of around 1740 $cm^{-1}$ smaller than an absorption band at a wavelength of around 1640 $cm^{-1}$, comprising a plural of absorption bands being complex and flat at top. The absorption band at a wavelength of around 1640 $cm^{-1}$ is the second largest. The absorption band at a wavelength of around 1170 $cm^{-1}$ is the third largest, and its profile has at least two small peaks at a longer wavelength side and at least two shoulders moderately sloping down. The UDD fine particle also has an absorption band at a wavelength of around 610 $cm^{-1}$, which has a complex and broad profile with a medium intensity.

Further, the UDD fine particle of the present invention has small peaks or at least shoulders at a wavelength of 2940 $cm^{-1}$ (which is pertinent to C—H saturation), 1505 $cm^{-1}$, 1390 $cm^{-1}$, and 650 $cm^{-1}$.

As being apparent from the result, the UDD fine particle of the present invention, as shown in FIG. 1, is covered with many active functional groups such as —COOH, —C—O—C—, —CHO, and —OH groups and the like.

EXAMPLE 5

Oxidation Degree and Surface Property

Samples of No. 8 to No. 19 were prepared by the same manner as of Example 1, however, these samples were different in the degree of oxidization from those of Example 1, therefore their surface properties about the oxidative decomposition and the oxidative etching were also different as shown in Table 6, including Sample 8 (α=0.0%), Sample 9 (α=17%), Sample 10 (α=28%), Sample 11 (α=32%), Sample 12 (α=48%), Sample 13 (α=49%), Sample 14 (α=56%), Sample 15 (α=63%), Sample 16 (α=81% as Comparison 4), Sample 17 (α=85% as Comparison 5), Sample 18 (α=94% as Comparison 6), and Sample 19 (α=98% as Comparison 7). Then, their surface characteristics in connection with the degrees of oxidative decomposition and oxidative etching were measured, Results were shown in Table 5.

TABLE 5

| No. of sample | Fraction of total mass of oxidizable carbon (%) | Degree of oxidative decomposition (α) | | Specific surface ($10^3 \times m^2/kg$) | Limit volume of sorption space ($m^3/kg$) | Size of space ($10^{-9}$ m) | Size of critical pores ($10^{-9}$ m) |
| --- | --- | --- | --- | --- | --- | --- | --- |
| No. 8 | 53.4 | (DB) | 0 | 404 | 1.2451 | 9.1 | 8.8 |
| No. 9 | 44.4 | | 0.17 | 409 | 1.0746 | 8.1 | 8.0 |
| No. 10 | 38.4 | | 0.28 | 399 | 0.9931 | 7.7 | 7.9 |
| No. 11 | 36.3 | | 0.32 | 314 | 0.7488 | 7.5 | 7.6 |
| No. 12 | 27.8 | | 0.48 | 244 | 0.6621 | 8.6 | 6.8 |
| No. 13 | 27.6 | | 0.49 | 209 | 0.5406 | 8.7 | 8.8 |
| No. 14 | 23.7 | | 0.56 | 198 | 0.5236 | 9.1 | 9.1 |
| No. 15 | 19.5 | | 0.63 | 195 | 0.5089 | 9.5 | 9.3 |

TABLE 5-continued

| No. of sample | Fraction of total mass of oxidizable carbon (%) | Degree of oxidative decomposition ($\alpha$) | Specific surface ($10^3 \times m^2/kg$) | Limit volume of sorption space ($m^3/kg$) | Size of space ($10^{-9}$ m) | Size of critical pores ($10^{-9}$ m) |
|---|---|---|---|---|---|---|
| No. 16 (Comparative 4) | | 9.9 | 0.81 | 240 | — | — | — |
| No. 17 (Comparative 5) | | 7.9 | 0.85 | 252 | — | — | — |
| No. 18 (Comparative 6) | 20 | 3.4 | 0.94 | 276 | 0.8241 | 9.8 | 9.6 |
| No. 19 (Comparative 7) | 21 | 1.2 | 0.98 | 290 | 0.8396 | 9.2 | 9.2 |

1) Limit volume of sorption space ($m^3/kg$) is presented by ($p/p_5$) = 0.995 (Where p is degree of filled up surface of inner pores by $N_2$, $P_s$ is limit pressure of $N_2$ gas to create mono layer of Nitrogen.)
2) Size of critical pores is the maximum size of pores by which atoms of adsorbing gas are able to pass into adsorbent(UDD).

It is apparent from Table 5 that the absorptivity of the UDD substantially do not necessarily depend on the pore size and the limit pore size, but depend on the activity ratio and the magnitude of activated surface area in all of the UDD surface. Conventionally, there were reported studied about the activity of UDD, including one which was depicted in GP. Bogatiryonva, M. N. Voloshin, M. A. Mirinich, V. G. Malogolovets, V. L. Gvyazdovskaya, V. S. Gavrilova, Sverhtvjordii Materiali, No. 6, pp. 42 (1999), [Surface and electro-physical properties of dynamic synthesis nano-diamond]. For just purposes of comparison and reference, it is shown in Table 6.

TABLE 6

| Sample Unburnt residuum (%) | Specific magnetic susceptibility (X) ($m^3/kg$) | Specific surface ($S_{sp}$) ($10^2 \times m^2/kg$) | Adsorption potential (A) ($10^3$ J/kg) | Specific adsorption potential (A') (J/$m^2$) |
|---|---|---|---|---|
| UDD a 0.75 (Comparative Example 8) | ~035 · $10^{-8}$ | 167 | 400 | 2.4 |
| UDD b 1.16 (Comparative Example 9) | 0 | 162 | 550 | 3.4 |

1) Susceptibility (X) were determined by the technique of V. N. Bakul Institute of superhard materials.
2) Specific surface ($S_{sp}$), adsorption potential (A) and specific adsorption potential (A') were isotherms of low temperature adsorption of nitrogen gas by mean of the instrument "Akusorb-2 100" and calculated therefrom.

It is proved from the technical knowledge relating to adsorption and desorption of nitrogen gas measured by PET shown in Tables 5 and 6 that the UDD Samples of the present invention having an oxidation degree a lower than 81% were sufficiently developed in the activity and greater in the specific surface area, $4.5 \times 10^5$ $m^2/kg$ at the maximum, and in the surface area carbon content ($C_{surface}/C_{total}$), and, in comparison with conventional samples (Comparison Examples 8 and 9). The density of the functional groups in $C_{surface}$ was as high as 100%. In general, the rate of carbon atoms bonded to hetero atoms in the total number of carbon atoms of the conventional synthetic diamonds was as low as 15%.

EXAMPLE 6

Differential Thermal Analysis

Also, the samples of the UDD fine particle were subjected to thermal differential analysis in atmospheres of air and inert gas. Result is shown as follow.

Namely, in case of heated at a heating speed of 10° K per minute in the air, every sample started oxidization at 703° K. On the other hand by literature, in case of three different samples synthesized by the conventional static conversion, starting temperatures of oxidizations were 863° K, 843° K, and 823° K, respectively. Accordingly, the UDD of the present invention has higher activity for oxidizing.

When heated to 1273° K under a neutral atmosphere, one of the samples of the present invention exhibited a weight loss of 3 to 4%. The same sample, when heated at a proper speed from 443° K to 753° K under carbon dioxide gas, increased its weight by 5% and when heated to a higher temperature, its weight was declined. This sample, when heated under an atmosphere of hydrogen gas, caused separation of HCN gas. The same UDD sample was then composite thermal differential analyzed.

The result of the analysis was denoted in the form of a thermograph curve having the three features (a) to (c) below.

(a) The weight loss was 5 to 7% when heated at 373 to 383° K (of two samples at $\alpha$=63% and $\alpha$=27%). This was reversible. As the resultant gas product was measured at the same temperature, it contained 97 to 98% of nitrogen gas. It may be concluded that the gas is one absorbed and separated from the air.

(b) The UDD sample was declined in the weight at 523° K, with heat absorption.

(c) The weight loss was detected at a range from 753° K to 1023° K, with heat generation. Particularly, the weight loss was large (up to 95%) at 753 to 773° K, with large amount of heat generation, and this was lasted until the temperature reached to the range of 1023 to 1053° K, and thereafter, any more no change was shown at higher temperatures than before. Non-combustible residue was then measured by a known manner and its amount was corresponding to 10% of the initial weight of the Sample. It was considered that in the temperature range of 773° K to 1023° K, strong oxidization of carbon was carried out, and finally, non-combustible residue was remained. During the oxidization, intensive grows were detected.

EXAMPLE 7

Affect of Heating on the Hydrophilic Group on the Surface of UDD Fine Particle Then, samples 11, 13, and 14 were heated at a heating speed of 10° K per minute under a carbon dioxide atmosphere until the temperature reaches 1273° K. Then, their weight and specific surface area were examined for increase or decrease, similar to Example 5. The weight measurements exhibited no particular increase or decrease (more specifically, Sample 11 was decreased by 0.25%, Sample 12 increased by 0.22%, Sample 13 decreased by 0.15%, and Sample 14 increased by 0.22%). The specific surface area of each sample also remained substantially unchanged. This may be explained by the condensates of carbon atoms in the pores were remained in stable non-graphite form, and the hydrophilic groups as electron donors, such as hydroxyl, carboxy, carbonyl, or aldehyde were remained, not eliminated by heating.

EXAMPLE 8

Particle Diameter Distribution

Seven samples were examined for determining profile of particle sizes, including Sample 13 of Example 5 (at $\alpha$=49% denoted as Sample AS in FIG. 15), Sample 14 of Example 5 (at $\alpha$=56% as Sample BS in FIG. 16), Sample 4 of Example 1 (at $\alpha$=55% as Sample CS in FIG. 17), Sample 5 of Example 1 (at $\alpha$=64.9% as Sample DS in FIG. 18), Sample 6 of Example 1 (at $\alpha$=74.4% as Sample ES in FIG. 19), Sample 8 of Example 5 (at $\alpha$=0% as Sample FS in FIG. 20), and a conventional UDD sample (in dry powder as Sample GS in FIG. 21).

Figure 12:
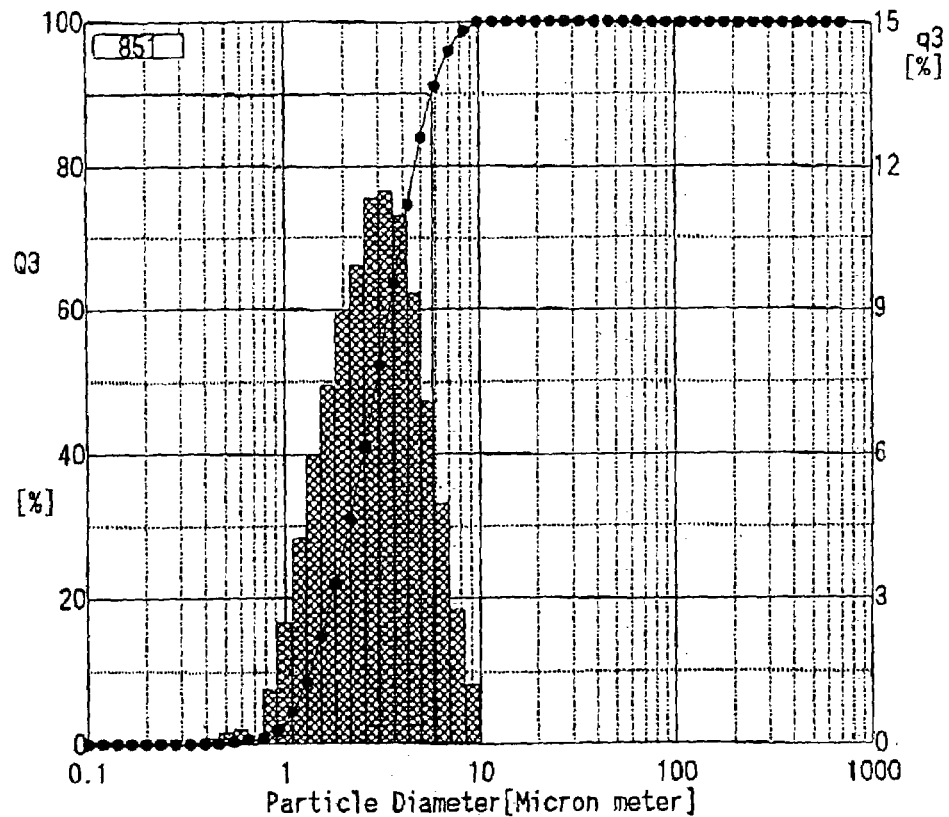
FIG. 12 is a graph showing a profile of a particle size distribution of an example of a powder of he UDD fine particle of the present invention.
Figure 13:
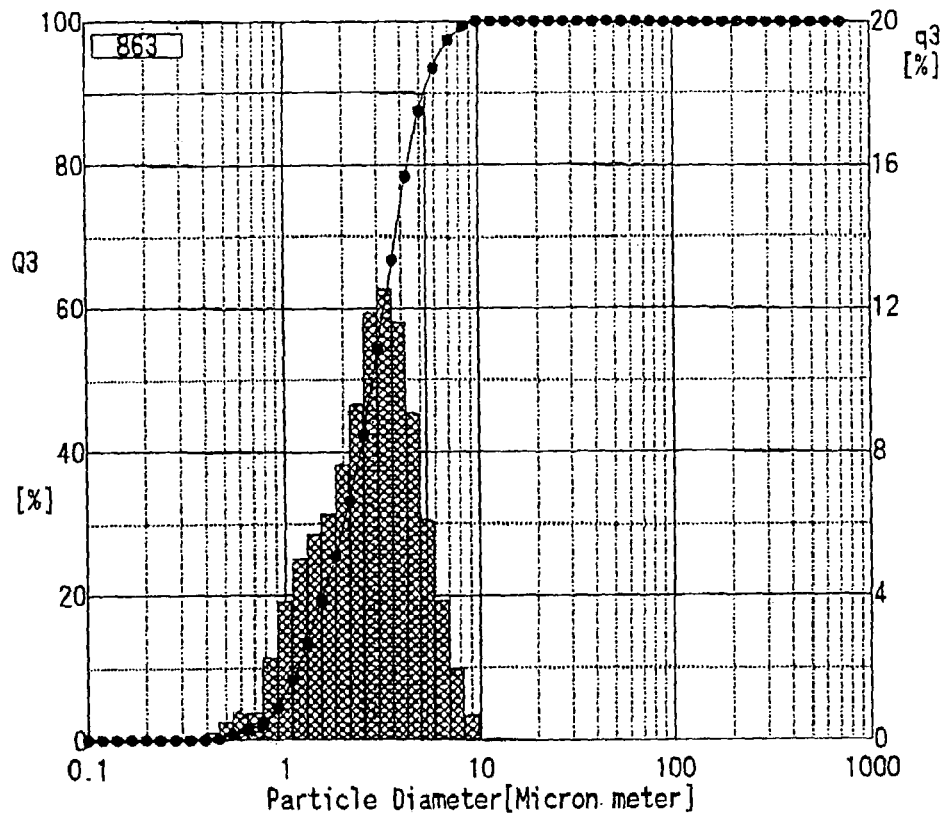
FIG. 13 is a graph showing a profile of a particle size distribution of an example of a powder of the UDD fine particle of the present invention.
Figure 14:
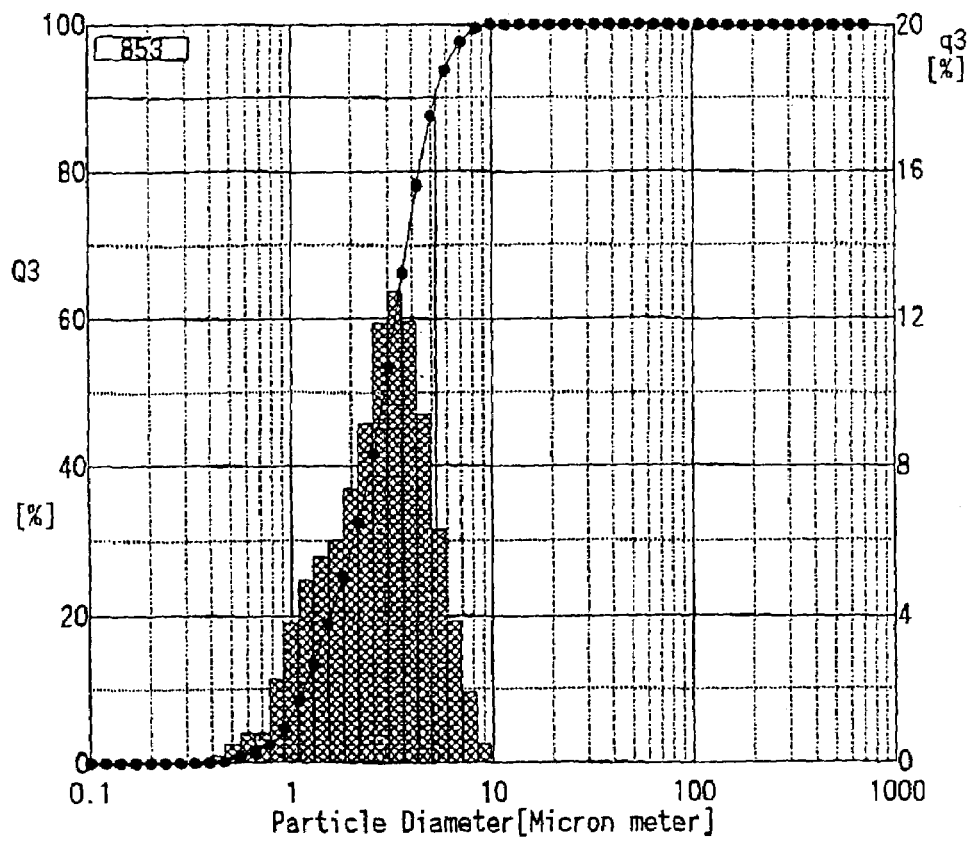
FIG. 14 is a graph showing a profile of a particle size distribution of an example of a powder of the UDD fine particle of the present invention.
Figure 15:
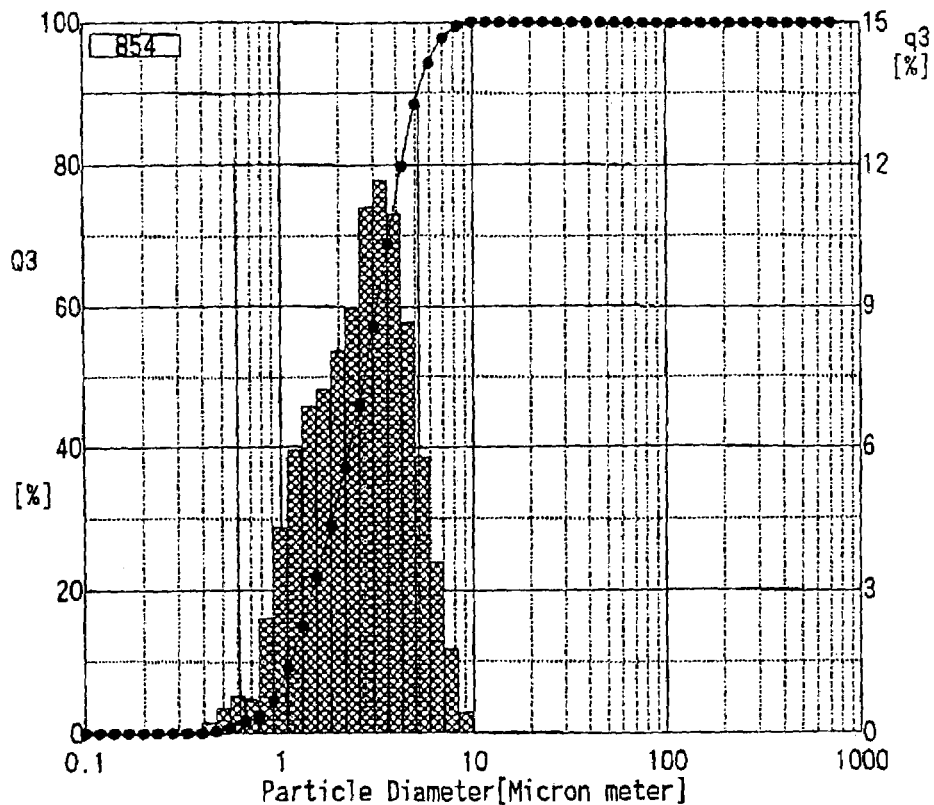
FIG. 15 is a graph showing a profile of a particle size distribution of an example of a powder of the UDD fine particle of the present invention.
Figure 16:
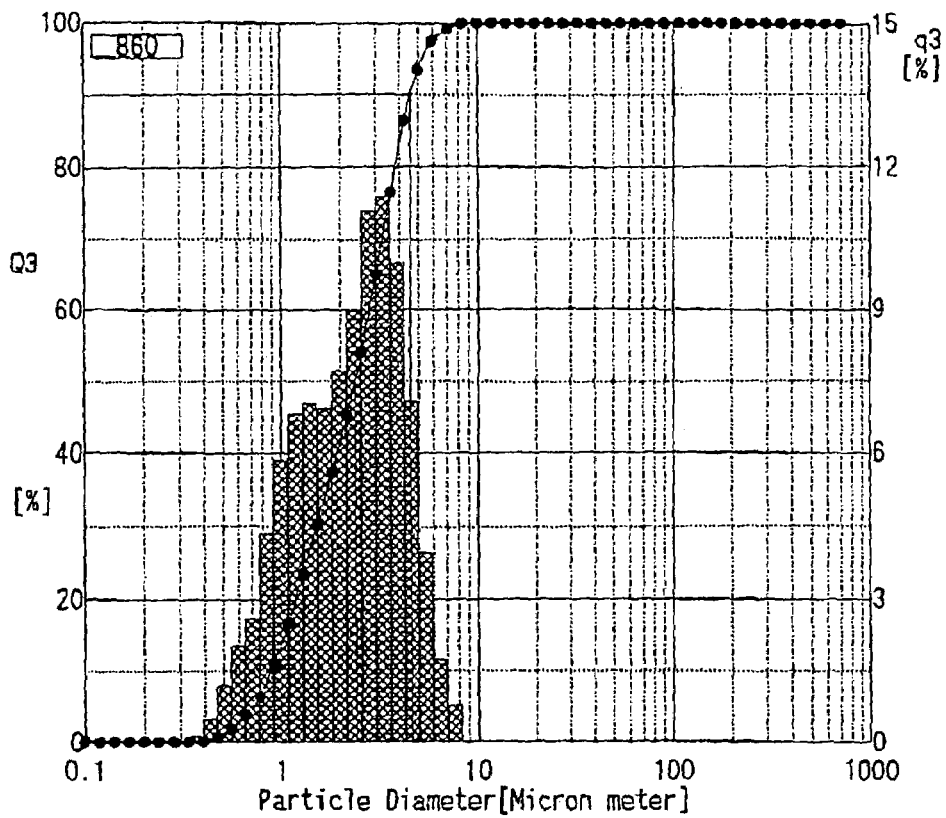
FIG. 16 is a graph showing a profile of a particle size distribution of an example of a powder of the UDD fine particle of the present invention.
Figure 17:
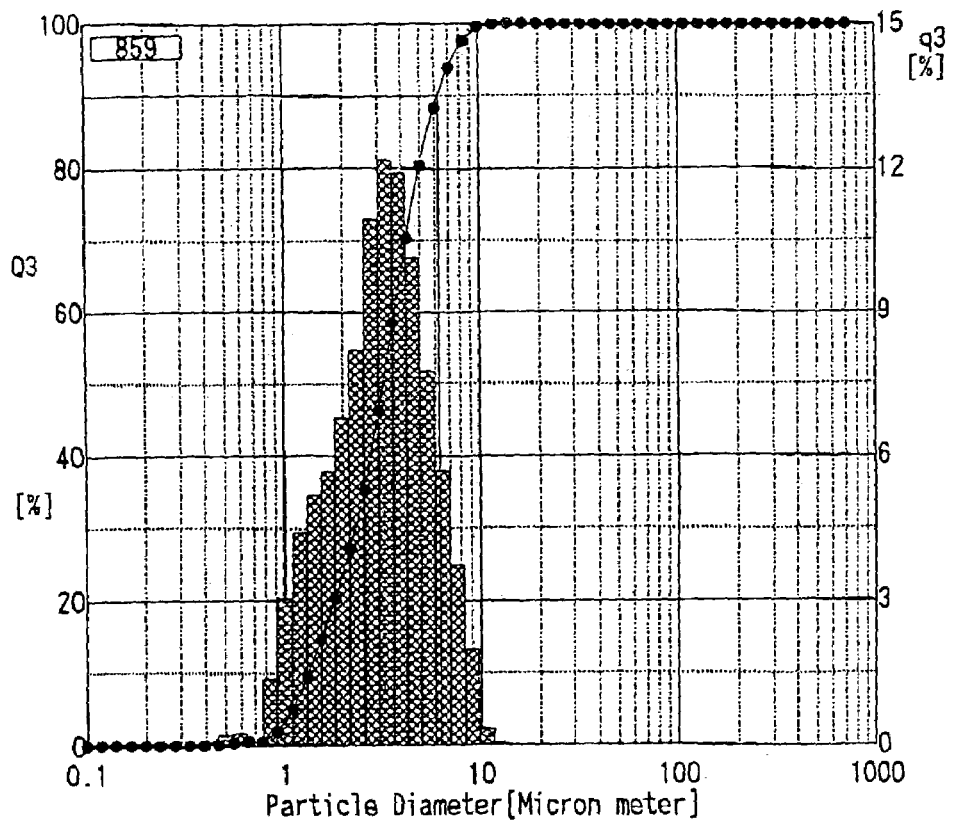
FIG. 17 is a graph showing a profile of a particle size distribution of a powder sample subjected to an incomplete oxidization treatment sample of a crude diamond synthesized by means of explosion method.
Figure 18:
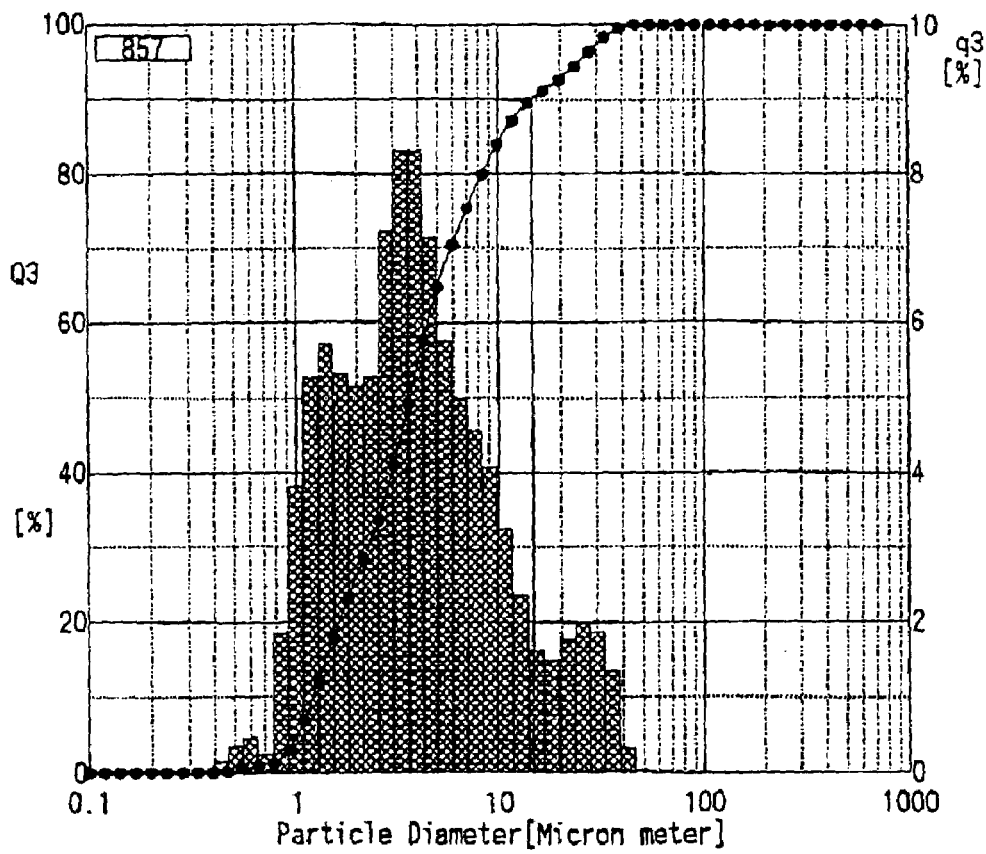
FIG. 18 is a graph showing a profile of a particle size distribution of a powder sample of a conventional UDD fine particle.

The resultant profiles of Samples AS to GS were shown in FIG. 12 (Sample AS), FIG. 13 (Sample BS), FIG. 14 (Sample CS), FIG. 15 (Sample DS), FIG. 16 (Sample ES), FIG. 17 (Sample FS), and FIG. 18 (Sample GS).

It was found from the result that while the conventional UDD sample (Sample GS) and the non-oxidized UDD powder (Sample FS) containing large particles of 1000 nm or greater in the diameter and widely varying in the particle size, samples of the present invention (Samples AS, BS, CS, DS, and ES) were smaller range by diameter distribution and containing no large particles of 1000 nm or greater diameter.

EXAMPLE 9

Removal of Absorbed Water and Nitrogen

On the other hand, wet UDD of the present invention lost humid substantially, when heated to a temperature in the range of 403 to 433° K. At higher temperature than that of before, the parameter change was similar to that of the dried samples. In case of heated to 383 to 393° K under an inert gas (He) atmosphere, the wet UDD started releasing nitrogen which was absorbed from and desorpted to the air, reversibly. At a range from 673° K to 1173° K, the weight was lost by about 10%, with heat generation. Thereafter, carbon dioxide and nitrogen were released (ratio thereof were 4:1 by molar), accompanying with morphology changes of the UDD. At a temperature in the range of 1153° K to 1163° K, any more no change was detected, while very slight heat absorption was susceptible. This process was conducted without any change in the structure and color of the UDD. On the other hand, by data provided from prior arts, the functional groups are eliminated from the surface at the range of said temperature during annealing procedure conducted under the inert gas atmosphere.

EXAMPLE 10

Volumetric Ratio of the Structure Defects

The volumetric examination of structural defects in the UDD of the present invention was conducted.

With regard to all crystal states which were considered as diamond structures in the wide meaning depend upon aforementioned IR analysis denoted in Example 4, volumetric ratio of structural defects was examined by positron-eletron annhilation method.

The UDD samples were prepared by shock conversion processes in water from TNT/RDT alloys containing 5 to 70% by weight of highly dispersible RDX.

For purposes of determining concentration, volume, and dispersion state of structural defects of the UDD samples in the sintering processes, changes were made in the carbon/hydrogen ratio in the explosive, the diameter of imposed shock wave (at a higher pressure and a higher temperature), and the harden level. After chemical purification, the crystal structure of obtained UDD was measured by the positron-electron annihilation method to determine the volumetric ratio of the structural defects. And specific area of the UDD was measured by absorption of nitrogen at low temperature.

Also, for the purpose of studying the sintering process of the UDD having the volume (($3.05$ to $3.10)\times 10^3$ kg/m$^3$) of maximum density of the structural defects, selections were made with an average diameter (($1.5$ to $2.0)\times 10^{-9}$ m) of the UDD by a coherent dispersion technique, and with maximum dispersibility (specific surface area of $4.2\times 10^5$ m$^2$/kg) of the UDD. The UDD powder was sintered under 4 to 12 GPa, and resultant polycrystalline powder condensate was measured to study the macro hardness and the compression fracture strength.

In the detonation of a carbon-contained explosive, the densities of vacancy defects of cluster and pores were increase in proportion with the increase of carbon content and increase detonating temperature, and there were peak points in curve lines showing the maximum density of vacancy defects of cluster and the maximum pores, after passing through the peak points, the density of vacancy defects of cluster and density of pores were began to decrease. The peak was at substantially 3900 degree K degree, and concentration of sub-micro pores having diameter of $(1$ to $2)\times 10^{-9}$ m was increased to the maximum. The trap centers for trapping the electrons to disappear were total defects. Every defect was eventually core of a sub-micro pore. Such site of positronium in the UDD was not located in the inside of diamond but formed in the inner surface of sub-micro pore and thus was constituted by the defect.

When the volume of the sub-micro pores in the UDD prepared from TNT was decreased and the structural defects were decreased (to the density $3.3\times 10^3$ kg/m$^3$), the quality of the UDD approached to similar to that of static conversion synthesized diamonds. IR spectra of conventional UDD powder sample told this nature.

The generation of the structural defects in the UDD of the present invention may thus be explained by the following hypothesis (which is shown for only the purpose of description and not intended to limit the present invention).

Namely, the formation process by detonation of carbon-containing explosive can be represented as the results of unbalanced phase transitions, involving: (1) by carbon-containing explosive, occurring of a primary plasma-like dense state which is characterized by a high density of ions, free electrons, excited particles, the simplest radicals et al.; (2) occurring a plasma-like dense state, a state of primary small carbon clusters containing hydrogen; (3) occurring a state of primary cluster, a ultradispersed diamonds phase. All of the transitions produced within $10^{-8}$ to $10^{-9}$ second, just when an electronic subsystem of particles is excited, that creates additional conditions for ultra high-speed formation of diamond phase according to new mechanisms. Then, both in the zone of chemical transformation of explosives and outside it, in the zone of high pressure and temperature, there are slower diffusion processes of coalescence, recystallization and growing of cores of diamond phase, splitting out and diffusion of hydrogen, formation of vacancies, their accumulation to vacancy clusters and submicropores. This is a slow-speed stage closing formation of crystalline structure of UDD, it proceeds for $10^{-6}$ second and more being interrupted by hardening of the powder.

EXAMPLE 11

Electromagnetics Property

The magnetic properties of UDD samples of the present invention were compared with those of conventional diamonds synthesized by static conversion.

In general, diamonds are diamagnetic having a constant value of magnetic susceptibility of $\Pi=-0.62\times10^{-8}$ m$^3$/kg. However, the UDD of the present invention has a different magnetic susceptibility value from above general value. Specific magnetic susceptibility of a powder material is a quantity characteristic properties of all volume of a powder and is defined at the expense of additive addition of specific magnetic susceptibilities ($\Pi_1$) of all components in a powder with due regard for their concrete content. In Table 7 below, the magnetic susceptibilities of impurities in the UDD Samples of the present invention are shown.

TABLE 7

Magnetic susceptibility of impurities in UDD

| Component name | UDD Samples | Static synthesis Diamond | Approximate value of magnetic susceptibility ($x_1$) ($x_1 = \times 10^{-8}$ m$^3$/kg) |
|---|---|---|---|
| Diamond | + | + | −(0.1~0.5) |
| Metal | Traces | + | $10^3$~$10^4$ |
| Graphite | + | + | −(8.2~0.1) |
| Carbon materials | + |  | −(2.0~0.1) |
| Gelatine |  | + | −(0.5~0.9) |
| Silicon | + | + |  |

According to the present invention, conductivity of the UDD was minimum for the Samples warmed up at 573° K degree in carbon dioxide atmosphere and had the value of about $10^{12}$ Ω·m. The subsequent warm up in carbon dioxide atmosphere increased the conductivity changed to in the range of $6.0\times10^{10}$ to $2.0\times10^{11}$ Ω·m. The electrical conductivity may drop down to $2.3\times10^4$ Ω·m when heated up to 1173° K which is a threshold level prior to turning to a graphite form.

The dielectric constant or permeability of the UDD sample was 2.4 to 2.7 at $E_{0.1}$, 1.7 to 2.0 at $E_{1.0}$, and 1.7 to 2.0 at $E_{1.5}$, while the high-frequency dielectric loss (tan *) was ranged of about $0.5\times10^{-3}$ to $1.0\times10^{-2}$.

As shown, the UDD of the present invention has a number of properties differing them from well known various synthetic diamonds, and in spite of its higher reactivity, a diamond-like phase of carbon is stable in physico-chemical parameters in neutral and reducing atmosphere up to 1273° K.

The specific resistance of the UDD of the present invention formed in compact tablets which was in the range of $10^6$ Ω·m to $10^7$ Ω·m at the room temperature and when humidifying this value were sharply decreases, thus content was as small as 5% moisture, and this specific resistance was than $10^3$ Ω·m. When subsequent increasing of moisture content, the specific resistance did not change. Accordingly, it seems to be defined by absorbed water quantity. Also, the water content 5% may be a reference level for determining a method of measuring the content of remaining water in the UDD.

There is one of the important properties of the diamond surface, that is, an electrokinetic potential or an interface potential (potential or zeta potential) value. Taking into account that potential value considerably depends on a condition of nanodiamond surface, the differences in both the potential values for different UDD fractions of the same quality, and especially for UDD of different purification and modification ways should be expected.

Determination of z potential values of UDD can be carried out by electrophoretic method based on directed movement of particles of dispersed medium relative to liquid phase under current effect, as disclosed in S. I. Chuhaeva et al. (S. I. Chuhaeva, P. Ya. Detkov, A. P. Tkachenko, A. D. Toropov, [Physical chemistry properties of fractions isolated from ultra-dispersed diamonds (nanometer diamonds)], and Sverhtvjordii Materiali, Vol. 42, pp. 29 (1998) in which the zeta potential was measured from three separated layers, a precipitated layer, an intermediate layer, and a suspension layer, of a concentrated UDD suspension synthesized by Russian Federal Nuclear Center, showing potentials of $+16\times10^{-3}$ V at the precipitation, $+32\times10^{-3}$ V at the intermediate layer, and $+39\times10^{-3}$ V at the suspension layer. And, study of IR-spectra of isolated fractions shows that in the specimens there are practically ones and the same functional groups, however, the fractions are differed in their content.

There are reported studies by V. L. Kuznetsov, A. L. Chuvilin, Yu. V. Butenkov, I. Yu. Malkov, A. K. Gutakovskii, S. V. Stankus, R. Kharulin, Mat. Res. Soc. Symp. Proc. 396, pp. 105 (1995), for three of precipitated layer, intermediate layer, and suspension layer, as below.

With respect to respective portion separated into the three layers, details are shown in Table 8.

TABLE 8

Basic physical-chemical characteristics of isolated UDD-fractions

| | Values for fraction | | |
|---|---|---|---|
| Characteristic | 1 (precipitated) | 2 (intermediate) | 3 (suspended) |
| 1. Appearance | Light-grey scattering powder | Grey powder | Black filiform crystal-like formations |
| 2. Pycnometric density ($10^3$ kg/m$^3$) | 3.3 | 3.2 | 3.1 |
| 3. Unburnt residuum (wt. %) | 1.6 | 1.3 | 0.9 |

TABLE 8-continued

Basic physical-chemical characteristics of isolated UDD-fractions

| | Values for fraction | | |
|---|---|---|---|
| Characteristic | 1 (precipitated) | 2 (intermediate) | 3 (suspended) |
| 4. Oxidizable carbon (wt. %) | 1.0 | 1.5 | 1.9 |
| 5. Viscosity of aqueous suspension with concentration of UDD of 10 kg/m$^3$ at 293° K. (mPa sec) | 1.04 | 1.07 | 1.12 |
| 6. Viscosity of aqueous suspension with concentration of UDD of 60 kg/m$^3$ at 293° K. (mPa sec) | 1.32 | 1.63 | 5.15 |
| 7. Electrokinetic potential ($10^{-3}$ V) | +16 | +32 | +39 |

Hitherto, it is known that three fractional suspensions from layer-separation is different one other in characteristics and the difference is caused by different velocities based on compositions and diameters of UDD particles, influences of functional surface groups of the particles to the characteristics of UDD are not known exactly.

EXAMPLE 12

Surface Charge Potential

In the present invention, Samples of the UDD suspension of the present invention were measured by three times at temperatures in the range of 297 to 298° K after they were purified by ions exchange resin. The measurements of the zeta potential given the data of (32 to 34)×10$^{-3}$ V. For comparison, measurement of z potential value of UDD suspension by conventional preparation method (not divided into three fractions) prepared by conventional given data of (25 to 26)×10$^{-3}$ V.

Conventional procedures of fraction separation based on simple stirring of nanometer diamonds in the chosen liquid and precipitation by composition and particle sizes from suspensions by gravity for highly dispersed UDD are not suitable. On the other hand, in the present invention as best case, decantation of very fine fractions will take place. The fine fractions are easily aggregated when drying, and the dried aggregates containing very fine particles are in same cases difficult to break not into original very fine particles. Diameter of aggregates from the UDD suspension in the present invention was minimum 3×10$^{-7}$ m.

Also, the nanometer diamonds has a higher level of organic solvent absorption, therefore the use of organic solvent is not favorable. On the other hand, when dried powder in the present invention is again made into the suspension form using ultrasonic dispersing technique, the disperesibility of the obtained suspension was maintained for over one month in its storage condition.

Samples of various qualities UDD compositions of the present invention have a typical set of functional groups provided therein. Such typical set of functional groups remains constantly until the diamond structure itself is broken up. The set comprises polar functional groups such as —OH, —NH, —C=O, —C—H, or —C=N. In particular, —C=O and —OH may serve as fundamental parameters for determining the aggregation of UDD particles in the suspension liquid. It is found from the IR analysis of fractions in the UDD samples that the samples have a number of functional groups which are different in the proportion of the functional groups.

The stabilization of the UDD suspension of the present invention by surfactant is not inevitable essential, except use of short-chain surfactants having ω, ω' type two-end di-cationic groups. In practice, the UDD particles in the suspension are surrounded by the molecules of the surface-active agent. This causes the tail or in other words hydrophobic portion (a long-chain alicyclic group) of the surfactant to face to be exposed to an aqueous medium. As a result, the UDD particles will be water repellent thus declining the dispersion stability.

EXAMPLE 13

Dispersion Solvent and Dispersion Stability

The UDD particles of the present invention were examined for the compatibility with different dispersant agents. The compatibility and thus the dispersion stability of the UDD particles is increased by the order of acetone<benzene<isopropanol<water. It is apparently essential for improving the dispersibility of the UDD particles to determine the polarity of the dispersant as well as the preparation of a p-composite between the dispersant and the UDD particles which can contribute to the compatibility and the dispersion stability at the surface of the UDD clusters. The UDD suspension using a non-polar organic solvent is most favorable in view of the practical use. Providing that such a nanometer diamond dispersed suspension liquid is feasible, the development of elastomer based clusters is initiated. This can be implemented by a technique of changing the surface of the UDD particles from hydrophilic property to hydrophobic property. For the purpose, the present invention permits a dry powder of nanometer diamond to be dispersed in a benzene solution which contains an elastomer consisting mainly of poly-dimethyl silane and poly-isoprene. More specifically, the suspension of the present invention is stabilized by its diamond cluster absorbed at the surface with polymer hydrophobic chains. As a result, it is proved that the dispersibility of the UDD in the organic solvent is improved. It is then found that the optimum modifier for use on the UDD surface is a polymer of diene material such as poly-isoprene. Hence, a method of modifying the UDD surface and a method of optimizing the suspension liquid can successfully be developed. As the UDD cluster surface is modified by the action of poly-isoprene or the like, the UDD suspension can include large particles having a maximum diameter of about 300 nm.

EXAMPLE 14

Phase Conversion of Diamond Phase—Graphite Phase

The UDD of the present invention is then examined for shift from the diamond phase to the graphite phase. The phase shift is triggered when the UDD is heated in an inert medium at a temperature of 720 to 1400° K. For identifying the phase shift, a Raman scattering (RS) method and an X-ray diffraction method are used in a combination. It is concluded from the result of the RS scattering and the X-ray diffraction that the UDD is a clustered substance having a diamond crystal structure pertinent to nanometer diamonds of about $4.3 \times 10^{-9}$ m in size.

In most cases, the UDD nanometer clusters stay in a small range of the diameter from $4 \times 10^{-9}$ m $5 \times 10^{-9}$ m. It is accordingly understood that the nanometer size crystal is more thermally stable in a diamond form than in a graphite form. This is supported by a report of M. Gamarnik, Phys. Rev. Vol. 54, pp. 2150 (1996).

A profile in the RS spectrum which corresponds to the maximum function of the lattice oscillator density of diamond and graphite represents the presence of small amounts of amorphous diamond and graphite in a sample.

As depicted in G. V. Sakovich, V. D. Gubarevich, F. Z. Badaev, P. M. Brilyakov, O. A. Besedina, Proceeding of Science of USSR, Vol. 310, No. 402 (1990), Aggregation of diamonds obtained from explosives, the UDD cluster or any other ultra-dispersed substance is a single aggregate and its amorphous phase possibly incorporates an aggregate on the surface of its diamond core.

It is confirmed from the X-ray diffraction data of the present invention that the amorphous phase with a particle size of about $1.5 \times 10^{-9}$ m is present. As the peak at 1322 cm$^{-1}$ remains unchanged on the RS spectrum when the annealing temperature $T_{ann}$ is 1000° K, it is true that the structure of diamond is not varied by the annealing temperature. This is also confirmed by the result of the X-ray diffraction analysis which holds the graphite phase when $T_{ann}$>1200° K. The phase shift from the diamond phase to the graphite phase is commenced from the cluster surface during the annealing under the inert atmosphere. It is also confirmed from the result of the X-ray diffraction that the graphite phase is a set of equally spaced graphite nanometer plates having a size of not greater than $4 \times 10^{-9}$ m and that the graphite is substantially created by consumption of the diamond core at $T_{ann}$>1200° K.

As depicted in L. Kuznetsov, A. L. Chuvilin, Yu. V. Butenkov, L. Yu. Malkov, A. K. Gutakovskii, S. V. Stankus, R. Kharulin, Mat. Res. Soc. Symp. Proc., 396, pp. 105 (1995), measurements of the initial phase shift temperature $T_{pt}$ correspond to data of an electron microscope. According to the present invention, the nano-crystalline diamond core having a bulb-like shape of carbon is declined in the size at T>1300° K. As the RS spectrum exhibits a particular shape at 1575 cm$^{-1}$ which represents T=1400° K, the report by V. L. Kuznetsov et al is found correct where 1400° K is the temperature when the bulb-like shape of carbon is developed.

According to the present invention, the shift from the diamond phase to the graphite phase is started at $T_{ann}$>1900° K which is lower than the temperature for triggering the volumetric mono-crystallization of diamond. It is reported in E. L. nagaev, Ussspehifizicheskoi nauki, No. 162, pp. 49 (1992) that the temperature for starting the phase shift or the melting point is low with metal clusters.

At $T_{ann}$>7200K, the regularization of sp$^2$ portions of the UDD is commenced while the graphite phase is developed on the diamond cluster core. The sp$^2$ regularized crystallization is created outside of the diamond crystal core as representing the conversion to sp$^2$ bonded amorphous carbon. This is expressed by the development of micro structures with diffusion patterns throughout small or medium angles of X-ray diffraction at $T_{ann}$>1300° K and an increase in the intensity at 1350 to 1600 cm$^{-1}$ of the RS spectrum.

The cluster of UDD particles comprises a relatively high-density, regular crystalline core and a soft, chemically breakable shell. The diamond core guarantees the fundamental properties of the UDD including the thermal stability, the chemical stability, the high thermal conductivity, the high thermal diffusivity, the low electrical conductivity, the low X-ray diffraction, the quasi-wear resistance, and the quasi-hardness. The shell of the cluster contributes to the negative sign of the charge at the surface of the UDD particles, the absorptivity, the adsorptivity, the chemisorptivity, the chemical composition of each surface functional group, and the colloidal stability of the UDD particles in a liquid or medium. Unlike any conventional metal cluster which consists of chemically hetero elements at the core and ligand shell or a combination of metal atoms and complex forming ions, the UDD cluster is arranged of which the core and the shell both consist substantially of carbon atoms. This allows the diamond lattice structure to be converted via a polyhedron frame, a polycyclic structure, and a net structure to a non-diamond structure of shell form. The cluster boundary can be stabilized by a composite product between carbon atoms of the shell and a gas product from the detonation of an explosive, an air/oxidizer mixture, or an atmospheric substance such as a modifier. For the aggregation of diamond clusters, the shell plays a primary role to react with the matrix component of the explosive and the coating material. The two different components of carbon in the UDD particles are explained in T. M. Gubarevich, Yu. V. Kulagina, L. I. Poleva, Sverhtvjordii materali, No. 2, pp. 34 (1993), [Oxidation of ultra-dispersed diamonds in liquid media] as well as this description of the present invention. The result according to the present invention is similar to that of the above mentioned article.

As depicted in A. I. Lyamkin, E. A. Petrov, A. P. Ershov, G. V. Sakovich, A. M. Staver, V. M. Titov, Proceeding of Academy of Science of USSR, No. 302, pp. 611 (1988), A. M. Staver, N. V. Gubareva, A. I. Lyamkin, E. A. Petrov, Phisika Gorenniya Ivzriva, Vol. 20, No. 5, pp. 100 (1984), Ultra-dispersed diamond powders obtained with the use of explosive, and N. V. Kozirev, P. M. Brilyakov, Sen Chel Su, M. A. Stein, Proceeding of Academy of Science of USSR, Vol. 314, No. 4, pp. 889 (1990), Investigation of synthesis of ultra-dispersed diamonds by mean of tracer method, the structure of an aggregate product fabricated by shock conversion is developed by a primary step of generating a chemical reaction by the detonation of an explosive, and a two-period step of releasing of the reactive phase or the explosion product and permitting the reflection of shock waves to pass across the explosion product. In the N. V. Kozirev's report, the possibility is discussed of the secondary step for shifting diamond to graphite or from the crystal phase to the amorphous phase. Other than the structural conversion and the phase shift which largely affects the carbon frame in each particle, a reaction between the condensation and the gaseous substance in the detonation chamber takes place. Such chemical reactions may be varied depending on the temperature and the duration of impressing a shock wave determined by the life of the carbon condensate in the reactor.

Assuming that the aggregation of a diamond substance from the detonation product is carried out within a moment of some microseconds, the present invention may be bound to (1) that the primary detonation product of an explosive is hardly made uniform in a chemically reactive range and (2) that the separation between condensation components and molecular components in the detonation product is hardly completed in a desired length of time. This implies that a chemical marking for the diamond synthesizing process, which incorporates a molecular compound and a fragment of the aggregate structure for identifying the aggregating mechanism of free carbons in the explosive and the reconstructing mechanism of carbon atoms, is possibly stored in the aggregate of the detonation product.

The chemical marking is classified into four categories: (i) a frame, bridge, alicyclic carbon compound as a fragment of the diamond or diamond-like structure consisting of $sp^3$ carbons; (ii) a derivative of a homocyclic or polycyclic aromatic compound as a fragment of the graphite structure (an $sp^2$ hybrid orbital); (iii) a straight-chain or branched alicyclic compound as a fragment of the amorphous compound up to the boundary of a carbon cluster or a fragment of the indication of a carbyne (R—$CH_2$—) structure; and (iv) a —C—N or —C—O bond contained compound as a fragment of the carbon particle at the surface.

EXAMPLE 15

Analysis of Chemical Marking

For clarifying and analyzing the chemical marking, a thermally decomposed product and a decomposed product (so-called organolytic decomposed product) in a super-critical organic solvent of the non-diamond phase of the UDD or BD of the present invention are examined.

More specifically, a cool extracting process is conducted by a Soxhlet apparatus at a range of solid:liquid=1:10 for an extracting duration of (3.6 to 4.32)×$10^5$ seconds. When the extracting of liquid is maximum, the organolytic decomposing process is carried out at a super-critical state. A pressure of not smaller than 5 MPa is applied at 573 to 673° K in an autoclave of 4×$10^{-4}$ $m^3$ in volume. Resultant extracts are subjected to low-temperature fluorescent spectrum analysis, gas-liquid chromatography analysis, chromatography-mass-spectrum analysis, IR spectrum analysis, and paramagnetic resonance spectrum analysis. For having different extracts, different types of the explosive mixture are provided including no-diamond contained reference samples. Depending on the synthesizing conditions, each explosive mixture produces different extracts which are bicyclic aromatic hydrocarbon and polycyclic aromatic hydrocarbon having one or more substituents. Also, various compounds including an $sp^2$ hybrid orbital or $sp^3$ hybrid orbital are obtained from the molecular product extracted at low temperature from the mixture. It is however understood that ultra-dispersed graphite or turbostrate (such as smectite or coal in a meso-phase where bonded atom layers are in parallel to each other, oriented in different directions, and/or placed one over another at random intervals) is more similar to any natural substance having such compounds than diamond. During the cool extracting process, the solid carbon matrix is not fractured but allows desorption/adsorption and washing out (extraction) of compound molecules dissoluble in an organic solvent. It is hence concluded that the identified compound is a carbon compound in an intermediate state between the detonation product and the carbon aggregate. Then, the relationship between the poly-aromatic compound discharged into an extract in the mixture, the diamond phase completed structure, and their proportion is examined. As a result, 5% at maximum of a soluble substance is discharged from the detonation product containing no diamonds.

EXAMPLE 16

Extract of Impurities

The extracting process allowing partial decomposition of a solid substance is carried out at 200 to 400° C. under a boosting condition or a super-critical condition of the organic solvent. The maximum super-critical liquefaction of carbon is conducted in pyridine which is one of the most active solvents. Table 9 illustrates the compositions thermally extracted using a relatively moderate solvent (hydrocarbon).

TABLE 9

Aromatic Polyheterocycles in high-temperature extracts from UDD and BD

| Structual formula of a compound | Solvents-extragents | | | |
|---|---|---|---|---|
| | BD | | UDD | |
| | Toluene | Benzene | Cyclo-hexane | Hydro-naphtalene |
|  | + | | | |
| 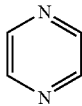 | + | | | + |
| 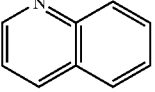 | | | + | + |
| 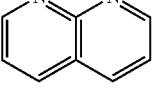 | + | + | + | + |
| 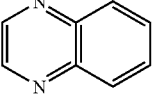 | | | | |
| 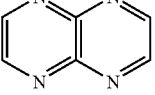 | + | + | | + |
| 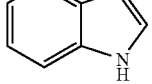 | | | + | + |
| 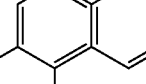 | | | | + |
| 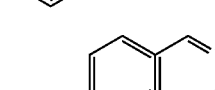 | + | | | |

Note."+" is the presence of a substance in extract
-normal structure -heptane, decane
-aromatic structure -benzene, toluene
-alicyclic structure -cyclohexane
-hydronaphtalene -tetralin, decalin
-These compounds are characterized by relative stability in the experiment conditions, an increase of solution power is pointed by the arrow.

In fact, the extracts are tinted different from thin yellow (n-hydrocarbon) to dark brown (hydro-naphthalene). The ratio of the carbon between the diamond phase and the graphite phase is changed after the extracting process and so the properties on the surface. Through 30 minutes of the supercritical liquefaction process, 10% or more of the carbon contained diamond phase is turned to a soluble state. As the decomposition to active chemical bonds of carbon is relatively slow, the surface of each cluster becomes not uniform. Stable structure units such as microscopic units of solid carbon discharged into the solution or micro units of individual molecules remain unaffected. In the units, nitrogen contained, poly-hetero-cyclic molecules up to tetra-cyclic having one or two nitrogen atoms in each ring are identified.

The formation of such a compound conforming to the organic chemistry principles may be explained by nitrogen consumed during the poly-condensation of a nitrogen contained monomer having carbon-nitrogen bonds and contained in the aggregate which has primary dressed diamonds in the UDD synthesizing. In this point, the present invention is differentiated from the conventional report, A. L. Vereshagin, V. F. Komarov, V. M. Mastinhin, V. V. Novosyolov, L. A. Patrova, I. I. Zolotuhina, N. V. Vichin, K. S. Baraboshikin, A. E. Petrov, Published Documents for the Conference Entitled name of In Proceeding of 5th All-Union Meeting on detonation, held in Krasnoyarsk, January 1991, pp. 99, [Investigation of properties of detonation synthesis diamond phase] where no characteristic triplet signals are present in the EPR spectrum of a UDD having carbon atoms in the diamond lattice replaced by impurity nitrogen atoms. However, this results from a difference between "poly-condensation for synthesizing the UDD during the detonation" in the present invention and common "dispersing growth of diamond crystals". It is found after the dispersing growth of diamond crystals that nitrogen impurities are trapped and dispersed in the diamond crystals. The synthesizing of the UDD of the present invention allows nitrogen impurities (more precisely, nitrogen-carbon bonds) to be taken into the aromatic rings (having a cyclic aromatic structure with high bonding energy) and then trapped in a preliminarily condensed packing. In the latter case, the paramagnetic properties of nitrogen are different from those of nitrogen impurities.

It is also assumed from the data of thermal absorption that the two are equal in the structure of the outer side of the shell of diamond clusters. The thermal absorption is measured in the present invention using a chromatography-mass-spectrum meter LKB-209 (made in Sweden). After thermal adsorption and desorption at 573° K in a helium flow, resultant products are continuously trapped in a capillary tube cooled down with liquid nitrogen. Then, the thermal adsorption/desorption product is evaporated by program heating at a rate of 4° per minute from 293° K to 543° K under a flow of helium gas carrier ($V_{He}$=2.5×10$^{-6}$ m·m$^3$) in a capillary column of a low polar phase (SPB-5,$1_k$=60 m, $d_c$=3.2×10$^{-4}$ m).

EXAMPLE 17

Mass Spectrum Analysis of the Absorption Materials

The product is identified through mass spectrum processing with a computer using a mass spectrum library. The composition of the products generated by adsorption and desorption at the surface of the UDD and the diamond contained mixture is shown in Table 10.

TABLE 10

Thermal desorption (T = 573° K.) from surface of UDD and BD (in 3 samples)

| Compound | | BD | UDD | UDD after treatment with hydrogen |
|---|---|---|---|---|
| Acetonitrile | | | ++ | |
| Nitromethane | | | + | |
| Butanone | | | + | |
| Teterahydrofuran | | | + | |
| Ethanol | | | | + |
| Acetone | | | | + |
| Ethyl acetate | | | ++ | +++ |
| Benzene and homologs | | ++ | +++ | ++ |
| Alcylbenzenes | $C_9$ | + | +++ | |
| | $C_{10}$ | +++ | + | |
| Alkanes | $C_7$ | | + | +++ |
| | $C_8$ | | + | + |
| | $C_9$ | | + | |
| | $C_{10}$ | +++ | +++ | |
| | $C_{11}$ | + | + | |
| Alkenes | $C_7$ | | + | |
| | $C_8$ | + | + | |
| | $C_9$ | | + | |
| | $C_{10}$ | | ++ | |
| Terpadienes | $C_{10}$ | + | ++ | |
| Alcylcyclopentanes | | + | | |
| Naphtalene | $C_{10}$ | + | + | |

"+" is the presence of a substance in thermal desorption products.

Generated by adsorption and desorption on the BD surface are only hydrocarbons including saturated $C_8$-$C_{11}$ hydrocarbon, unsaturated $C_8$-$C_9$ hydrocarbon, alicyclic hydrocarbon, and aromatic hydrocarbon. As alkane from $C_{10}$ is redundant, the adsorption/desorption product contains mainly n-decane $C_{10}H_{22}$. This is explained by the data of a carbyne structure (R—CH$_2$) as a thermodynamically efficient structure when a hydrocarbon chain of $C_{10}$-$C_{12}$ is packed by the consumption of cumulene bonds ($C_3H_7$—$C_6H_4$—CH) in the detonation product. While the presence of poly-cyclic aromatic net in the BD is confirmed by the present invention, aromatic hydrocarbon including alkylbenzene from $C_{10}$ is a small portion of the total mass generated by adsorption and desorption from the BD. It is hence apparent that the condensation of sp$^2$ carbon is high enough. However, the poly-cyclic aromatic net is highly mismatched and thus has fatty peripheral groups or so-called hydrocarbon fringes. Hydrogen in the adsorption and desorption product from the BD surface is of C—H bonding, inert type. This result is not differentiated from the teaching of ultra-dispersed carbon surface active hydrogen disclosed in Russian Patent No. 2046094 (synthetic carbon diamond material), Bjuljuten Izoberetnji (29), pp. 189 (1995).

The composition of the adsorption and desorption products from the UDD surface is highly complex and significantly varied. Other than hydrocarbon, nitrogen contained compounds and oxygen contain compounds are the products from oxidization at the carbon surface. As benzene and $C_7$-$C_{10}$ congeners have been developed, alkane of $C_{10}$ is generated from them. In particular, n-decane is redundant. The bridge alicyclic is developed as camphene and terpadiene $C_{10}H_{16}$. The composition of the adsorption and desorption product indicates that the interface in the diamond structure is exposed at minimum possibility.

The UDD cluster structure can be stabilized with transient carbon structures. When the UDD is processed at 400° C. in a hydrogen flow (as a hydrogen processed UDD in Table 11), the adsorption and desorption of a large amount of hydrocarbon $C_8$-$C_{11}$ is reversibly effected. However, when the surface carbon structure is decomposed, continuous or metastable surface structures are reconstructed as $C_2$-$C_7$ of hydrocarbon are developed.

It is known that the diamond particles synthesized by shock conversion are defined by the fractal rule (an infinite geometric series rule of having the shape of a set arranged similar to the shape of each member of the set and repeating this regularity to develop greater sets) and consists mainly of clusters of non-continuously aggregated small particles where at least a particle or clusters are joined together, as depicted in G. V. Sakovich, V. D. Gubarevich, F. Z. Badaev, P. M. Brilyakov, O. A. Besedina, Proceeding of Science of USSR, Vol. 310, No. 2, pp. 402 (1990), "Aggregation of diamonds obtained from explosives" and Luciano Pietronero, Erio Tosatti, Fractals in physics, Proceeding of the Sixth Trieste International Symposium of Fractals in Physics (1985), ICTP, Trieste, Italy, "Investigation of synthesis of ultra-dispersed diamonds", and A. V. Igonatchenko, A. B. Solohina, published document for the Conference entitled name of In proceeding of 5th All-Union Meeting on detonation, held in Krasnoyarsk, January 1991, pp. 164, "Fractal structure of ultra-dispersed diamonds."

The ion intensity in the UDD suspension liquid of the present invention is varied in a range from pH 2.1 to pH 2.3, but its pH increase with a higher temperature may initiate flocculation of suspended particles. The aggregation of the UDD of the present invention takes place in two steps. At the first step, the non-diamond components in the BD are clustered by oxidization during the chemical dressing process to develop a first aggregate which is relatively compact in the size. The second step involves aggregation of clusters to develop a second cluster structure which may easily be fractured. The second step lasts until the first aggregate starts flocculation. In some cases, there may be developed undesired aggregates between clusters and particles or between the second cluster structures.

EXAMPLE 18

Affection of the UDD Property on the Preparation Method

The properties are compared between the different UDD structures synthesized by a static conversion method (Method I, not shock conversion), a conventional shock conversion method (Method II, as depicted in G. A. Adadurov, A. V. Baluev, O. N. Breusov, V. N. Drobishev, A, I, Rogechyov, A. M. Sapegin, B. F. Tatsji, Proceeding of Academy of Science of USSR, Inorganic Materials, Vol. 13, No. 4, pp. 649 (1977), "Some properties of diamonds obtained by explosion method"), and the method of the present invention (Method III). The result is shown in Tables as follows.

TABLE 11-1

Characteristics of UDD powders of different nature.

| Name of Characteristic | Method I, static synthesis, ACM 1/0 | Method II, conventional detonation | Method III, detonation of the present invention |
|---|---|---|---|
| 1. Phase compositon | Diamond of cubic syngony ($a = 3.57 \times 10^{-10}$ m) | Diamond of cubic ($a = 3.57 \times 10^{-10}$ m) and hexagonal syngony ($a = 2.52 \times 10^{-10}$ m) or cubic syngony | Diamond of cubic syngony ($a = 3.57 \times 10^{-10}$ m) |
| 2. Substructure dimensions of coherent dispersion bands, ($\times 10^{-10}$ m); | Not found | 100~120 | 40 |
| microstresses of the II type($\Delta\alpha/\alpha$); | — | $(1.0~1.9) \times 10^{-3}$ | Absent |
| density of dislocation, $m^{-2}$ | — | — | $1.8 \times 10^{17}$ |
| 3. Picnometric density, ($\times 10^{-3}$ kg/m$^3$) | 3.49 | 3.20-3.40 | 3.30 |
| 4. The particle size, ($\times 10^{-9}$ m) | 0~2000 | 41~82 10~50(from graphite) 20~800(carbon black) | 48.1 (2~50) 19.6 (2~20(from graphite)) 4 (carbon black) |
| 5. Specific surface ($\times 10^{-3}$ m$^2$/kg) | 13.5 | 20.42 | 217 |
| 6. Chemical composition, mass. % | C = 99.0 Ni, Mn, Cr, Fe = 0.5 Si = 0.2 B = 0.2 H = 0.1 O = 0.1 | | C = 80.75 H = 1.35 N = 2.00 O = 15.90 Si = traces |

TABLE 11-2

Characteristics of UDD powders of different nature.

| | Method of diamond production and its brand | | |
|---|---|---|---|
| Name of Characteristic | Method I, static synthesis, ACM 1/0 | Method II, conventional detonation | Method III, detonation of the present invention |
| 7. Incombustible(unburnt) resdiue, mass. % | <0.1 | 0.1 | <2.0 |
| 8. Temparature of the beginning of oxidation in air, °K. | 723 | — | 673 |
| 9. Temparature of the beginning of graphitisation in vacuum, °K. | 1373 | >1073 | 1423(1373~1473) |
| 10. Electrocal resistance, ($\Omega$) | $1 \times 10^{11}$ | — | $7.7 \times 10^9$ (($7.7 \times 8.1) \times 10^9$) |
| 11. The loss tangent of a dielectric at requency $\theta = 10^3$ Hz | 0.0100 | — | 0.0145 (0.0143~0.0363) |
| 12. Specific magnetic susceptibility ($\times 10^3$/kg) | $0.5 \times 10^{-8}$ | — | $<1.0 \times 10^{-8}$ |
| 13. Degree of water receptivity, (Joule/mol·kg) | −1480 | — | >−3100 |
| 14. Electrophoretic charge of the surface ($\times 10^3$ V) | −6.53 | — | >−78.44 |
| 15. Adsorption potential A ($\times 10^3$ J/kg) | 14.2 | — | >384 |
| Specific adsorption potential A, (Joule/m$^2$) | 1.005 | — | >2.16 |

As being apparent from Tables above, the UDD synthesized by the method III of the present invention has as a low carbon content as smaller than 90%, as a high hydrogen content as not smaller than 0.8%, and as a high oxygen content as not smaller than 6.8%. This is also differentiated from other diamonds by the fact that the specific surface area is substantially 10 times greater, the adsorptivity is 384×10$^3$ J/kg or more as almost 10 times greater, and the surface potential is not smaller than −77.44×10$^3$ V as almost 10 times greater. Also, the UDD of the present invention has a level of the surface conductivity and is slightly greater in the water absorptivity. However, the UDD of the present invention is relatively lower in the intra-air oxidization start temperature and the intra-vacuum graphitization start temperature while not different in the electrical and magnetic physical properties from other diamonds. The UDD synthesized by the conventional method II has two phases, a cubic crystal with a crystalline constant of a=3.57×10$^{-10}$ m and a hexagonal crystal with a crystalline constant of a=2.52×10$^{-10}$ m. The UDD synthesized by the method III of the present invention has only a cubic crystal phase at a crystalline constant of a=3.57×10$^{-10}$ m.

[Use of the UDD Fine Particle as a Carrier]

As described before, the surface of the UDD fine particle of the present invention is covered with functional groups such as —COOH, —CHO, —C—O—C—, —OH, —SO$_3$H, —NO$_3$, —NO$_2$, and —NH$_2$ groups. Also, the UDD fine particle of the present invention has a specific density of around 4.5×10$^5$ m$^2$/Kg, and a large surface carbon ratio ($C_{surf}/C_{total}$). In addition, almost all the surface carbon (around 100%) has a functional group.

Thus, the UDD fine particle of the present invention has a large amount of and various kinds of functional groups, so that the UDD fine particle of the present invention may have an ability to covalently bond with various organic compounds. Therefore, the UDD fine particle of the present invention is a preferable material to immobilize such compounds.

For example, a protein has a free amino group therein, which may bond to the surface of the UDD fine particle through the —COOH or —CHO group. Also, the carboxylic group in a protein may bond to the —NH$_2$ or —OH group on the surface of the UDD fine particle, immobilizing the protein.

Also, a sugar chain in a polysaccharide or sugar protein is immobilized on the UDD fine particle of the present invention, by reaction between the —OH group in the sugar chain and the —COOH or —CHO group of the UDD fine particle, or between the —CHO group of the sugar chain and —NH$_2$ or —OH group of the UDD fine particle.

Further, a DNA or RNA is immobilized on the UDD fine particle of the present invention by reaction, for example, between —NH$_2$, —OH, or phosphate group of the DNA or RNA and the functional groups on the surface of the UDD fine particle.

Of course, such immobilization can be made via a suitable linker to react the UDD fine particle with the target compound.

On the other hand, the UDD fine particle of the present invention, as described before, has a negative electric charge, having a high surface potential. Since the surface of the particle of AIDS virus and so on has a positive electric charge, the UDD fine particle of the present invention may be useful in a carrier for trapping virus. Also, a specific protein to recognize to bond may be combined with the UDD fine particle of the present invention, through an amido bond or ester bond, for trapping a virus.

[DNA Chip]

The immobilization carrier of the UDD fine particle of the present invention is preferably used as a DNA chip. Description hereinafter relates to a DNA chip using the UDD fine particle of the present invention.

According to the present invention, a DNA chip is prepared by the steps comprising providing on a support substrate a layer of the UDD fine particle of the present invention to prepare a DNA chip substrate; and covalently combining the functional group of the UDD fine particle with, for example, a probe of DNA, via, if necessary, a linker molecule.

The support substrate may include slide glass, silicone substrate, ceramics, paper, resin products such as polycarbonate, polyethylene terephthalate, styrene polymer, and acrylic (methacrylic) polymer.

According to the present invention, the UDD fine particle of the present invention may be provided on the support substrate as follows:

(1) The UDD fine particle of the present invention is suspended in an adhesive solution, and then, it is coated and attached to on the support substrate. If necessary, the surface of the coating is treated with a solvent to expose the surface of the UDD fine particle. Thus, a DNA chip substrate is obtained. This process is independent on the kinds of the support substrate.

(2) A support substrate of slide glass, silicone substrate or ceramics substrate is covalently combined with a silane coupling agent such as γ-aminopropyl triethoxysilane, N-β(aminoethyl) γ-aminopropyl trimethoxysilane, and N-β(aminoethyl) γ-aminopropyl methyl dimethoxysilane, and then, the incorporated amino group on the support substrate is reacted with the negative group such as carboxylic group on the surface of the UDD fine particle of the present invention. Thus, this process may produce a DNA chip having a layer of the fine particle of the present invention strongly combined with the support substrate.

(3) A support substrate of a resin material having a free amino group, carboxylic group and so on is used. The functional group of the support substrate of resin material is reacted with a functional group of the UDD fine particle of the present invention, to strongly combine a layer of the UDD fine particle of the present invention with the surface of the support substrate.

In case of this process, a support substrate of resin material has a functional group in its polymer chain, which is directly combined with the UDD fine particle of the present invention. Alternatively, the support substrate of a resin material is molded, and then, a functional group is incorporated thereon, followed by combining it with the UDD fine particle of the present invention. In the former process, acrylic (methacrylic) acid ester/acrylic acid copolymer, styrene/acrylic acid copolymer, polyvinyl alcohol and so on may be used. The carboxyl group or hydroxyl group of such a resin product is combined with an amino group or hydroxyl group of the UDD fine particle of the present invention, so as to obtain a DNA substrate having a layer of the UDD fine particle of the present invention on its surface. Also, in case of the latter process, a support substrate of, for example, polystyrene is treated with an amine nitrite to obtain a nitroso, which is reduced to incorporate an amino group at a para portion of the polystyrene. Then, the amino group is reacted with the carboxyl group of the UDD fine particle of the present invention to obtain a DNA chip substrate having the UDD fine particle of the present invention on its surface.

(4) The support substrate is coated with a poly positive ion such as polylysine, polyethylene imine and polyalkylamine, thereby statically combining it on the surface of the support substrate to incorporate an amino group, which is reacted with the carboxyl group of the UDD fine particle of the present invention, so as to obtain a DNA chip substrate having the UDD fine particle of the present invention on its surface.

(5) The UDD fine particle of the present invention is dispersed into a solution of a resin, and then, the resin is cured to be formed into a body, followed by cutting or grinding it to expose the UDD fine particle of the present invention on the surface of the body, so as to obtain a DNA chip substrate having the UDD fine particle of the present invention on its surface.

In order to obtain the DNA chip according to the present invention, any process to produce it may be selected, but to stably hold the UDD fine particle of the present invention on the support substrate, the process (2) or (3), accompanying with covalent bonding, may be preferable.

In order to prepare a DNA chip, it is necessary to place a DNA or RNA probe on a specific portion of the DNA substrate. Well-known process may be used. For example, a DNA or RNA as a probe is sequentially spotted on a specific portion of the DNA substrate by means of a spotter equipment. Alternatively, using a photo lithography method, which may be used in the manufacture of semiconductor devices, may be used. In order to form a specific DNA probe is synthesized at a specific portion of the DNA, a photo-mask is formed at the other portion. Then, an ultraviolet ray is irradiated to subsequently synthesize a DNA or RNA while removing the protective group of a DNA monomer having a protective group.

Thus, the specific DNA or RNA placing at a specific portion of the DNA chip substrate is then immobilized on a DNA chip. According to the present invention, the functional group of the UDD fine particle formed on the DNA chip substrate is covalently combined to array the DNA or RNA probe on the substrate.

Each functional group of the surface of the UDD fine particle of the present invention is significantly active. In particular, —COOH group (including its anhydride) is included in a great number of amount, so that it is preferable to immobilize a fragment of DNA or mRNA. For this immobilization, an aliphatic hydrocarbon chain having an amino group may be incorporated at the 5' terminal phosphate group of a DNA probe. A well known process may be used in this process. ("Nucleic acids Res." 11(18), P. 6513 (1983)) Thus, a DNA probe incorporating an amino group is obtained, which is immobilized by amido bonding through the carboxyl group of the UDD fine particle formed on the DNA chip substrate.

Also, the UDD fine particle of the present invention has an amino group at its surface (in an amount of 5% of the functional groups), which is used to immobilize a fragment of DNA or mRNA as a probe. Also, this may be done, for example, by reacting, under existence of PDC (p-phenylenediamine diisocyanate), the DNA probe incorporating an amino group, to immobilize the DNA probe on the DNA chip substrate. Further, as the method to utilize an amino group on the surface of a carrier for immobilizing a DNA probe, there may be a method that 2,4-dihalogen triazine compound is reacted with the DNA incorporating an amino group (JP Laid-Open Patent Publication No. 2001-128697). This method is also available to immobilize a DNA probe of the present invention.

In addition, —CHO group on the surface of the UDD fine particle may be used for immobilizing a fragment of a DNA or mRNA as a probe. Aldehyde group with the DNA incorporating an amino group forms a Schiff base, for immobilizing the DNA probe on the DNA ship substrate. Further, —OH group on the surface of the UDD fine particle is also active. For example, the hydroxyl group with the 5' terminal phosphate group of a DNA probe may form a phosphate ester, so as to immobilize a DNA probe on the DNA chip substrate.

In the immobilization of DNA or mRNA on the DNA chip substrate, only the specific functional group of the UDD fine particle may be designed to be reacted, by protecting to form a suitable protective group such as an acyl group.

Thereby obtained DNA chip is supplied to hybridization with cDNA as a sample marked by, for example, a fluorescent dye. The cDNA as a sample which is not hybridized is removed by washing. The hybridized cDNA are read their location and strength by using a scanner, followed by subjecting to image data processing, to read, for example, their functions corresponding to the DNS probe.

As described above, this invention is described on the embodiment of a DNA chip substrate which immobilizes a DNA or RNA. The DNA chip substrate of the present invention is not limited to the immobilization of them. For example, it may be used for immobilizing a physiologically active material, an acceptor, or a protein, for the purpose of researching the relationship between physiologically active material and acceptor, or researching a peptide or protein bond portion in a gene.

[A Carrier for Trapping Virus and a Virus Vaccine]

The UDD fine particle of the present invention, as described above, has a great number of functional groups on its surface, and in addition, it has a very small size in the order of nanometers. Also, it has high hydrophilicity, very good dispersibility in the neutral and acid ranges, and is non-toxic to living bodies so as to have preferable properties to be used as a carrier for trapping virus such as AIDS virus (HIV), and as a virus vaccine.

Next, a carrier for trapping virus and a virus vaccine, using the UDD fine particle of the present invention, are described in detail with respect to the case to target an AIDS virus.

In order to obtain a carrier for trapping AIDS virus using the UDD fine particle of the present invention, the carboxyl group on the surface of the UDD fine particle of the present invention is, first of all, reacted with the amino group of concanavalin A as a mannose combinable lectin, to obtain a carrier for trapping virus in which concanavalin A is immobilized on the UDD fire particle of the present invention.

On the other hand, since the sugar chain of a sugar protein gp120 on the surface of AIDS virus is composed of a sugar of mannose, the carrier in which concanavalin A is immobilized on the UDD fire particle of the present invention may trap AIDS virus very efficiently.

Also, in order to prepare AIDS virus vaccine by using the UDD fine particle of the present invention, a suspension solution including a particle of attenuated or inactivated AIDS virus by means of subculture, heating and chemical treatment, or a partial protein of AIDS virus having at least the protein sugar of the AIDS virus, is prepared. With the suspension solution, the carrier for trapping virus in which concanavalin A is immobilized on the UDD fire particle of the present invention is mixed. Thus, the virus particle of AIDS or the partial protein is held by the carrier for trapping virus. On the other hand, the UDD fine particle of the present invention has good dispersibility in a neutral and an acid ranges, but exceeding its pH valued of 8, it may aggregate and precipitate. The suspension liquid including the carrier which traps the AIDS virus is adjusted into a pH value over 8, and then, the precipitated materials are taken by means of centrifugal separation, so as to easily obtain an AIDS vaccine. Also, by using such a precipitation measure of pH adjustment, an AIDS treatment may be made by application of blood filtration. Since the UDD fine particle of the present invention is remarkably minute and it hardly aggregates in a mild acidic solution such as a blood, it may be possible to prepare a carrier for trapping virus in which a protein to recognize to bond AIDS virus such as concanavalin A is immobilized, for administer the carrier directly into the blood of an AIDS carrier by means of intravenous or IV push. The blood is taken out to the outside of the body, to adjust it into a pH value over 8, so as to separate the carrier trapping AIDS virus by precipitation and filteration for removal. The separated blood is gotten back into a pH value in the original mild acid range, to reflow it into the body. Thus, the AIDS virus infected on a living body may be decreased.

Next, the examples of the present invention are described, but the scope of the present invention is not limited thereto.

EXAMPLE 1

Preparation of a DNA Chip Substrate

A slide glass having a size of 40 mm×40 m was soaked into an ethanol solution including 2% by weight of aminopropyl ethoxysilane for a period of 15 minutes, and then, it was taken out for drying, to obtain a slide glass as a support substrate having a silane coupling agent combined on its surface. On the other hand, an aqueous suspension solution including 10% of the UDD fine particle as sample No. 5 listed in Table 2 as described above, into which a carbodiimido is added. Then, into the suspension solution, the slide glass was soaked for a period of 1 hour, so as to react the amino group of the silane coupling agent with the carboxyl group of the UDD fine particle. After the reaction, it was taken out to obtain a DNA chip substrate having the UDD fine particle on its surface.

A DNN synthesis equipment was used to synthesize an oligonucleotide having a base sequence as follows:

GCATCTCATTGACCATCATATTAT (SEQ ID No. 1)

At the final stage of the synthesis of the oligonucleotide, an Aminolink II (manufactured by Applied Biosystems Corporation) was used to aminate the 5' terminal of the oligonucleotide by incorporating a $NH_2$ $(CH_2)_6$ group. The aminated oligonucleotide was immobilized on a layer of the UDD fine particle of the DNA chip by means of a general process using PDC (p-phenylene diisothiocyanate).

EXAMPLE 2

Preparation of a Carrier for Trapping Virus

The UDD fine particle as sample No. 5 listed in Table 2 as described above was reacted with concanavalin A in a solution including 50 mM of $KH_2$ $PO_4$ and 10 mM of HEPES including a cabodiimido, so as to combine the amino group of concanavalin A with the carboxyl group of the UDD fine particle, resulting in obtaining a carrier for trapping virus in which concanavalin A was immobilized on the UDD fine particle.

On the other hand, a suspension solution of HIV-1 was prepared, into which the suspension solution for trapping virus, as described above, was mixed, followed by adding sodium hydrate to adjust it into a pH value of 8.5. Thus, thereby obtained precipitation material was separated by means of centrifugation, and then, its amount of gp120 of the AIDS virus and its viral infectivity were measured with respect to the skimming solution. The control included gp120 in an amount of about 2500 (pg/ml), and the sample using the carrier for trapping virus of the present invention included it in an amount of 100 (pg/ml) or less. The control had a viral infectivity of about $10 \times 10^4$ (CCID 50/ml), and the sample using the carrier for trapping virus of the present invention had a viral infectivity of about 2 (CCID 50/ml) or less. Consequently, the carrier for trapping virus of the present invention showed a significantly high ability to trap AIDS virus.

(IgA Inductivity by a Carrier Trapping Aids Virus)

The UDD fine particle as sample No. 5 obtained by Experiment 1 as described above and concanavalin A, were used to prepare a carrier for trapping virus, to trap HIV-1 inactivated by heating. This was used as an immunity source to give immunity to a mouse (BALB/c ♀ at an age of 8 weeks), followed by additional immunization after 3 weeks thereof. The amount of administered antigen was about 10 ng per an immunization (based on gp120 conversion rate), which was amounted to about 2×10⁸ pieces of the virus particle. Endovaginal thereof was used for administration. Every 10 days after the first administration, a liquid obtained by washing the Endovaginal was collected to measure the amount of IgA antibody by means of ELISA. High Inductivity of the IgA antibody was observed only where the carrier for trapping virus of the present invention was used to trap AIDS virus as an immunity source. Inductivity of the IgA antibody was hardly observed where an AIDS virus alone or the carrier for trapping virus alone was administered. As a conclusion, since IgA is an antibody to function in a mucosa tissue, this result suggested to form a barrier at an ingression path of a virus.

As being apparent from the detailed and concrete description, the UDD fine particle of the present invention has a particle size in the order of nanometer, and a significant large specific surface area while having, on its surface, a great number of various kind of functional groups including carboxyl group, amino group, hydroxyl group and sulfonyl group, and in particular, negative charge functional groups. In addition, it remarkably shows good dispersibility to stably exist in an aqueous suspension solution so as to hardly aggregate. Further, it has a significant good hydrophilicity and is excellent in biocompatibility and non-toxic to living bodies, so it is safe. Therefore, the using of the diamond fine particle may be possible to produce a significantly useful material or a carrier for immobilizing virus. Especially, the DNA chip substrate using the same may immobilize a DNA probe by means of simple process. Also, the carrier for trapping virus using the same may be possible to trap virus remarkably efficiently. Furthermore, the trapping of virus on the carrier may provide a significantly useful vaccine.

propyl amine, isopropyl amine, dipropyl amine, aryl amine, aniline, N,N-dimethyl aniline, diisopropyl amine, poly-alkylene poly-amine such as diethylene triamine and tetraethylene pentamine, 2-ethylhexyl amine, cyclohexyl amine, piperydine, folmamide, N,N-methyl folmamide, and urea.

4. A fine, diamond particle according to claim 1, wherein the diamond particle has an element composition including 72 to 89.5% of total carbon, 0.8 to 1.5% of hydrogen, 1.5 to 2.5% of nitrogen, and 10.5 to 25.0% of oxygen.

5. A fine, diamond particle according to claim 1, wherein the diamond particle has no particle size over 1000 nm or below 30 nm, having a narrow distribution of number average particle diameter (ØMn) of 150 to 650 nm.

6. A fine, diamond particle according to claim 1, wherein the diamond particle, when analyzed by an X-ray diffraction (XD) spectrum analysis using Cu,Kα radiation, has the largest peak at a Bragg angle of 43.9° (2θ±2°), strong and characteristic peaks at either of Bragg angles of 73.5° and 95°, a biased halo at a Bragg angle of 17°, and no peak at a Bragg angle of 26.5°.

7. A fine, diamond particle according to claim 1, wherein the diamond particle has a specific surface area of $1.50 \times 10^5$ m²/kg or more, wherein all of carbon atoms on the surface of diamond particle are bonded with hetero atoms, wherein the diamond particle has a total absorption space of 0.5 m³/kg or more.

---

---

What is claimed is:

1. A fine, diamond particle, comprising:
   a diamond particle having a functional group —NH₂ directly combined with carbon of the diamond particle on a surface thereof,
   wherein the diamond particle has a crystalline structure.

2. A fine, diamond particle according to claim 1, wherein the diamond particle is prepared by the steps comprising:
   preparing an initial mixture including a diamond particle by means of explosion of a detonating agent;
   subjecting the initial mixture to an oxidation treatment by using nitric acid to obtain a suspension liquid;
   neutralizing the suspension liquid with a basic material; and
   purifying the neutralized suspension liquid to obtain a diamond particle.

3. A fine, diamond particle according to claim 2, wherein the basic material is selected from the group consisting of hydradine, methyl amine, dimethyl amine, trimethyl amine, ethyl amine, diethyl amine, triethyl amine, ethanol amine, 8. A fine, diamond particle according to claim 1, further comprising a DNA or RNA immobilized on the diamond particle.

9. A fine, diamond particle according to claim 1, further comprising a protein or peptide immobilized on the diamond particle.

10. A fine, diamond particle according to claim 9, further comprising a retrovirus immobilized on the surface of the diamond particle.

11. A fine, diamond particle according to claim 9, further comprising an AIDS virus immobilized on the surface of the diamond particle.

12. A fine, diamond particle according to claim 9, wherein the protein is a lectin.

13. A DNA chip substrate, comprising:
   a support member; and
   a fine, diamond particle according to claim 1 provided on the support member.

14. A fine, diamond particle according to claim 1, further comprising an AIDS virus partial protein immobilized on the surface of the diamond particle.

15. A fine, diamond particle according to claim 1, wherein the functional group is combined by neutralizing with a basic material which is volatile or which decomposes to generate a volatile material.

16. A fine, diamond particle according to claim 1, wherein the functional group is combined on the carbon of the surface by neutralizing with a basic material which produces a gas.

17. A fine, diamond particle according to claim 1, wherein the diamond particle having a specific density in the range of $3.20 \times 10^3$ kg/m$^3$ to $3.40 \times 10^3$ kg/m$^3$.

* * * * *